United States Patent [19]

Wagnon et al.

[11] Patent Number: 5,773,612

[45] Date of Patent: Jun. 30, 1998

[54] INDOL-2-ONE DERIVATIVES

[75] Inventors: Jean Wagnon, Montpellier; Bernard Tonnerre, Vailhauques; Alain Di Malta, Saint Clement De Riviere; Richard Roux, Vailhauques; Marie-Sophie Amiel, Perols; Claudine Serradeil-Legal, Escalquens, all of France

[73] Assignee: Sanofi, Paris, France

[21] Appl. No.: 640,080

[22] Filed: Apr. 30, 1996

Related U.S. Application Data

[62] Division of Ser. No. 500,924, filed as PCT/FR94/01528, Dec. 23, 1994, Pat. No. 5,594,023.

[30] Foreign Application Priority Data

Dec. 24, 1993 [FR] France .................................... 93/15638

[51] Int. Cl.⁶ ........................ C07D 209/34; C07D 209/30
[52] U.S. Cl. ............................. 544/62; 544/144; 544/373; 546/201; 546/277.7; 548/466; 548/483
[58] Field of Search ..................... 548/483, 486, 548/466; 544/62, 144, 373; 546/201, 277.7

[56] References Cited

U.S. PATENT DOCUMENTS 4,021,469   5/1977   Weston ................................... 260/471

FOREIGN PATENT DOCUMENTS 1125671   8/1968   United Kingdom .

OTHER PUBLICATIONS

Bolotov et al., Chemical Abstracts 92:110770h, 1980.
Ogata et al., Chemical Abstracts 95:203829m, 1981.
Chemical Abstracts 94: 139809e, 1981.
Sato, Chemical Abstracts 91:175193w, 1979.
Bolotov et al., Chemical Abstracts 86:121089v, 1977.

Primary Examiner—Mukund J. Shah
Assistant Examiner—Deepak R. Rao
Attorney, Agent, or Firm—Bacon & Thomas

[57] ABSTRACT

A compound of formula II'

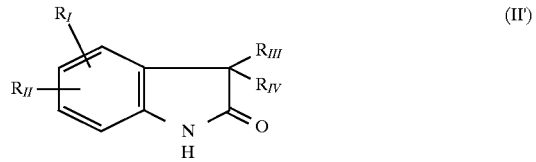

in which $R_I$ is an ethoxy group or a chlorine atom;
$R_{II}$ is hydrogen, a chlorine atom or a methyl group;
$R_{III}$ is a chlorophenyl group or a methoxyphenyl group;
$R_{IV}$ is an amino group, a group $NR_9R_{10}$ or $NR_9R_{XI}$, or a piperazin-1-yl radical substituted in the 4-position by a $(C_2-C_{10})$alkylene group substituted by an amino group which is free or carries a protective group;
$R_{10}$ is $(CH_2)_pR_{35}$ or a $(C_2-C_{10})$alkylene group substituted by $R_{21}$;
$R_{XI}$ is a $(C_1-C_{12})$alkyl group or a group $\omega$-$R_{32}R_{33}N(C_1-C_4)$-alkylcarbonyl; and
$R_{21}$ is $R_{36}$; a group $OR_{37}$; a group $NR_{32}R_{33}$; a cyano group; a group $S(C_1-C_7)$alkyl; a group $SO(C_1-C_7)$alkyl; or a group $SO_2(C_1-C_7)$alkyl;
$R_{35}$ is a piperid-4-yl group which is unsubstituted or substituted in the 1-position by a $(C_1-C_7)$alkoxycarbonyl group or by a $(C_1-C_7)$alkyl group; or a pyrid-2-yl group;
$R_{37}$ is $R_{13}$; a $(C_3-C_7)$cycloalkyl group; a $(C_1-C_6)$alkylene group substituted by $R_{24}$; a $(C_2-C_6)$alkylene group substituted by a hydroxyl or a $(C_1-C_7)$alkoxy group; or a $(C_2-C_6)$alkylene group substituted by an amino group which is free or substituted by one or two $(C_1-C_7)$alkyl groups or by a protective group;
$R_{24}$ is a carboxyl group; a $(C_1-C_7)$alkoxycarbonyl group; a benzyloxycarbonyl group; or a carbamoyl group which is free or substituted by one or two $(C_1-C_7)$alkyl groups.

3 Claims, No Drawings

INDOL-2-ONE DERIVATIVES

This application is a Division of application Ser. No. 08/500,924, filed Jul. 31, 1995, now U.S. Pat. No. 5,594,023 which is a 371 of PCT/FR94/01528 filed Dec. 23, 1996.

The present invention relates to 1,3-dihydroindol-2-one derivatives substituted in the 3-position by a nitrogen-containing group, to their preparation and to the pharmaceutical compositions in which they are present.

The compounds according to the present invention have an affinity for the vasopressin and/or ocytocin receptors.

Vasopressin is a hormone known for its antidiuretic effect and its effect in the regulation of arterial pressure. It stimulates several types of receptors, namely $V_1$ ($V_{1a}$, $V_{1b}$) and $V_2$. These receptors are localized in the liver, vessels (coronary, renal, cerebral), platelets, kidney, uterus, adrenal glands, central nervous system and pituitary gland. Ocytocin has a peptide structure similar to that of vasopressin. The ocytocin receptors are also found on the smooth muscle of the uterus, as well as on myoepithelial cells of the mammary gland, in the central nervous system and in the kidney. The localization of the different receptors is described in: S. JARS et al., Vasopressin and oxytocin receptors: an overview, in Progress in Endocrinology, H. IMURA and K. SHIZURNE ed., Experta Medica, Amsterdam, 1988, 1183–1188, and in the following articles: Presse Médicale, 1987, 16 (10), 481–485; J. Lab. Clin. Med., 1989, 114 (6), 617–632; and Pharmacol. Rev., 1991, 43 (1), 73–108. Vasopressin thus exerts cardiovascular, hepatic, antidiuretic and aggregating effects and effects on the central and peripheral nervous system and in the uterine domain. ocytocin is involved in parturition, lactation and sexual behavior.

The compounds according to the present invention make it possible selectively either to mimic the effects of the hormone (in the case of agonists) or to inhibit them (in the case of antagonists). Vasopressin receptor antagonists can affect the regulation of the central and peripheral circulation, especially the coronary, renal and gastric circulation, as well as the regulation of hydration and the release of adrenocorticotrophic hormone (ACTH). Vasopressin agonists can advantageously replace vasopressin or its analogs in the treatment of diabetes insipidus; they can also be used in the treatment of enuresis and in the regulation of hemostasis: treatment of hemophilia and von Willebrand's syndrome, antidote to platelet aggregating agents, F. A. LASZLO, Pharmacol. Rev., 1991, 43, 73–108; and Drug Investigation, 1990, 2 (Suppl. 5), 1–47. The hormones themselves, namely vasopressin and ocytocin, and some of their peptide or non-peptide analogs are used in therapeutics and have been found to be effective. Several reviews and numerous literature articles may be mentioned: Vasopressin, P. GROSS et al. ed., John Libbey Eurotext, 1993, in particular 243–257 and 549–562; F. A. LASZLO and F. A. LASZLO Jr., Clinical perspectives for vasopressin antagonists, Drug News Perspect., 1993, 6 (8); W. G. NORTH, J. Clin. Endocrinol., 1991, 73, 1316–1320; J. J. LEGROS et al., Prog. Neuro-Pharmacol. Biol. Psychiat., 1988, 12, 571–586; K. E. ANDERSSON et al., Drugs Today, 1988, 24 (7), 509–528; D. L. STUMP et al., Drugs, 1990, 39, 38–53; S. CALTABIANO et al., Drugs Future, 1988, 13, 25–30; Y. MURA et al., Clin. Nephrol., 1993, 40, 60–61; and Faseb J., 1994, 8 (5), A 587, 3398.

Thus the compounds according to the invention are useful especially in the treatment of complaints of the central and peripheral nervous system, the cardiovascular system, the renal domain and the gastric domain and in disorders of sexual behavior, in man and animals.

Patent ZA 83 09532 describes in particular a 1,3-dihydroindol-2-one derivative of the formula

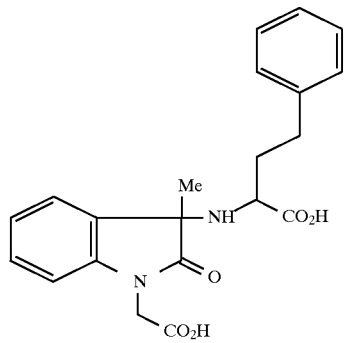

This compound is useful as a converting enzyme inhibitor and as an antihypertensive.

Patent application GB 1 125 671 describes 3-amino-3-arylindolone derivatives of the formula

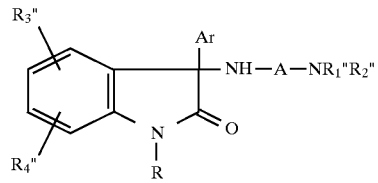

in which:

R is hydrogen or a $C_1$–$C_4$-alkyl or $C_1$–$C_4$-dialkylamino group;

A is a $C_2$–$C_5$-alkylene;

R"$_1$ and R"$_2$ are each an alkyl or, together with the nitrogen atom to which they are bonded, are a heterocyclic radical, for example the piperidino, pyrrolidino or morpholino radical;

R"$_3$ and R"$_4$ are each hydrogen, a $C_1$–$C_4$-alkyl, a $C_1$–$C_4$-alkoxy or a halogen; and Ar is an optionally substituted benzyl or phenyl.

These compounds are useful as diuretics.

Several patent applications have recently described families of compounds of non-peptide structure which are active on the vasopressin and/or ocytocin receptors. There may be mentioned patent applications EP 382 185, EP 444 945, EP 514 667, EP 469 984 and EP 526 348, patent applications WO 91/05549 and WO 93/15051 and, more particularly, patent application JP-03/127732. This last patent application describes indole-3-propionic acid derivatives of the formula

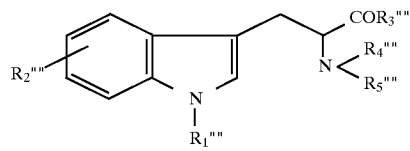

in which:

R""$_1$ is hydrogen, an alkyl, an alkenyl, a phenylalkyl, a tetrahydrofuryl, an alkoxycarbonyl, an alkoxycarbonylalkyl, a carboxyalkyl or an alkanoyl;

R""$_2$ is hydrogen, a hydroxyl, an alkoxy, an alkyl, a phenylalkyl, a phenylalkoxy or a halogen;

R""$_3$ is a hydrogen, an alkoxy, a free or substituted amino group or an amino acid residue;

R""$_4$ is hydrogen, an alkyl or a phenylalkyl; and

R""$_5$ is a benzoyl, a phenyl, an alkyl, a phenylalkenylcarbonyl, a thienylcarbonyl, a phenylsulfonyl, a pyridylcarbonyl or an imidazolylcarbonyl, it being possible for the phenyl and alkyl groups of the substituent R""$_5$ to be substituted.

These compounds are vasopressin antagonists.

U.S. Pat. No. 4 803 217 claims hapalindolinones obtained by fermentation which are vasopressin antagonists. These compounds have the following formula:

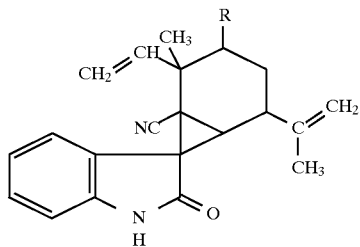

in which R is H or Cl.

According to one of its features, the present invention relates to compounds of the formula

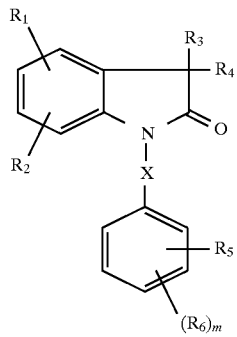

(I)

in which:

R$_1$ and R$_2$ are each independently a hydrogen; a halogen; a (C$_1$–C$_7$)alkyl; a (C$_1$–C$_7$)alkoxy; or a trifluoromethyl;

R$_3$ is a (C$_1$–C$_7$)alkyl; a (C$_3$–C$_7$)cycloalkyl; a cyclohexyl substituted by one or two (C$_1$–C$_4$)alkyls; a cyclohexylmethyl; a phenyl which is unsubstituted or monosubstituted or polysubstituted by a halogen, a (C$_1$–C$_7$)-alkyl, a hydroxyl, a (C$_1$–C$_7$)alkoxy, a benzyloxy or an acetoxy; or a benzyl which is unsubstituted or monosubstituted or polysubstituted by a halogen, a (C$_1$–C$_7$)-alkyl, a hydroxyl, a (C$_1$–C$_7$)alkoxy, a benzyloxy or an acetoxy;

R$_4$ is an azido; a 2,2-dimethylhydrazino group; a (C$_1$–C$_7$) alkylsulfonamido; a phenylsulfonamido in which the phenyl is unsubstituted or monosubstituted or polysubstituted by a halogen, a (C$_1$–C$_7$)alkyl, a hydroxyl, a (C$_1$–C$_7$)alkoxy, a benzyloxy or an acetoxy; a dimethylaminosulfonamido; a group NR$_7$R$_8$; a group NR$_9$R$_{10}$; a group NR$_9$R$_{11}$; a heterocyclic radical R$_{12}$; a piperazin-1-yl substituted in the 4-position by a (C$_2$–C$_{10}$)alkylene group substituted by an amino group which is free or carries a protective group; a lactoylamino group; a mandeloylamino group; an N'-(1-phenylethyl)ureido group; or an N'-(1-naphth-1-ylethyl)ureido group;

R$_5$ is hydrogen or has one of the meanings given for R$_6$;

R$_6$ is a halogen; a (C$_1$–C$_7$)alkyl; a trifluoromethyl; a cyano; an aminomethyl in which the amino is free or substituted by one or two (C$_1$–C$_7$)alkyls; a nitro; a group NR$_9$R$_{11}$; a heterocyclic radical selected from pyrrol-1-yl, Δ3-pyrrolin-1-yl, pyrrolidin-1-yl and morpholin-4-yl; a group OR$_{13}$; a group SR$_{13}$; a guanidino which is unsubstituted or substituted in the 3-position by one or two (C$_1$–C$_7$)alkyls, a phenyl or a benzyl; a formyl; a (C$_1$–C$_7$) alkylcarbonyl; a carbamoyl substituted by R$_{14}$ and R$_{15}$; a thiocarbamoyl which is free or substituted by one or two (C$_1$–C$_7$)alkyls; a sulfamoyl substituted by R$_{16}$ and R$_{17}$; a carboxyl; a (C$_1$–C$_7$)alkoxycarbonyl; a phenoxycarbonyl; a benzyloxycarbonyl; a (C$_1$–C$_7$)alkylsulfonamido; a phenylsulfonamido in which the phenyl is unsubstituted or monosubstituted or polysubstituted by a halogen, a (C$_1$–C$_7$)alkyl, a hydroxyl, a (C$_1$–C$_7$)alkoxy, a benzyloxy or an acetoxy; a dimethylaminosulfonamido; or a 2-(4-methylphenyl)benzamido;

or R$_5$ and R$_6$, together with the phenyl to which they are bonded, form a group

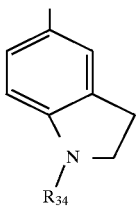

with the proviso that X is —SO$_2$—;

R$_7$ is a (C$_1$–C$_7$)alkoxycarbonyl;

R$_8$ is a (C$_1$–C$_7$)alkoxycarbonylamino; or an N-methyl-N-(C$_1$–C$_7$)alkoxycarbonylamino;

R$_9$ is a hydrogen; or a (C$_1$–C$_7$)alkyl;

R$_{10}$ is a group CR$_{18}$R$_{19}$R$_{20}$; a group (CH$_2$)$_p$R$_{35}$; a (C$_2$–C$_{10}$) alkylene substituted by R$_{21}$; a group CH$_2$CN; a group C(CH$_3$)(CH$_2$OH)$_2$ or C(CH$_2$OH)$_3$; a non-aromatic C$_3$–C$_{15}$ carbocyclic radical; a phenyl which is unsubstituted or monosubstituted or polysubstituted by a halogen, a (C$_1$–C$_7$)alkyl, a hydroxyl, a (C$_1$–C$_7$)alkoxy, a benzyloxy, an acetoxy, a nitro or an amino which is free or substituted by one or two (C$_1$–C$_7$)alkyls; a benzyl in which the phenyl is unsubstituted or monosubstituted or polysubstituted by a halogen, a (C$_1$–C7)alkyl, a hydroxyl, a (C$_1$–C$_7$)alkoxy, a benzyloxy, an acetoxy, a nitro or an amino which is free or substituted by one or two (C$_1$–C$_7$)alkyls; a phenethyl in which the phenyl is unsubstituted or monosubstituted or polysubstituted by a halogen, a (C$_1$–C$_7$)alkyl, a hydroxyl, a (C$_1$–C$_7$ )alkoxy, a benzyloxy, an acetoxy, a nitro or an amino which is free or substituted by one or two (C$_1$–C$_7$) alkyls; or a phenethyl in which the phenyl is substituted by a 3,4-methylenedioxy or a 3,4-ethylenedioxy;

R$_{11}$ is a hydrogen; a (C$_1$–C$_{12}$)alkyl; a (C$_3$–C$_7$) cycloalkylmethyl; a group OR$_{13}$; a formyl; a (C$_1$–C$_7$) alkylcarbonyl; a (C$_1$–C$_7$)alkylthiocarbonyl; a (C$_3$–C$_7$) cycloalkylcarbonyl; a (C$_3$–C$_7$)cycloalkylthiocarbonyl; a benzoyl which is unsubstituted or monosubstituted or polysubstituted by a halogen, a (C$_1$–C$_7$)alkyl, a hydroxyl, a (C$_1$–C$_7$)alkoxy, a benzyloxy or an acetoxy; a phenylacetyl in which the benzene ring is unsubstituted or monosubstituted or polysubstituted by a halogen, a (C$_1$–C$_7$)alkyl, a hydroxyl, a (C$_1$–C$_7$)alkoxy, a benzyloxy or an acetoxy; a pyridylcarbonyl; a thienylcarbonyl; a furylcarbonyl; a piperid-4-ylcarbonyl which is unsubstituted or substituted in the 1-position by a (C$_1$–C$_7$)-alkyl or by a protective group; a (C$_1$–C$_7$)alkoxycarbonyl; a phenoxycarbonyl; a phenoxythiocarbonyl; a benzyloxycarbonyl; a carbamoyl substituted by R$_{22}$ and R$_{23}$; a thiocarbamoyl substituted by R$_{22}$ and R$_{23}$; a group CH$_2$R$_{36}$; an ω-R$_{24}$(C$_1$–C$_6$)alkylcarbonyl; or ω-R$_{32}$R$_{33}$N(C$_1$–C$_4$) alkylcarbonyl;

$R_{12}$ is a morpholin-4-yl; a thiomorpholin-4-yl; an azetidin-1-yl which is unsubstituted or substituted in the 2-position by a carboxyl or substituted in the 3-position by an amino which is free or carries a protective group; a perhydroazepin-1-yl; a piperazin-1-yl which is unsubstituted or substituted in the 4-position by $R_{25}$; a piperid-1-yl which is unsubstituted or substituted by $R_{26}$; a pyrrolidin-1-yl which is unsubstituted or substituted by $R_{27}$; or a thiazolidin-3-yl which is unsubstituted or substituted by $R_{27}$;

$R_{13}$ is a hydrogen; a $(C_1-C_7)$alkyl; a benzyl; an allyl; or a tetrahydropyran-2-yl;

$R_{14}$ and $R_{15}$ are each independently hydrogen; or a $(C_1-C_7)$alkyl; $R_{15}$ can also be a $(C_1-C_7)$alkylene substituted by $R_{24}$, a cyano, a trifluoromethyl or an amino which is free or substituted by one or two $(C_1-C_7)$-alkyls; a $(C_3-C_7)$cycloalkyl; a phenyl which is unsubstituted or monosubstituted or polysubstituted by a halogen, a $(C_1-C_7)$alkyl, a hydroxyl, a $(C_1-C_7)$alkoxy or a benzyloxy; or a group $R_{28}$;

or $R_{14}$ and $R_{15}$, together with the nitrogen atom to which they are bonded, form a heterocyclic radical $R_{12}$;

$R_{16}$ and $R_{17}$ are each independently a hydrogen; or a $(C_1-C_7)$alkyl; $R_{17}$ can also be a $(C_3-C_7)$cycloalkyl; or a group $R_{28}$;

or $R_{16}$ and $R_{17}$, together with the nitrogen atom to which they are bonded, form a heterocyclic radical $R_{12}$;

$R_{18}$ is a $(C_1-C_7)$alkyl; a phenyl; a benzyl; a cyclohexylmethyl; a phenethyl; an imidazol-4-ylmethyl which is free or carries a protective group; an indol-3-yl-methyl which is free or carries a protective group; a hydroxymethyl which is free or carries a protective group; a 2-hydroxyethyl which is free or carries a protective group; a 1-hydroxyethyl which is free or carries a protective group; a 4-hydroxybenzyl which is free or carries a protective group; a mercaptomethyl which is free or carries a protective group; a 2-mercaptoethyl which is free or carries a protective group; a 2-methylthioethyl; a 2-methylsulfinylethyl; a 2-methylsulfonylethyl; a 4-aminobutyl which is free or carries a protective group; a 3-aminopropyl which is free or carries a protective group; a carboxymethyl which is free or carries a protective group; a 2-carboxyethyl which is free or carries a protective group; a carbamoylmethyl; a 2-carbamoylethyl; a 3-guanidinopropyl which is free or carries a protective group; or a non-aromatic $C_3-C_{15}$ carbocyclic radical;

$R_{19}$ is hydrogen; $R_{19}$ can also be a $(C_1-C_7)$alkyl if $R_{18}$ is a $(C_1-C7)$alkyl;

or $R_{18}$ and $R_{19}$, together with the carbon atom to which they are bonded, form a non-aromatic $C_3-C_{15}$ carbocyclic radical;

$R_{20}$ is $R_{24}$; a group $CH_2OR_{13}$; or an aminomethyl in which the amino is free or substituted by one or two $(C_1-C_7)$ alkyls or by a protective group;

$R_{21}$ is $R_{36}$; a group $OR_{37}$; a group $NR_{22}R_{33}$; a cyano; a group $S(C_1-C_7)$alkyl; a group $SO(C_1-C_7)$alkyl; or a group $S_2(C_1-C_7)$alkyl;

$R_{22}$ and $R23$ are each independently a hydrogen; or a $(C_1-C_7)$alkyl; $R_{23}$ can also be a $(C_3-C_7)$cycloalkyl; a group $CR_{18}R_{19}R_{20}$; a group $CH_2R_{24}$; a group $C(CH_3)-(CH_2OH)_2$ or $C(CH_2OH)_3$; or a $(C_2-C_6)$alkylene substituted by $R_{29}$;

or $R_{22}$ and $R_{23}$, together with the nitrogen atom to which they are bonded, form a heterocyclic radical $R_{12}$; or a cis-2,6-dimethylpiperid-1-yl;

$R_{24}$ is a carboxyl; a $(C_1-C_7)$alkoxycarbonyl; a benzyloxycarbonyl; or a carbamoyl which is free or substituted by one or two $(C_1-C_7)$alkyls;

$R_{25}$ is a $(C_1-C_7)$alkyl; a phenyl; a benzyl; a formyl; a $(C_1-C_7)$alkylcarbonyl; a $(C_1-C_7)$alkoxycarbonyl; or a benzyloxycarbonyl;

$R_{26}$ is $R_{24}$; an amino which is free or substituted by one or two $(C_1-C_7)$alkyls or by a protective group; a group $OR_{13}$; or a group $CH_2OR_{13}$;

$R_{27}$ is $R_{24}$; a group $CH_2R_{24}$; a group $CH_2OR_{13}$; or an aminomethyl in which the amino is free or substituted by one or two $(C_1-C_7)$alkyls or by a protective group;

$R_{28}$ is a group $CH(CH_2OH)_2$, $CH(CH_3)CH_2OH$, $C(CH_3)-(CH_2OH)_2$, $C(CH_3)_2CH_2OH$, $C(CH_2OH)_3$ or $CH_2CH_2OH$;

$R_{29}$ is a group $R_{24}$; a group $OR_{13}$; or a group $NR_{30}R_{31}$;

$R_{30}$ and $R_{31}$ are each independently a hydrogen; or a $(C_1-C_7)$alkyl;

or $R_{30}$ and $R_{31}$, together with the nitrogen atom to which they are bonded, form a heterocyclic radical $R_{12}$;

$R_{32}$ and $R_{33}$ are each independently a hydrogen; or a $(C_1-C_7)$alkyl; $R_{33}$ can also be an acetyl; a phenyl; a benzyl; a $(C_1-C_7)$alkoxycarbonyl; a benzyloxycarbonyl; a $(C_1-C_6)$alkylene substituted by $R_{24}$; a $(C_2-C_6)$alkylene substituted by a hydroxyl or a $(C_1-C_7)$alkoxy; or a $(C_2-C_6)$alkylene substituted by an amino which is free or substituted by one or two $(C_1-C_7)$alkyls or by a protective group;

or $R_{32}$ and $R_{33}$, together with the nitrogen atom to which they are bonded, form a heterocyclic radical $R_{12}$;

$R_{34}$ is a formyl; a $(C_1-C_7)$alkylcarbonyl; a $(C_1-C_7)$-alkoxycarbonyl; a phenoxycarbonyl; a carbamoyl substituted by two $(C_1-C_7)$alkyls; or a group $COR_{12}$;

$R_{35}$ is a piperid-4-yl which is unsubstituted or substituted in the 1-position by a $(C_1-C_7)$alkoxycarbonyl or by a $(C_1-C_7)$alkyl; or a pyrid-2-yl;

$R_{36}$ is a carboxyl; a $(C_1-C_7)$alkoxycarbonyl; a benzyloxycarbonyl; or a carbamoyl which is free or substituted by $R_{38}$ and $R_{39}$;

$R_{37}$ is $R_{13}$; a $(C_3-C_7)$cycloalkyl; a $(C_1-C_6)$alkylene substituted by R24; a $(C_2-C_6)$alkylene substituted by a hydroxyl or a $(C_1-C_7)$alkoxy; or a $(C_2-C_6)$alkylene substituted by an amino which is free or substituted by one or two $(C_1-C_7)$alkyls or by a protective group;

$R_{38}$ and $R_{39}$ are each independently a hydrogen; or a $(C_1-C_7)$alkyl; $R_{39}$ can also be a $(C_1-C_6)$alkylene substituted by $R_{24}$; a $(C_2-C_6)$alkylene substituted by a hydroxyl or a $(C_1-C_7)$alkoxy; or a $(C_2-C_6)$alkylene substituted by an amino which is free or substituted by one or two $(C_1-C_7)$alkyls or by a protective group;

X is $SO_2$; or $CH_2$;

m is 1 or, if $R_6$ is a halogen, a $(C_1-C_7)$alkyl or a $(C_1-C_7)$alkoxy, m can also be 2, 3 or 4, or else $(R_6)_m$ can be m substituents having different meanings selected from halogen; $(C_1-C_7)$alkyl; and $(C_1-C_7)$alkoxy; and p is an integer which can vary from 0 to 3; and their salts where appropriate.

Advantageously, the invention relates to the compounds of formula (I) in which:

$R_1$ and $R_2$ are each independently a hydrogen; a halogen; a $(C_1-C_7)$alkyl; a $(C_1-C_7)$alkoxy; or a trifluoromethyl;

$R_3$ is a $(C_1-C_7)$alkyl; a $(C_3-C_7)$cycloalkyl; a cyclohexyl substituted by one or two $(C_1-C_4)$alkyls; or a phenyl which is unsubstituted or monosubstituted or polysubstituted by a halogen, a $(C_1-C_7)$alkyl, a hydroxyl, a $(C_1-C_7)$alkoxy, a benzyloxy or an acetoxy;

$R_4$ is an azido; a $(C_1-C_7)$alkylsulfonamido; a phenylsulfonamido in which the phenyl is unsubstituted or monosubstituted or polysubstituted by a halogen, a $(C_1-C_7)$alkyl, a hydroxyl, a $(C_1-C_7)$alkoxy, a benzyloxy or an acetoxy; a dimethylaminosulfonamido; a group $NR_7R_8$; a group $NR_9R_{10}$; a group $NR_9R_{11}$; a heterocyclic radical $R_{12}$; a lactoylamino group; a mandeloylamino group; an N'-(1-phenylethyl)ureido group; or an N'-(1-naphth-1-ylethyl) ureido group;

$R_5$ is hydrogen or has one of the meanings given for $R_6$;

$R_6$ is a halogen; a $(C_1-C_7)$alkyl; a trifluoromethyl; a cyano; an aminomethyl in which the amino is free or substituted by one or two $(C_1-C_7)$alkyls; a nitro; a group $NR_9R_{11}$; a heterocyclic radical selected from pyrrol-1-yl, Δ3-pyrrolin-1-yl, pyrrolidin-1-yl and morpholin-4-yl; a group $OR_{13}$; a group $SR_{13}$; a guanidino which is unsubstituted or substituted in the 3-position by one or two $(C_1-C_7)$alkyls, a phenyl or a benzyl; a formyl; a $(C_1-C_7)$ alkylcarbonyl; a carbamoyl substituted by $R_{14}$ and $R_{15}$; a thiocarbamoyl which is free or substituted by one or two $(C_1-C_7)$alkyls; a sulfamoyl substituted by $R_{16}$ and $R_{17}$; a carboxyl; a $(C_1-C_7)$alkoxycarbonyl; a phenoxycarbonyl; a benzyloxycarbonyl; a $(C_1-C_7)$alkylsulfonamido; a phenylsulfonamido in which the phenyl is unsubstituted or monosubstituted or polysubstituted by a halogen, a $(C_1-C_7)$alkyl, a hydroxyl, a $(C_1-C_7)$alkoxy, a benzyloxy or an acetoxy; or a dimethylaminosulfonamido;

$R_7$ is a $(C_1-C_7)$alkoxycarbonyl;

$R_8$ is a $(C_1-C_7)$alkoxycarbonylamino; or an N-methyl-N-$(C_1-C_7)$alkoxycarbonylamino;

$R_9$ is a hydrogen; or a $(C_1-C_7)$alkyl;

$R_{10}$ is a group $CR_{18}R_{19}R_{20}$; a group $(CH_2)_rR_{21}$; a group $C(CH_3)(CH_2OH)_2$ or $C(CH_2OH)_3$; a non-aromatic $C_3-C_{15}$carbocyclic radical; a phenyl which is unsubstituted or monosubstituted or polysubstituted by a halogen, a $(C_1-C_7)$alkyl, a hydroxyl, a $(C_1-C_7)$alkoxy, a benzyloxy or an acetoxy; a benzyl in which the phenyl is unsubstituted or monosubstituted or polysubstituted by a halogen, a $(C_1-C_7)$alkyl, a hydroxyl, a $(C_1-C_7)$alkoxy, a benzyloxy or an acetoxy; or a phenethyl in which the phenyl is unsubstituted or monosubstituted or polysubstituted by a halogen, a $(C_1-C_7)$alkyl, a hydroxyl, a $(C_1-C_7)$alkoxy, a benzyloxy or an acetoxy;

$R_{11}$ is a hydrogen; a $(C_1-C_{12})$alkyl; a $(C_3-C_7)$cycloalkylmethyl; a group $OR_{13}$; a formyl; a $(C_1-C_7)$alkylcarbonyl; a $(C_1-C_7)$alkylthiocarbonyl; a $(C_3-C_7)$cycloalkylcarbonyl; a $(C_3-C_7)$cycloalkylthiocarbonyl; a benzoyl which is unsubstituted or monosubstituted or polysubstituted by a halogen, a $(C_1-C_7)$alkyl, a hydroxyl, a $(C_1-C_7)$alkoxy, a benzyloxy or an acetoxy; a phenylacetyl in which the benzene ring is unsubstituted or monosubstituted or polysubstituted by a halogen, a $(C_1-C_7)$alkyl, a hydroxyl, a $(C_1-C_7)$alkoxy, a benzyloxy or an acetoxy; a pyridylcarbonyl; a thienylcarbonyl; a furylcarbonyl; a piperid-4-ylcarbonyl which is unsubstituted or substituted in the 1-position by a $(C_1-C_7)$-alkyl or by a protective group; a $(C_1-C_7)$alkoxycarbonyl; a phenoxycarbonyl; a phenoxythiocarbonyl; a benzyloxycarbonyl; a carbamoyl substituted by $R_{22}$ and $R_{23}$; a thiocarbamoyl substituted by $R_{22}$ and $R_{23}$; a group $CH_2R_{24}$; an ω-$R_{24}(C_1-C_6)$alkylcarbonyl; or an ω-amino$(C_1-C_4)$alkylcarbonyl in which the amino is free or substituted by one or two $C_1-C_7$-alkyls or by a protective group;

$R_{12}$ is a morpholin-4-yl; a thiomorpholin-4-yl; an azetidin-1-yl which is unsubstituted, substituted in the 2-position by a carboxyl or substituted in the 3-position by an amino which is free or carries a protective group; a perhydroazepin-1-yl; a piperazin-1-yl which is unsubstituted or substituted in the 4-position by $R_{25}$; a piperid-1-yl which is unsubstituted or substituted by $R_{26}$; a pyrrolidin-1-yl which is unsubstituted or substituted by $R_{27}$; or a thiazolidin-3-yl which is unsubstituted or substituted by $R_{27}$;

$R_{13}$ is a hydrogen; a $(C_1-C_7)$alkyl; a benzyl; an allyl; or a tetrahydropyran-2-yl;

$R_{14}$ and $R_{15}$ are each independently hydrogen; or a $(C_1-C_7)$ alkyl; $R_{15}$ can also be a $(C_1-C_7)$alkyl substituted by a cyano, a trifluoromethyl or an amino which is free or substituted by one or two $(C_1-C_7)$alkyls; a $(C_3-C_7)$cycloalkyl; a phenyl which is unsubstituted or monosubstituted or polysubstituted by a halogen, a $(C_1-C_7)$alkyl, a hydroxyl, a $(C_1-C_7)$alkoxy or a benzyloxy; or a group $R_{28}$;

or $R_{14}$ and $R_{15}$, together with the nitrogen atom to which they are bonded, form a heterocyclic radical $R_{12}$;

$R_{16}$ and $R_{17}$ are each independently a hydrogen; or a $(C_1-C_7)$alkyl; $R_{17}$ can also be a $(C_3-C_7)$cycloalkyl; or a group $R_{28}$;

or $R_{16}$ and $R_{17}$, together with the nitrogen atom to which they are bonded, form a heterocyclic radical $R_{12}$;

$R_{18}$ is a $(C_1-C_7)$alkyl; a phenyl; a benzyl; a cyclohexylmethyl; a phenethyl; an imidazol-4-ylmethyl which is free or carries a protective group; an indol-3-yl-methyl which is free or carries a protective group; a hydroxymethyl which is free or carries a protective group; a 2-hydroxyethyl which is free or carries a protective group; a 1-hydroxyethyl which is free or carries a protective group; a 4-hydroxybenzyl which is free or carries a protective group; a mercaptomethyl which is free or carries a protective group; a 2-mercaptoethyl which is free or carries a protective group; a 2-methylthioethyl; a 2-methylsulfinylethyl; a 2-methylsulfonylethyl; a 4-aminobutyl which is free or carries a protective group; a 3-aminopropyl which is free or carries a protective group; a carboxymethyl which is free or carries a protective group; a 2-carboxyethyl which is free or carries a protective group; a carbamoylmethyl; a 2-carbamoylethyl; a 3-guanidinopropyl which is free or carries a protective group; or a non-aromatic $C_3-C_{15}$ carbocyclic radical;

$R_{19}$ is hydrogen; $R_{19}$ can also be a $(C_1-C_7)$alkyl if $R_{18}$ is a $(C_1-C_7)$alkyl;

or $R_{18}$ and $R_{19}$, together with the carbon atom to which they are bonded, form a non-aromatic $C_3-C_{15}$ carbocycle;

$R_{20}$ is $R_{24}$; a group $CH_2OR_{13}$; or an aminomethyl in which the amino is free or substituted by one or two $(C_1-C_7)$alkyls or by a protective group;

$R_{21}$ is $R_{24}$; a group $OR_{13}$; a group $NR_{32}R_{33}$; or a cyano;

$R_{22}$ and $R_{23}$ are each independently a hydrogen; or a $(C_1-C_7)$alkyl; $R_{23}$ can also be a $(C_3-C_7)$cycloalkyl; a $(C_2-C_3)$alkylene substituted by $R_{29}$; a group $CR_{18}R_{19}R_{20}$; a group $CH_2R_{24}$; or a group $C(CH_3)(CH_2OH)_2$ or $C(CH_2OH)_3$;

or $R_{22}$ and $R_{23}$, together with the nitrogen atom to which they are bonded, form a heterocyclic radical $R_{12}$; or a cis-2,6-dimethylpiperid-1-yl;

$R_{24}$ is a carboxyl; a $(C_1-C_7)$alkoxycarbonyl; a benzyloxycarbonyl; or a carbamoyl which is free or substituted by one or two $(C_1-C_7)$alkyls;

$R_{25}$ is a $(C_1-C_7)$alkyl; a phenyl; a benzyl; a formyl; a $(C_1-C_6)$alkylcarbonyl; a $(C_1-C_7)$alkoxycarbonyl; or a benzyloxycarbonyl;

$R_{26}$ is $R_{24}$; an amino which is free or substituted by one or two $(C_1-C_7)$alkyls or by a protective group; a group $OR_{13}$; or a group $CH_2R_{13}$;

$R_{27}$ is $R_{24}$; a group $CH_2R_{24}$; a group $CH_2OR_{13}$; or an aminomethyl in which the amino is free or substituted by one or two $(C_1-C_7)$alkyls or by a protective group;

$R_{28}$ is a group $CH(CH_2OH)_2$, $CH(CH_3)CH_2OH$, $C(CH_3)$—$(CH_2OH)_2$, $C(CH_3)_2CH_2OH$, $C(CH_2OH)_3$ or $CH_2CH_2OH$;

$R_{29}$ is a group $R_{24}$; a group $OR_{13}$; or a group $NR_{30}R_{31}$;

$R_{30}$ and $R_{31}$ are each independently a hydrogen; or a $(C_1-C_7)$alkyl;

or $R_{30}$ and $R_{31}$, together with the nitrogen atom to which they are bonded, form a heterocyclic radical $R_{12}$;

$R_{32}$ and $R_{33}$ are each independently a hydrogen; or a $(C_1-C_7)$alkyl; $R_{33}$ can also be an acetyl; a phenyl; a benzyl; or a $C_2-C_3$-alkylene substituted by a group $OR_{13}$ or an amino which is free or substituted by one or two $(C_1-C_7)$alkyls or by a protective group;

or $R_{32}$ and $R_{33}$, together with the nitrogen atom to which they are bonded, form a heterocyclic radical $R_{12}$;

X is $SO_2$; or $CH_2$;

m is 1 or, if $R_6$ is a halogen, a $(C_1-C_7)$alkyl or a $(C_1-C_7)$ alkoxy, m can also be 2, 3 or 4, or else $(R_6)_m$ can be m substituents having different meanings selected from halogen; $(C_1-C_7)$alkyl; and $(C_1-C7)$alkoxy; and t is an integer which can vary from 2 to 10; and their salts where appropriate.

If a compound according to the invention has one or more asymmetric carbons, the invention includes all the optical isomers of this compound.

The salts of the compounds of formula (I) according to the present invention include those with mineral or organic acids which permit a suitable separation or crystallization of the compounds of formula (I), such as picric acid, oxalic acid or an optically active acid, for example a mandelic acid or a camphosulfonic acid, and mineral or organic acids which form physiologically acceptable salts such as the hydrochloride, hydrobromide, sulfate, hydrogensulfate, dihydrogenphosphate, maleate, fumarate, naphthalene-2-sulfonate and paratoluenesulfonate.

The salts of the compounds of formula (I) also include those with organic or mineral bases, for example the salts of alkali metals or alkaline earth metals, such as the sodium, potassium and calcium salts, the sodium and potassium salts being preferred, or with an amine such as trometamol, or else those with arginine, lysine or any physiologically acceptable amine.

According to the present invention, halogen is understood as meaning an atom selected from fluorine, chlorine, bromine and iodine, preferably fluorine or chlorine.

Protective groups for amine, hydroxyl, thiol or carboxyl groups are understood as meaning protective groups such as those described in Protective Groups in Organic Synthesis, T. W. Greene and P. G. M. Wutts, published by John Wiley and Sons, 1991, and in Protective Groups in Organic Chemistry, J. F. W. McOmie, published by Plenum Press, 1973.

According to the present invention, $C_1-C_7$-, $C_1-C_4$-, $C_1-C_6$-, $C_2-C_6$-, $C_1-C_{12}$- or $C_2-C_{10}$-alkyl is understood as meaning a linear or branched $C_1-C_7$-, $C_1-C_4$-, $C_1-C_6$-, $C_2-C_6$-, $C_1-C_{12}$- or $C_2-C_{10}$-alkyl.

The non-aromatic $C_3-C_{15}$ carbocyclic radicals include saturated or unsaturated, fused or bridged, monocyclic or polycyclic radicals, possibly terpene radicals. These radicals are optionally monosubstituted or polysubstituted by a $C_1-C_4$-alkyl. The monocyclic radicals include cycloalkyls, for example cyclopropyl, cyclopentyl, cyclohexyl, cycloheptyl, cyclo-octyl and cyclododecyl. The polycyclic radicals include for example norbornane and adamantane.

In the group $CR_{18}R_{19}R_{20}$, if $R_{18}$ and $R_{19}$, together with the carbon atom to which they are bonded, form a non-aromatic $C_3-C_{15}$ carbocycle, said carbocycle is as defined for the corresponding radicals above.

The compounds of formula (I) in which $R_1$ is in the 5-position of the indol-2-one and $R_2$ is in the 6-position or is hydrogen are preferred compounds.

The compounds of formula (I) in which $R_1$ is a chlorine atom or an ethoxy group in the 5-position of the indol-2-one and $R_2$ is hydrogen or a chlorine atom or a methyl group in the 6-position are preferred compounds.

The compounds of formula (I) in which $R_3$ is a chlorophenyl, a methoxyphenyl or a cyclohexyl are preferred compounds.

The compounds of formula (I) in which $R_4$ is an amino group, a $(C_1-C_{12})$alkylamino, a piperazin-1-yl substituted in the 4-position by a $(C_2-C_{10})$alkyl group substituted by an amino, a group $N(R_9)(CH_2)_pR_{35}$, a group $N(R_9)(C_2-C_{10})$alkyl-$R_{21}$ or a group $N(R_9)CO(C_1-C_4)$alkyl-$NR_{32}R_{33}$ are preferred compounds.

The compounds of formula (I) in which $R_5$ is either hydrogen or a methoxy group in the 2-position and $R_6$ in the 4-position is a benzamido which is unsubstituted or substituted by a methoxy, a carbamoyl substituted by $R_{14}$ and $R_{15}$, or a $C_1-C_7$-dialkylureido, or $R_5$ and $R_6$ together with the phenyl to which they are bonded, form a group

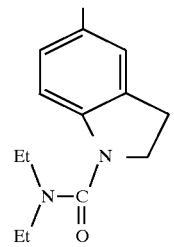

with the proviso that X is —$SO_2$—, are preferred compounds.

Very particularly preferred compounds are those of the formula

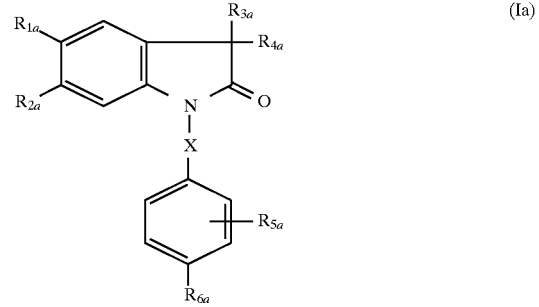

(Ia)

in which:

$R_{1a}$ is an ethoxy or a chlorine;

$R_{2a}$ is hydrogen, a chlorine or a methyl group;

$R_{3a}$ is a chlorophenyl, a methoxyphenyl or a cyclohexyl;

$R_{4a}$ is an amino; a $(C_1-C_{12})$alkylamino; a piperazin-1-yl radical substituted in the 4-position by a $(C_2-C_{10})$-alkylene group substituted by an amino; a group $N(R_9)$—$(CH_2)_pR_{35}$; a group $N(R_9)(C_2-C_{10})$alkyl-$R_{21}$; or a group $N(R_9)CO(C_1-C_4)$alkyl-$NR_{32}R_{33}$;

$R_{5a}$ is hydrogen or a 2-methoxy;

$R_{6a}$ is a benzamido in which the phenyl is unsubstituted or substituted by a methoxy; a group $CONR_{14}R_{15}$; or an N',N'-di$(C_1-C_7)$alkylureido group;

or $R_{5a}$ and $R_{6a}$ together with the phenyl to which they are bonded, form a group

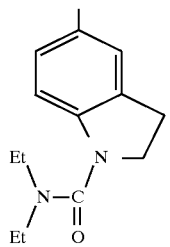

with the proviso that X is $SO_2$; and
the substituents X, $R_9$, $R_{14}$, $R_{15}$, $R_{21}$, $R_{32}$, $R_{33}$ and $R_{35}$ are as defined above for the compounds of formula (I); and their salts.

The following abbreviations are used in the description and in the Examples:

DCM: dichloromethane
Ether: diethyl ether
Iso ether: diisopropyl ether
$CCl_4$: carbon tetrachloride
MeOH: methanol
EtOH: ethanol
AcOEt: ethyl acetate
DMF: dimethylformamide
THF: tetrahydrofuran
DIPEA: diisopropylethylamine
$NEt_3$: triethylamine
DBU: 1,8-diazabicyclo[5.4.0]undec-7-ene
AcOH: acetic acid
HCl: hydrochloric acid
TFA: trifluoroacetic acid
NaCl: sodium chloride
Boc: tert-butoxycarbonyl
$(Boc)_2O$: di-tert-butyl dicarbonate
Z: benzyloxycarbonyl
Bz: benzyl
Me, OMe: methyl, methoxy
Et, OEt: ethyl, ethoxy Pr, iPr: n-propyl, isopropyl
Bu, iBu, tBu: butyl, isobutyl, tert-butyl
Ms: mesyl
BOP: benzotriazol-1-yloxytris(dimethylaminophosphonium) hexafluorophosphate
Lawesson's reagent: 2,4-bis(4-methoxyphenyl)-1,3-dithia-2,4-diphosphetane 2,4-disulfide
Silica H: 60H silica gel marketed by MERCK (DARMSTADT)
M.p.: melting point
RT: room temperature
NMR: nuclear magnetic resonance
s: singlet
bs: broad singlet
d: doublet
t: triplet
qd: quadruplet
m: unresolved signals
mt: multiplet
t of d: triplet of doublets
d of d: doublet of doublets
sep: septuplet The present invention further relates to a method of preparing the compounds according to the invention, which comprises:

1) reacting a halide of the formula

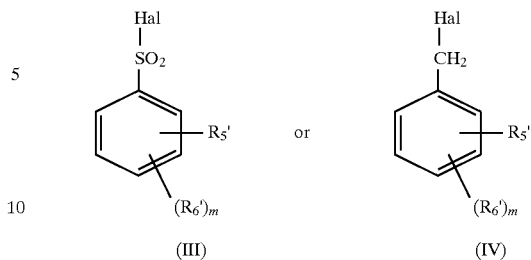

in which Hal is a halogen atom, preferably chlorine or bromine, and $R'_5$ and $R'_6$ are respectively either $R_5$ and $R_6$ as defined above for (I), or precursor groups of $R_5$ and $R_6$, with a compound of the formula

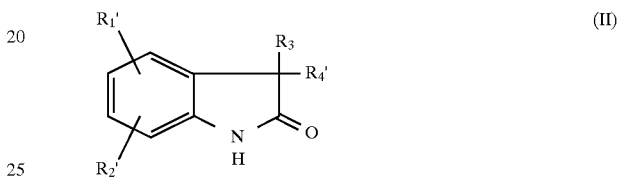

in which $R'_1$, $R'_2$ and $R'_4$ are respectively either $R_1$, $R_2$ and $R_4$ as defined for (I), or precursor groups of $R_1$, $R_2$ and $R_4$, and $R_3$ is as defined for (I); and 2) either, if $R'_1=R_1$, $R'_2=R'_2$, $R_4=R_4$, $R'_5=R_5$ and $R'_6=R_6$, isolating the resulting compound of formula (I);

3) or, if any one of the groups $R'_1$, $R'_2$, $R'_4$, $R'_5$ and/or $R'_6$ is respectively a precursor group of $R_1$, $R_2$, $R_4$, R5 and/or $R_6$, subjecting the compound obtained in step 1) to a subsequent treatment in order to prepare the compound of formula (I) by converting any one of the groups $R'_1$, $R'_2$, $R'_4$, $R'_5$ and/or $R'_6$ to $R_1$, $R_2$, $R_4$, $R_5$ and/or $R_6$ respectively; and 4) if appropriate, converting the compound obtained in step 2) or step 3) to one of its salts.

A compound carrying a substituent $R'_1$, $R'_2$, $R'_4$, $R'_5$ and/or $R'_6$, which are precursors of $R_1$, $R_2$, $R_4$, $R_5$ and/or $R_6$, is called a compound (I').

The reaction of step 1) is carried out in an anhydrous solvent such as DMF or THF, in the presence of a metal hydride such as, for example, sodium hydride, or in the presence of an alcoholate such as potassium tert-butylate. 1,3-Dihydroindol-2-one derivatives of formula (II) can be prepared by the methods described in patents ZA 83 09532 and 85 04765 and patent GB 1 125 671.

1,3-Dihydroindol-2-one derivatives substituted in the 3-position by nitrogen-containing groups can also be prepared by methods well known to those skilled in the art, such as those described in the following publications:

Farm. Zh. (Kiev), 1976, 5, 30–33.
Khim-Farm. Zh., 1979, 13 (11), 45–49.
J. Pharm. Sci., 1975, 64 (4), 639–642.
Chem. Pharm. Bull., 1978, 26 (9), 2866–2873.
J. Org. Chem., 1964, 29, 1206.

More particularly, the 1,3-dihydroindol-2-ones (II) can be obtained by reacting a 3-halogeno-1,3-dihydroindol-2-one compound of the formula

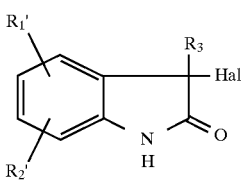

(V)

with a compound of the formula

H—R'₄   (VI)

in which formulae R'₁, R'₂, R₃ and R'₄ are as defined above and Hal is a halogen, preferably chlorine or bromine. The reaction can be carried out in the presence of a base such as DIPEA or triethylamine, which behaves as an acid acceptor, or by using an excess of the compound (VI).

The 3-halogeno-1,3-dihydroindol-2-ones (V) are obtained by any one of the various methods described in the literature.

For example, a compound of the formula

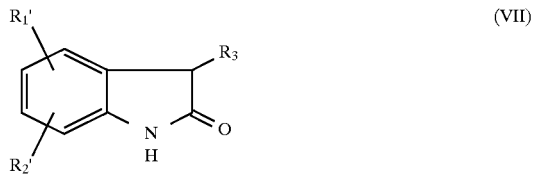

(VII)

in which R'₁, R'₂ and R₃ are as defined above, is converted directly to a 3-halogeno-1,3-dihydroindol-2-one compound (V) by means of a halogenating agent such as bromine (by the method described in Farm. Zh. (Kiev), 1976, 5, 30–33) or such as N-chlorosuccinimide in a solvent like CCl₄.

The compounds of formula (VII) are prepared according to J. Org. Chem., 1968, 33 (4), 1640–1643. In particular, a compound of formula (VII) in which R₃ is an unsubstituted or substituted cyclohexylmethyl or benzyl can be prepared according to J. Med. Chem., 1965, 8, 626–637.

According to another example of the preparation of the compounds of formula (V), an isatin derivative of the formula

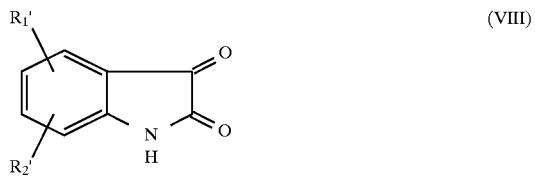

(VIII)

is reacted with a compound of the formula (IX) R₃M or R₃MgBr   (X)

in which formulae R'₁, R'₂ and R₃ are as defined above and M is a reactive metal substituent such as lithium, under anhydrous conditions, the intermediate obtained is hydrolyzed to give a 3-hydroxy-1,3-dihydroindol-2-one compound of the formula

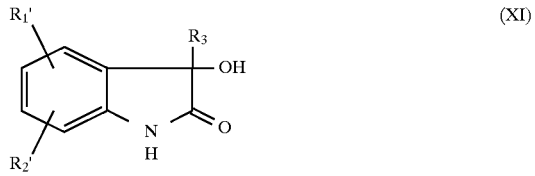

(XI)

and the latter compound is then converted to the corresponding 3-halogeno-1,3-dihydroindol-2-one compound (V) by reaction with thionyl chloride or a similar halogenating agent.

It is also possible to prepare a compound of formula (XI) by oxidizing a compound of formula (VII) with air in the presence of a base such as sodium hydride, and in the presence of dimethyl disulfide.

According to another method of preparing the compounds of formula (II), a compound of formula (XI) is reacted with methanesulfonyl chloride in the presence of a base such as, for example, triethylamine, in an anhydrous solvent such as THF; the resulting mesylate is converted to the 1,3-dihydroindol-2-one of formula (II) by reaction with a compound of formula (VI).

Preferably, to prepare a compound of formula (II) in which R'₄ is azido, sodium azide is reacted with a compound (V); the reaction is carried out in acetonitrile under reflux or according to the method described by Y. Tamura et al. in Chem. Pharm. Bull., 1978, 26 (9), 2866–2873.

A compound of formula (II) in which R'₄ is an amino can be prepared by reacting a compound of formula (II) in which R'₄ is azido with propane-1,3-dithiol in the presence of a base such as triethylamine, according to the method described by H. Bayley et al. in Tetrahedron Letters, 1978, 39, 3633–3634.

This method is particularly preferred for the preparation of a compound of formula (II) in which R'₄ is an amino and R'₁ in the 5-position is a (C₁–C₇)-alkoxy.

A compound (II) in which R'₄ is a group NR₇R₈ is prepared by reacting a compound of the formula

R₇—N=R₈   (XII)

i.e.:

AlkOOC—N=N—COOAlk in which Alk is a (C₁–C₇)alkyl, with a compound (VII); the reaction is carried out in an anhydrous solvent such as THF, in the presence of a base such as lithium diisopropylamide.

A compound of formula (II) in which R'₄ is an amino acid residue (R'₄=N(R₉)CR₁₈R₁₉R₂₀) is prepared by reacting an amino acid or a derivative thereof, optionally protected by the protective groups conventionally used in peptide synthesis, of the formula $$\begin{array}{c} R_9 \\ | \\ H-NCR_{18}R_{19}R_{20} \end{array}$$   (XIII)

with a compound (V).

The amino acids which are not commercially available are prepared according to the synthesis of Strecker, Ann., 1850, 75, 27, or according to the synthesis of H. T. Bucherer et al., J. Pract. Chem., 1934, 141, 5, followed by hydrolysis to give the amino acids; for example, 2-aminoadamantane-2-carboxylic acid is prepared according to H. T. Nagasawa et al., J. Med. Chem., 1973, 16 (7), 823.

α-Amino-1-adamantylacetic and α-amino-2-adamantylacetic acids are prepared according to B. Gaspert et al., Croatica Chemica Acta, 1976, 48 (2), 169–178.

2-Aminonorbornane-2-carboxylic acid is prepared according to H. S. Tager et al., J. Am. Chem. Soc., 1972, 94, 968.

α-Aminocycloalkylcarboxylic acids are prepared according to J. W. Tsang et al., J. Med. Chem., 1984, 27, 1663.

R- and S-cyclopentylglycines are prepared according to European patent application EP 477 049.

R- and S-cyclohexylglycines are prepared according to Rudman et al., J. Am. Chem. Soc., 1952, 74, 551.

R- and S-cyclohexylglycines can also be prepared by the catalytic hydrogenation of R- and S-phenylglycines.

α-Aminocycloalkylcarboxylic acids having the R or S configuration can also be prepared by stereospecific enzymic hydrolysis of the corresponding racemic N-acetylated derivatives according to J. Hill et al., J. Org. Chem., 1965, 1321.

A compound of formula (II) in which R'$_4$ is a group N(R$_9$)(CH$_2$)$_p$R$_{35}$ is prepared by reacting a compound of the formula

(XV)

with a compound (V).

The compounds of formula (XV) are known or are prepared by known methods. For example, the compounds of formula (XV) in which R$_{35}$ is a piperid-4-yl substituted in the 1-position by a Boc are prepared according to Prugh J. D. et al., Synthetic Communications, 1992, 22, 16, 2357–2360, if p=1; if p=2 or 3, the method described in J. Med. Chem., 1989, 32, 391–396, or the method described in Scheme 1, is applied.

Scheme 1

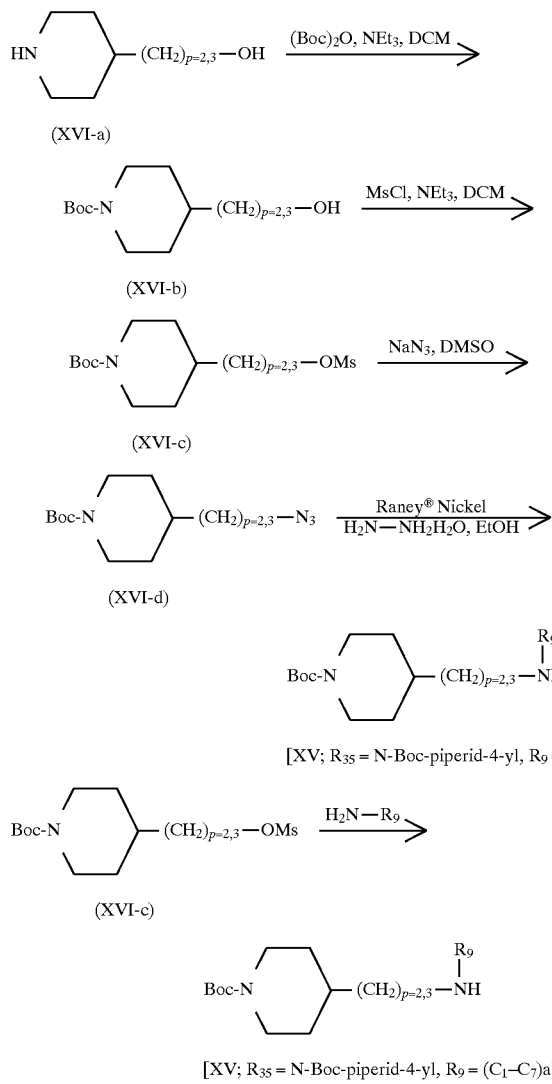

A compound of formula (II) in which R'$_4$ is a group N(R$_9$)CH$_2$R$_{36}$ in which R$_{36}$ is a (C$_1$–C$_7$)alkoxycarbonyl or a benzyloxycarbonyl is prepared by reacting a compound of the formula

(XVII)

in which R$_{36}$ is a (C$_1$–C$_7$)alkoxycarbonyl or, respectively, a benzyloxycarbonyl with a compound (V). By known methods, such a compound is used to prepare a compound of formula (II) in which R'$_4$ is a group N(R$_9$)CH$_2$COOH, which, by reaction with a compound of the formula HNR$_{38}$R$_{39}$ according to the appropriate techniques of amide coupling, makes it possible to obtain a compound of formula (II) in which R'$_4$ is a group N(R$_9$)CH$_2$CONR$_{38}$R$_{39}$.

The same methods described above are used to prepare the compounds of formula (II) in which R'$_4$ is a group N(R$_9$)—(C$_2$–C$_{10}$)alkyl-R$_{36}$ in which R$_{36}$ is a (C$_1$–C$_7$) alkoxycarbonyl, a benzyloxycarbonyl or a carbamoyl substituted by R$_{38}$ and R$_{39}$.

A compound of formula (II) in which R'$_4$ is a group N(R$_9$)(C$_2$–C$_{10}$)alkyl-OR$_{37}$ is prepared by reacting a compound of the formula

(XVIII)

with a compound (V).

The compounds of formula (XVIII) are known or are prepared by known methods.

A compound of formula (II) in which R'$_4$ is a group N(R$_9$)(C$_2$–C$_{10}$)alkyl-NR$_{32}$R$_{33}$ is prepared by reacting a compound of the formula

(XIX)

with a compound (V).

The compounds of formula (XIX) are known or are prepared by known methods. For example, the compounds of formula (XIX) are prepared according to the methods described in J. Med. Chem., 1989, 32, 391–396, in Synthesis, 1982, 404–405, in J. Am. Chem. Soc., 1946, 68, 10–14, or in patent EP-0429344. The compounds of formula (XIX) in which R$_{33}$ is other than a protective group can also be prepared by following the different steps of the method described in Scheme 2.

Scheme 2

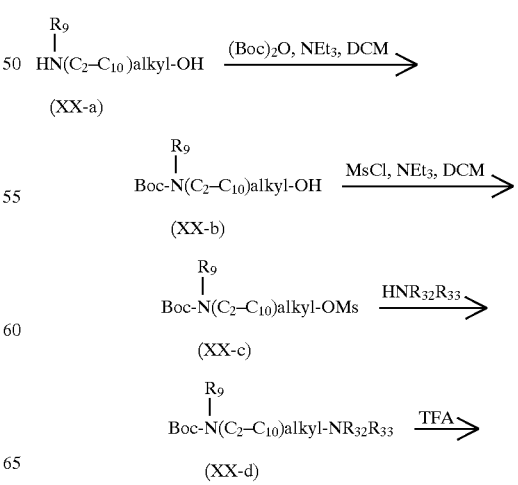

-continued
Scheme 2

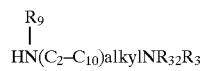

[XIX; $R_{33}$ other than a protecting group]

To prepare a compound of formula (II) in which $R'_4$ is a group $N(R_9)(C_2-C_{10})$alkyl-$S(C_1-C_7)$alkyl, a compound of the formula

 (XVIII')

is reacted with a compound (V). The compounds of formula (XVIII') are known or are prepared by known methods. The compounds of formula (II) in which $R'_4$ is a group $N(R_9)$ $(C_2-C_{10})$alkyl-$SO(C_1-C_7)$alkyl or a group $N(R_9)(C_2-C_{10})$ alkyl-$SO_2(C_1-C_7)$alkyl are prepared, according to methods known to those skilled in the art, from the compounds of formula (II) in which $R'_4$ is a group $N(R_9)(C_2-C_{10})$alkyl-S $(C_1-C_7)$alkyl.

Compounds of formula (II) in which $R'_4$ is a $(C_1-C_7)$ alkylamino or a $(C_1-C_{12})$alkylamino can also be prepared by reacting a compound of formula (II) in which $R'_4$ is an amino group with an aldehyde or a ketone in an acid medium, in the presence of a reducing agent such as sodium cyanoborohydride; an identical reaction is used to prepare the compounds of formula (II) in which $R'_4$ is a dialkylamino in which the alkyls are identical or different, one of the alkyls being $C_1-C_7$ and the other $C_1-C_{12}$.

The compounds of formula (II) in which $R'_4$ is an amino group substituted by an optionally substituted benzyl can also be prepared by reacting an optionally substituted benzyl chloride with a compound of formula (II) in which $R'_4$ is an amino group or an alkylamino group in which the alkyl is $C_1-C_7$.

To prepare the compounds of formula (II) in which $R'_4$ is an amino group substituted by a cycloalkylmethyl in which the cycloalkyl is $C_3-C_7$ or an optionally substituted phenethyl, it is also possible to react a compound of formula (II) in which $R'_4$ is an amino group with a cycloalkylcarboxaldehyde in which the cycloalkyl is $C_3-C_7$ or, respectively, an optionally substituted phenylacetaldehyde in an acid medium, in the presence of a reducing agent such as sodium cyanoborohydride.

A compound of formula (II) in which $R'_4$ is a group $\omega$-$R_{32}R_{33}N(C_1-C_4)$alkylCON($R_9$)— is prepared by reacting a halogeno($C_1-C_4$)alkylcarbonyl halide such as bromoacetyl bromide, 3-chloropropionyl chloride, 4-chlorobutyryl chloride or 5-chlorovaleryl chloride, for example, with a compound of formula (II) in which $R'_4$ is a group $R_9$NH—; then, reaction of the resulting intermediate with a compound $HNR_{32}R_{33}$ gives the compound of formula (II) designated above. In particular, reaction of a compound of formula (II) in which $R'_4$ is a group $R_9$NH— with acryloyl chloride in the presence of a base such as pyridine, followed by reaction of the resulting intermediate with a compound $HNR_{32}R_{33}$, gives a compound of formula (II) in which $R'_4$ is a group $N(R_9)COCH_2CH_2NR_{32}R_{33}$.

Some of the compounds of formula (VII) and some of the compounds of formula (V) are novel and form a further subject of the present invention.

Thus the compounds of the formula

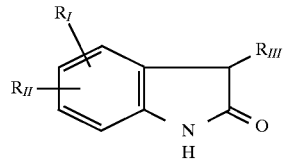 (VII')

and the compounds of the formula

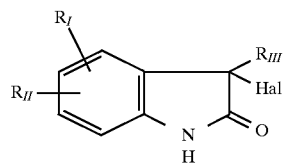 (V')

in which:

$R_I$ and $R_{II}$ are each independently a hydrogen, a halogen, a $(C_1-C_7)$alkyl, a $(C_1-C_7)$alkoxy, a trifluoromethyl, a nitro, an amino, a hydroxyl or a benzyloxy;
$R_{III}$ is a phenyl monosubstituted or polysubstituted by a halogen, a $(C_1-C_7)$alkyl, a hydroxyl, a $(C_1-C_7)$-alkoxy, a benzyloxy or an acetoxy; and
Hal is a halogen, are novel and form part of the invention.

Likewise, some of the compounds of formula (II) are novel and form a subject of the present invention.

Thus the compounds of the formula

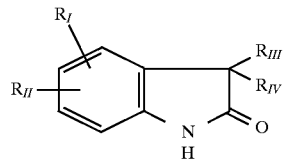 (II')

in which:

$R_I$, $R_{II}$ and $R_{III}$ are as defined above for (V') and (VII');
$R_{IV}$ is an azido, an amino, a 2,2-dimethylhydrazino group, a group $NR_7R_8$, a group $NR_9R_{10}$ or $NR_9R_{XI}$, a heterocyclic radical $R_{12}$ or a piperazin-1-yl radical substituted in the 4-position by a $(C_2-C_{10})$alkylene group substituted by an amino group which is free or carries a protective group;
$R_{XI}$ is a $(C_1-C_{12})$alkyl, a $(C_3-C_7)$cycloalkylmethyl, a group $OR_{13}$, a group $CH_2R_{36}$ or a group $\omega$-$R_{32}R_{33}N(C_1-C_4)$-alkylcarbonyl; and
$R_8$, $R_9$, $R_{10}$, $R_{12}$, $R_{13}$, $R_{32}$, $R_{33}$ and $R_{36}$ are as defined above for (I), are novel and form part of the invention.

The benzenesulfonyl halides (III) are prepared by known methods.

Thus, for example, 4-dimethylaminobenzenesulfonyl chloride is prepared according to C. N. Sukenik et al., J. Amer. Chem. Soc., 1977, 99, 851–858. More generally, the benzenesulfonyl halides (III) substituted by a dimethylamino group are known or are prepared by known methods; p-benzyloxybenzenesulfonyl chloride is prepared according to European patent application EP 229 566.

The alkoxybenzenesulfonyl chloride is prepared from the sodium alkoxybenzenesulfonate, which is itself prepared by reacting an alkyl halide with sodium hydroxybenzenesulfonate.

2,4-Dimethoxybenzenesulfonyl chloride is prepared according to J. Am. Chem. Soc., 1952, 74, 2008.

The benzenesulfonyl halides of the formula

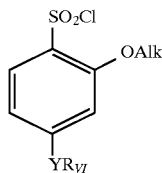

(III')

in which:

Alk is a $(C_1-C_7)$alkyl;
Y is O or S; and
$R_{VI}$ is a $(C_1-C_7)$alkyl, an allyl or a benzyl, are prepared according to D. Hofmann et al. in Liebigs Ann. Chem., 1982, 287–297.

Trimethylsilyl chlorosulfonate is reacted with benzene compounds carrying the substituents $YR_{VI}$ and OAlk in the 1,3-position, in a solvent such as DCM, at RT. This is followed by application of the method of R. Passerini et al. in Gazz. Chim. Ital., 1960, 90, 1277–89, and then by neutralization, for example with alkali metal carbonate, after which the product is reacted with a halide, such as $POCl_3$, to give the desired benzenesulfonyl halide.

The benzenesulfonyl halides (III) substituted by a $(C_1-C_7)$alkoxycarbonyl, a phenoxycarbonyl, a benzyloxycarbonyl, a $(C_1-C_7)$alkylthio or a benzylthio are prepared according to Col. Czechoslov. Chem. Commun., 1984, 49, 1184, from an aniline derivative substituted by the same group, said aniline derivative itself being obtained from the corresponding nitro derivative.

The nitrobenzoic acid derivatives are known; an appropriate esterification reaction with this acid gives the corresponding alkyl and phenyl esters.

The benzenedisulfonyl dihalides (III, $R'_6$=$SO_2$Hal) are known or are prepared by known methods. For example, 2,4.dimethoxybenzene-1,5-disulfonyl dichloride is described by R. J. W. Cremlyn in J. Chem. Soc. C, 1969, 1341–1345.

The benzenesulfonyl halides (III) in which $R'_6$ in the 4-position is a sulfamoyl substituted by $R_{16}$ and $R_{17}$ ($R'_6$=$SO_2NR_{16}R_{17}$) and $R'_5$ in the 2-position is a $(C_1-C_7)$ alkoxy can be prepared by the following method: 3-Alkoxy-4-nitrobenzenesulfonyl halides are prepared by reacting chlorosulfonic acid with 2-alkoxynitrobenzene compounds and the resulting sulfonyl chloride is reacted with compounds $HNR_{16}R_{17}$. The corresponding benzenesulfonyl halides are obtained according to Col. Czechoslov. Chem. Commun., 1984, 49, 1184, from the aniline derivatives substituted by the same group, said aniline derivatives themselves being obtained from the corresponding nitro derivatives.

The benzenesulfonyl halide (III) in which $R'_6$ in the 4-position is an N',N'-diethylureido group [$R'_6$=NHCON(Et)$_2$] can be prepared by reacting chlorosulfonic acid with N',N'-diethyl-N-phenylurea, which is itself obtained by reacting aniline with diethylcarbamoyl chloride.

4-(Morpholin-4-yl)benzenesulfonyl chloride is prepared according to the method described in Arzneim.-Forsch./Drug Res., 1994, 44 (I), no. 4, 501–509.

The benzenesulfonyl halide of formula (III) in which $R'_5$ and $R'_6$, together with the phenyl to which they are bonded, form a group

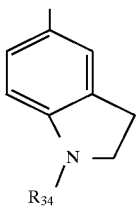

is prepared by reacting chlorosulfonic acid with a compound of the formula

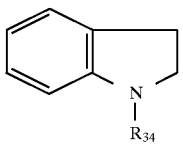

(XXI)

in which $R_{34}$ is as defined for (I).

The compounds of formula (XXI) in which $R_{34}$ is a formyl or a $(C_1-C_7)$alkylcarbonyl are obtained by reacting formic acid in acetic anhydride or, respectively, by reacting an appropriate anhydride or an appropriate acid chloride, in the presence of an amine such as triethylamine, with indoline. Likewise, reaction of a $C_1-C_7$-alkyl or phenyl chloroformate with indoline in the presence of a base such as pyridine gives the compounds of formula (XXI) in which $R_{34}$ is a $(C_1-C_7)$alkoxycarbonyl or a phenoxycarbonyl.

Reaction of a carbamoyl chloride substituted by two $(C_1-C_7)$alkyls with indoline in the presence of a base such as pyridine gives the compounds of formula (XXI) in which $R_{34}$ is a carbamoyl substituted by two $(C_1-C_7)$alkyls.

Reaction of a compound $R_{12}H$ with a compound of formula (XXI) in which $R_{34}$ is a phenoxycarbonyl gives a compound of formula (XXI) in which $R_{34}$ is a group $COR_{12}$.

The benzyl halides of formula (IV) are known or are prepared by known methods.

By way of example, publications may be cited which describe the following halogenomethylbenzene derivatives:
1,2,4- 4,2,1- or 2,4,1-(chloromethyl),(methyl), (methoxy) benzene : Bull. Soc. Chim. France, 1937, 4, 1092.
2-chloromethyl-1,3-dimethoxybenzene: Chem. Listy, 1953, 47, 601–612.
1-bromomethyl-2-methoxy-4-nitrobenzene: Sci. Sinica (Peking), 1962, 11, 483–498.
1-bromomethyl-2-methyl-4-nitrobenzene: Pharmazie, 1969, 24 (1), 29–32.
1-bromomethyl-2-methoxy-4-nitrobenzene: Bull. Soc. Chim. France, 1962, 2255.
1-bromomethyl-4-methoxy-2-nitrobenzene: Zh. Obshch. Khim., 1963, 33 (8), 2792–2793.
methyl 4-bromomethyl-3-methoxybenzoate: European patent application EP 179 619.
ethyl 2-bromomethyl-6-methoxybenzoate: J. Org. Chem., 1983, 48, 3439–3444.
ethyl 2-bromomethyl-4,5-dimethoxybenzoate and ethyl 2-bromomethyl-3,4-dimethoxybenzoate: J. Org. Chem., 1968, 33, 494.
methyl 4-bromomethyl-2-methoxybenzoate: Bull. Soc. Chim. France, 1962, 2255.
1-bromomethyl-4-cyano-2-methoxybenzene and 4-aminomethyl-1-bromomethyl-2-methoxybenzene: J. Med. Chem., 1990, 33, 2437–2451.

In general, the halogenomethylbenzene derivatives can be prepared by reacting N-bromosuccinimide with the corresponding methylbenzene derivatives. The reaction is carried out in a solvent such as carbon tetrachloride, in the presence of dibenzoyl peroxide. It is also possible to prepare a halogenomethylbenzene derivative from a corresponding hydroxymethylbenzene derivative by reaction with phosphorus tribromide in ether.

According to another method, the halogenomethylbenzene derivatives of formula (IV) can be prepared from the corresponding alcohol by reaction with thionyl chloride to give a methylbenzene chloride.

For certain meanings of the substituents $R_1$, $R_2$, $R_4$, $R_6$ and/or $R_5$, the compounds (I) according to the invention can be prepared from a precursor of formula (I') substituted by a group $R'_1$, $R'_2$, $R'_4$, $R'_6$ and/or $R'_5$, called a precursor group of $R_1$, $R_2$, $R_4$, $R_6$ and/or $R_5$, using methods known to those skilled in the art.

The following description relates to the preparation of the compounds of formula (I) carrying substituents $R_1$, $R_4$ and/or $R_6$; the same methods are applied to the preparation of the compounds in which the substituents $R_2$ and/or $R_5$ have the meanings indicated for $R_1$ and/or $R_6$.

The compounds of formula (I) in which $R_4$ is a group $N(R_9)(CH_2)_pR_{35}$ in which $R_{35}$ is a piperid-4-yl unsubstituted in the 1-position are obtained by carrying out a conventional deprotection reaction on the compounds of formula (I) in which $R_{35}$ is a piperid-4-yl substituted in the 1-position by a protective group.

The compounds of formula (I) in which $R_4$ is a group $N(R_9)CH_2R_{36}$ in which $R_{36}$ is a carboxyl can be prepared from the corresponding compounds of formula (I) in which $R_{36}$ is a $(C_1-C_7)$alkoxycarbonyl or a benzyloxycarbonyl. Then, reaction of a compound of formula (I) in which $R_4$ is a group $N(R_9)CH_2COOH$ with a compound of the formula $HNR_{38}R_{39}$, according to the appropriate techniques of amide coupling, gives the compounds of formula (I) in which $R_4$ is a group $N(R_9)$—$CH_2CONR_{38}R_{39}$.

The same methods described above can be used to prepare the compounds of formula (I) in which $R_4$ is a group $N(R_9)(C_2-C_{10})$alkyl-$R_{36}$ in which $R_{36}$ is a carboxyl or a group $CONR_{38}R_{39}$.

The compounds of formula (I) in which $R_4$ is a group $N(R_9)(C_2-C_{10})$alkyl-$NR_{32}R_{33}$ in which $NR_{32}R_{33}$ is a piperazin-1-yl substituted in the 4-position by a $(C_1-C_7)$ alkyl can be prepared either directly by the method according to the invention, starting from the correctly substituted compounds of formula (II), or by reaction of the corresponding compounds of formula (I) in which $NR_{32}R_{33}$ is a piperazin-1-yl unsubstituted in the 4-position with an aldehyde or a ketone in an acid medium, in the presence of a reducing agent such as sodium cyanoborohydride.

The compounds (I) in which $R_4$ and/or $R_6$ are a $(C_1-C_7)$ alkylsulfonamido, a phenylsulfonamido or a dimethylaminosulfonamido are obtained by reacting an alkylsulfonyl halide in which the alkyl is $C_1-C_7$, a benzenesulfonyl halide or, respectively, a dimethylsulfamoyl halide with a compound (I) in which $R_4$ and/or $R_6$ are an amino group.

The compounds (I) in which $R_4$ is a lactoylamino or mandeloylamino group are obtained by reacting a lactic acid or, respectively, a mandelic acid with a compound (I) in which $R_4$ is an amino group, according to the appropriate techniques of amide coupling.

The compounds (I) in which $R_4$ is an N'-(1-phenylethyl) ureido or N'-(1-naphth-1-ylethyl)ureido group are obtained by reacting an α-methylbenzyl isocyanate or, respectively, a naphth-1-ylethyl isocyanate with a compound (I) in which $R_4$ is an amino group.

The compounds (I) in which $R_4$ and/or $R_6$ are a group $NR_9R_{11}$, $R_{11}$ being a formyl or a $(C_1-C_7)$alkylcarbonyl, a $(C_1-C_7)$cycloalkylcarbonyl, an optionally substituted benzoyl, a phenacetyl in which the benzene ring is optionally substituted, a pyridylcarbonyl, a thienylcarbonyl, a furylcarbonyl or a piperid-4-ylcarbonyl, are obtained by reacting formic acid in acetic anhydride or, respectively, by reacting the appropriate anhydride or the appropriate acid chloride with a compound (I) in which $R_4$ and/or $R_6$ are a group $R_9NH$—, in the presence of an amine such as triethylamine.

The compounds (I) in which $R_4$ and/or $R_6$ are a group $NR_9R_{11}$, $R_{11}$ being a $(C_1-C_7)$alkoxycarbonyl, a phenoxycarbonyl or a benzyloxycarbonyl, are obtained by reacting a $C_1-C_7$-alkyl, phenyl or, respectively, benzyl chloroformate with a compound (I) in which $R_4$ and/or $R_6$ are a group $R_9NH$—.

Likewise, reaction of a phenoxythiocarbonyl chloride with a compound of formula (I) in which $R_4$ and/or $R_6$ are a group $R_9NH$— gives a compound of formula (I) in which $R_4$ and/or $R_6$ are a group $NR_9R_{11}$ in which $R_{11}$ is a phenoxythiocarbonyl.

A compound of formula (I) in which $R_4$ and/or $R_6$ are a group $N(R_9)CONH_2$ or $N(R_9)CSNH_2$ is prepared by reacting ammonia with a compound of formula (I) in which $R_4$ and/or $R_6$ are a group $NR_9R_{11}$ in which $R_{11}$ is a phenoxycarbonyl or a phenoxythiocarbonyl.

It is also possible to prepare compounds of formula (I) in which $R_4$ and/or $R_6$ are a ureido ($NR_9$—$CONR_{22}R_{23}$) or a thioureido ($NR_9CSNR_{22}R_{23}$) by reacting a compound $NHR_{22}R_{23}$ with a compound (I) in which $R_4$ and/or $R_6$ are a group $NR_9R_{11}$ in which $R_{11}$ is a phenoxycarbonyl or, respectively, a phenoxythiocarbonyl.

It is also possible to prepare compounds of formula (I) in which $R_4$ and/or $R_6$ are a ureido ($NR_9$—$CONR_{22}R_{23}$) or a thioureido ($NR_9CSNR_{22}R_{23}$) by reacting a carbamoyl chloride ($ClCONR_{22}R_{23}$) or, respectively, a thiocarbamoyl chloride ($ClCSNR_{22}R_{23}$) with a compound of formula (I) in which $R_4$ and/or $R_6$ are a group $R_9NH$—.

A compound (I) in which $R_4$ and/or $R_6$ are a group $NR_9R_{11}$ in which $R_{11}$ is a $(C_1-C_7)$alkylcarbamoyl can also be prepared by reacting a $C_1-C_7$-alkyl isocyanate with a compound (I) in which $R_4$ and/or $R_6$ are a group $R_9NH$—.

It is also possible to prepare a compound (I) in which $R_4$ and/or $R_6$ are a group $N(R_9)CONR_{22}R_{23}$ or $N(R_9)CSNR_{22}R_{23}$ in which $R_9$ is a $(C_1-C_7)$alkyl by reacting a base such as sodium hydride with a compound (I) in which $R_4$ and/or $R_6$ are a group $NHCONR_{22}R_{23}$ or $NHCSNR_{22}R_{23}$ and then reacting the product with a $(C_1-C_7)$alkyl halide.

A compound (I) in which $R_4$ and/or $R_6$ are a thioureido can also be prepared by reacting Lawesson's reagent with a compound (I) in which $R_4$ and/or $R_6$ are the corresponding ureido.

A compound (I) in which $R_4$ and/or $R_6$ are a group $NHCO(CH_2)_2CO_2H$ or $NHCO(CH_2)_3CO_2H$ can be prepared by reacting an anhydride, such as succinic anhydride or glutaric anhydride, with a compound (I) in which $R_4$ and/or $R_6$ are an amino. If appropriate, the resulting acid is converted to an ester or an amide.

A compound of formula (I) in which $R_4$ and/or $R_6$ are a group $\omega$-$R_{32}R_{33}N(C_1-C_4)$alkylCON$(R_9)$— can be prepared by reacting a halogeno$(C_1-C_4)$alkylcarbonyl halide such as bromoacetyl bromide, 3-chloropropionyl chloride, 4-chlorobutyryl chloride or 5-chlorovaleryl chloride, for example, with a compound of formula (I) in which $R_4$ and/or $R_6$ are a group $R_9NH$—; then, reaction of the resulting intermediate with a compound $HNR_{32}R_{33}$ gives the compound of formula (I) designated above.

It is possible to prepare a compound of formula (I) in which $R_4$ is an amino group by reacting a solution of HBr in AcOH with a compound (I) in which $R_4$ is a group $NR_9CO_2Me$.

The compounds of formula (I) in which $R_1$ and/or $R_6$ are a ($C_1$–$C_7$)alkoxy can be prepared directly by the method according to the invention, starting from the correctly substituted compounds of formula (II), (III) or (IV).

The compounds (I') in which $R'_1$ and/or $R_6$ are a hydroxyl can also be used to prepare compounds (I) in which $R_1$ and/or $R_6$ are a ($C_1$–$C_7$)alkoxy by reaction with a $C_1$–$C_7$-alkyl halide in the presence of a base such as a metal hydride or an alkali metal or alkaline earth metal carbonate like $K_2CO_3$ or $Cs_2CO_3$, in a solvent such as THF or DMF.

The compounds (I') in which $R'_1$ and/or $R_6$ are a hydroxyl can be obtained by the catalytic hydrogenation of a compound of formula (I') in which $R'_1$ and/or $R_6$ are a benzyloxy, for example in the presence of palladiumon-charcoal. These compounds can also be prepared from analogous compounds of formula (I') in which $R'_1$ and/or $R_6$ are an amino group by using the method described in J. Org. Chem., 1977, 42, 2053.

A compound of formula (I) in which $R_6$ is a nitro group can be used to obtain a compound (I) in which $R_6$ is an amino group by catalytic hydrogenation, for example in the presence of platinum oxide or Raney nickel, or by chemical reduction, for example in the presence of tin or iron in an acid medium; other compounds in which the amino group is substituted can then be prepared using reactions well known to those skilled in the art.

To prepare compounds of formula (I) in which $R_6$ is a ($C_1$–$C_7$)alkylamino or a ($C_1$–$C_{12}$)alkylamino, a compound of formula (I) in which $R_6$ is an amino group is reacted with an aldehyde or a ketone in an acid medium, in the presence of a reducing agent such as sodium cyanoborohydride; an identical reaction is used to prepare the compounds (I) in which $R_6$ is a dialkylamino in which the alkyls are identical or different, one of the alkyls being $C_1$–$C_7$ and the other $C_1$–$C_{12}$.

The compounds of formula (I) in which $R_6$ is a $\Delta$3-pyrrolin-1-yl group are prepared by reacting cis-1,4-dichlorobut-2-ene, under an inert atmosphere, with the compounds of formula (I) in which $R_6$ is an amino group, in the presence of a base such as triethylamine. The compounds of formula (I) in which $R_6$ is a pyrrolidin-1-yl group are then prepared by hydrogenation.

The reaction of cis-1,4-dichlorobut-2-ene with the compounds (I) in which $R_6$ is an amino group can also be carried out in air in the presence of a base such as $Na_2CO_3$; under these conditions, it results in the formation of a mixture of a compound of formula (I) in which $R_6$ is a $\Delta$3-pyrrolin-1-yl group and a compound of formula (I) in which $R_6$ is a pyrrol-1-yl group, which can be separated by chromatography.

To prepare the compounds of formula (I) in which $R_6$ is a group $R_9NH$— substituted by a ($C_3$–$C_7$)-cycloalkylmethyl, a compound of formula (I) in which $R_6$ is a group $R_9NH$— is reacted with a cycloalkylcarboxaldehyde in which the cycloalkyl is $C_3$–$C_7$, in an acid medium, in the presence of a reducing agent such as sodium cyanoborohydride.

If $R_6$ is an amino group, it is also possible to perform a nitrosation, for example in the presence of nitrous acid or sodium nitrite, in order to prepare a compound (I') in which $R'_6$ is a diazonium salt; the compounds (I) according to the invention in which $R_6$ is a cyano, a halogeno or a $C_1$–$C_7$-alkylthio are then obtained by reactions known to those skilled in the art.

The compounds (I) in which $R_6$ is an amino group substituted by a group $CH_2R_{36}$ are obtained by reacting a compound of the formula Hal-$CH_2$—COOR, in which Hal is a halogen, for example bromine, and R is a $C_1$–$C_7$-alkyl or a benzyl, with a compound (I) in which $R_6$ is a group $R_9NH$—, in the presence of cuprous chloride; if appropriate, the resulting ester is converted to the acid or an amide.

The compounds (I) in which $R_6$ is a guanidino group which is unsubstituted or monosubstituted or disubstituted by a ($C_1$–$C_7$)alkyl, a phenyl or a benzyl can be prepared from compounds (I) in which $R_6$ is a phenoxycarboxamido group by reaction with cyanamide or a derivative thereof correctly substituted on the nitrogen.

The compounds of formula (I) in which $R_6$ is a ($C_1$–$C_7$) alkoxycarbonyl can be prepared directly by the method according to the invention. By methods known to those skilled in the art, they can be used to obtain the compounds of formula (I) in which $R_6$ is a carboxyl group.

According to another procedure, the compounds of formula (I) in which $R_6$ is a benzyloxycarbonyl can be used, by catalytic hydrogenation, to obtain the compounds (I) in which $R_6$ is a carboxyl. Reaction with a thionyl halide gives the compounds of formula (I') in which $R'_6$ is a halogenocarbonyl. Such compounds are reacted with a compound $HNR_{14}R_{15}$ in order to prepare compounds of formula (I) in which $R_6$ is a carbamoyl substituted by $R_{14}$ and $R_{15}$.

The compounds of formula (I) in which $R_6$ is a phenoxycarbonyl can also be used to obtain the compounds of formula (I) in which $R_6$ is a phenylcarbamoyl or a ($C_1$–$C_7$) alkylcarbamoyl by reaction with an aniline or a ($C_1$–$C_7$) alkylamine. A substituted aniline or an alkylamine substituted on the alkyl makes it possible to obtain compounds of formula (I) in which $R_6$ is a phenylcarbamoyl substituted on the phenyl or, respectively, an alkylcarbamoyl substituted on the alkyl.

The compounds of formula (I) in which $R_6$ is a carboxyl can also be used to obtain the compounds of formula (I) in which $R_6$ is a group $CONR_{14}R_{15}$ by reaction with a compound of the formula $HNR_{14}R_{15}$ in the presence of BOP and an amine such as diisopropylethylamine.

The compounds of formula (I) in which $R_6$ is a group $COR_{12}$ can also be obtained by reacting a compound $R_{12}H$ with compounds (I) in which $R_6$ is a phenoxycarbonyl.

A compound of formula (I) in which $R_6$ is a thiocarbamoyl can be prepared by reacting Lawesson's reagent with a compound (I) in which $R_6$ is the corresponding carbamoyl.

The compounds of formula (I) in which $R_6$ is a sulfamoyl substituted by $R_{16}$ and $R_{17}$ are obtained by reacting a compound $HNR_{16}R_{17}$ with a compound of formula (I') in which $R'_6$ is a halogenosulfonyl group.

Methods known to those skilled in the art can be used to resolve the enantiomers of the compounds of formula (I) in which the carbon in the 3-position of the indol-2-one is asymmetric. For example, the compounds of formula (I) in which $R_4$ is an amino can be resolved using (S)-(+)-lactic acid, (S)-(+)-mandelic acid, (R)-(−)-mandelic acid, (R)-(+)-(naphth-1-yl)ethyl isocyanate, (R)-(−)-(naphth-1-yl)ethyl isocyanate, (S)-(−)-α-methylbenzyl isocyanate, (R)-(+)-α-methylbenzyl isocyanate, (1S)-(+)-10-camphorsulfonic acid or (1R)-(−)-10-camphorsulfonic acid.

It is also possible to carry out the optical resolution of the compounds of formula (II). Thus the compounds of formula (II) in which $R'_4$ is an amino can be resolved according to the method described in Bull. Chem. Soc. Jpn., 1992, 65, 2359–2365, and illustrated below. Reaction of a compound of formula (V) with (S)-(+)-2-phenylglycinol or (R)-(−)-2-phenylglycinol gives a mixture of diastereoisomers of a compound of formula (II) in which $R'_4$ is NH—CH($C_6H_5$)—$CH_2OH$, which can be separated for example by chromatography or crystallization. Then, oxidation of one of the above diastereoisomers with lead tetraacetate and hydrolysis in an acid medium gives an enantiomerically pure compound of formula (II) in which $R'_4$ is an amino.

In the course of any one of the steps of the method of preparing the compounds of formula (I) or their intermediates of formula (II), (III) or (IV), it may be necessary and/or desirable to protect the reactive or sensitive functional groups, such as the amine, hydroxyl, thiol or carboxyl groups, present on any one of the molecules in question. This protection can be effected using the conventional protective groups such as those described in Protective Groups in Organic Chemistry, J. F. W. McOmie, published by Plenum Press, 1973, and in Protective Groups in Organic Synthesis, T. W. Greene and P. G. M. Wutts, published by John Wiley and Sons, 1991. The protective groups can be removed in a subsequent opportune step by using the methods known to those skilled in the art which do not affect the rest of the molecule in question.

The affinity of the compounds according to the invention for the vasopressin receptors was determined in vitro using the method described in C. J. Lynch et al., J. Biol. Chem., 1985, 260 (5), 2844–2851. This method consists in studying the displacement of tritiated vasopressin bound to the $V_1$ sites of rat liver membranes. The concentrations of the compounds according to the invention which cause a 50% inhibition of the binding of tritiated vasopressin ($IC_{50}$) are low, ranging down to $10^{-9}M$.

The affinity of the compounds (I) according to the invention for the $V_2$ receptors was measured on a bovine kidney membrane preparation by a method adapted from P. Crause et al., Molecular and Cellular Endocrinology, 1982, 28, 529–541, and F. L. Stassen et al., J. Pharmacol. Exp. Ther., 1982, 223, 50–54. The compounds according to the invention inhibit the binding of tritiated arginine vasopressin to the receptors of the membrane preparation. The $IC_{50}$ values of the compounds according to the invention are low, ranging down to $10^{-9}M$.

The antagonistic activity of the compounds according to the invention towards the $V_2$ receptors was demonstrated by the adenylate cyclase activity assay performed by a method adapted from M. Laburthe et al., Molecular Pharmacol., 1986, 29, 23–27. A bovine kidney membrane preparation is used and each product is incubated for 10 minutes at 37° C., either by itself or in the presence of AVP (arginine vasopressin) at a concentration of $3.10^{-8}M$. The cyclic AMP (cyclic adenosine monophosphate) produced is measured by radioimmunoassay. The concentration which causes a 50% inhibition ($IC_{50}$) of the stimulation of adenylate cyclase induced by $3.10^{-8}M$ AVP is determined. The $IC_{50}$ values determined are of the order of $10^{-7}M$, ranging down to $10^{-9}M$.

The agonistic or antagonistic activity of the compounds according to the invention, administered orally, towards the vasopressin receptors is evaluated in hyperhydrated rats (OFA, Sprague-Dawley strain) treated with vasopressin. The antagonistic activity of the compounds according to the invention was also evaluated in normally hydrated rats (OFA, Sprague-Dawley strain) by the technique described in Br. J. Pharmacol., 1992, 105, 787–791. The diuretic effect was observed for some compounds at a dose of 10 mg/kg.

Likewise, the affinity of the compounds (I) according to the invention for the ocytocin receptors was determined in vitro by the displacement of a radioiodinated ocytocin analog bound to the receptors of a gestating rat mammary gland membrane preparation by a technique similar to that described by J. Eland et al. in Eur. J. Pharmacol., 1987, 147, 197–207. The $IC_{50}$ values of the compounds according to the invention reach $10^{-9}M$.

The compounds according to the invention are active after administration by different routes, especially orally.

No signs of toxicity are observed with these compounds at the pharmacologically active doses.

Thus the compounds according to the invention can be used in the treatment or prevention of various vasopressin-dependent or ocytocin-dependent complaints, cardiovascular complaints such as hypertension, pulmonary hypertension, cardiac insufficiency, myocardial infarction or coronary vasospasm, in particular in smokers, unstable angina and PTCA (percutaneous transluminal coronary angioplasty), cardiac ischemia, hemostatic disorders, especially hemophilia, and von Willebrand's syndrome; complaints of the central nervous system, for example migraine, cerebral vasospasm, cerebral hemorrhage, cerebral edemas, depression, anxiety, psychotic states and memory disorders; complaints of the renal system, such as edemas, renal vasospasm, necrosis of the renal cortex, hyponatremia, hypokalemia and Schwartz Bartter's syndrome; complaints of the gastric system, such as gastric vasospasm, hepatocirrhosis, ulcers, the pathology of vomiting, for example nausea, including nausea due to chemotherapy, travel sickness or else the syndrome of inappropriate secretion of antidiuretic hormone (SIADH), diabetes insipidus and enuresis. The compounds according to the invention can also be used in the treatment of disorders of sexual behavior; in women, the compounds according to the invention can be used for treating dysmenorrhea or premature labor. The compounds according to the invention can also be used in the treatment of small cell lung cancer, hyponatremic encephalopathy, Raynaud's disease, pulmonary syndrome, glaucoma and cataract and in postoperative treatments, especially after abdominal surgery.

The present invention further relates to pharmaceutical compositions containing an effective dose of a compound according to the invention, or a pharmaceutically acceptable salt thereof, and suitable excipients.

Said excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal or rectal administration, the active principles of formula (I) above, or their salts where appropriate, can be administered to animals and humans in unit forms of administration, mixed with conventional pharmaceutical carriers, for the prophylaxis or treatment of the above disorders or diseases. The appropriate unit forms of administration include forms for oral administration, such as tablets, gelatin capsules, powders, granules and solutions or suspensions to be taken orally, forms for sublingual, buccal, intratracheal or intranasal administration, aerosols, implants, forms for subcutaneous, intramuscular or intravenous administration and forms for rectal administration. For topical application, the compounds according to the invention can be used in creams, ointments or lotions.

To obtain the desired prophylactic or therapeutic effect, the dose of active principle can vary between 0.01 and 50 mg per kg of body weight and per day.

Each unit dose can contain from 0.5 to 1000 mg, preferably from 1 to 500 mg, of active ingredients in combination with a pharmaceutical carrier. This unit dose can be administered 1 to 5 times a day so as to administer a daily dosage of 0.5 to 5000 mg, preferably 1 to 2500 mg.

If a solid composition in the form of tablets is prepared, the main active ingredient is mixed with a pharmaceutical vehicle such as gelatin, starch, lactose, magnesium stearate, talc, silica or the like. The tablets can be coated with sucrose, a cellulose derivative or other appropriate substances, or else they can be treated so as to have a sustained or delayed activity and so as to release a predetermined amount of active principle continuously.

A preparation in the form of gelatin capsules is obtained by mixing the active ingredient with a diluent and incorporating the resulting mixture into soft or hard gelatin capsules.

A preparation in the form of a syrup or elixir or for administration in the form of drops can contain the active ingredient together with a sweetener, which is preferably calorie-free, methylparaben and propylparaben as antiseptics, a flavoring and an appropriate dye.

The water-dispersible powders or granules can contain the active ingredient mixed with dispersants or wetting agents, or suspending agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral administration is effected using aqueous suspensions, isotonic saline solutions or sterile and injectable solutions which contain pharmacologically compatible dispersants and/or wetting agents, for example propylene glycol or polyethylene glycol.

The active principle can also be formulated as microcapsules or microspheres, if appropriate with one or more carriers or additives.

In addition to the products of formula (I) above or one of their pharmaceutically acceptable salts, the compositions of the present invention can contain other active principles which may be useful in the treatment of the disorders or diseases indicated above.

Thus the present invention further relates to pharmaceutical compositions in which several active principles are present in association, one of them being a compound according to the invention.

Thus, according to the present invention, it is possible to prepare pharmaceutical compositions in which a compound according to the invention is present in association with a compound which acts on the reninangiotensin system, such as a converting enzyme inhibitor, an angiotensin II antagonist or a renin inhibitor. A compound according to the invention can also be associated for example with a peripheral vasodilator, a calcium inhibitor, a beta-blocker, an alpha-1-blocker or a diuretic. Such compositions will be useful in particular in the treatment of hypertension or heart failure.

It is also possible to associate two compounds according to the invention, namely a specific $V_1$ receptor antagonist with a specific $V_2$ receptor antagonist, or else a specific $V_1$ receptor antagonist with a specific ocytocin antagonist.

These associations will make it possible to reinforce the therapeutic activities of the compounds according to the invention.

The invention will now be described in greater detail by means of the non-limiting illustrative Preparations and Examples below.

PREPARATIONS

Preparations of the 1,3-dihydroindol-2-ones (II)

Preparation 1

3-Amino-5-chloro-1,3-dihydro-3-phenylindol-2-one

A) 5-Chloro-1,3-dihydro-3-phenylindol-2-one

This compound is prepared according to Aeberli P. and Houlikan W. J. in J. Org. Chem., 1968, 33 (4), 1640–1643.

B) 3-Bromo-5-chloro-1,3-dihydro-3-phenylindol-2-one

This compound is prepared according to Bolotov V. V. et al. in Farm. Zh. (Kiev), 1976, 5, 30–33.

A mixture of 3.0 g of the compound obtained in the previous step and 80 ml of $CCl_4$ is heated to the reflux point and a solution of 2.5 g of bromine in 3 ml of $CCl_4$ is added slowly. After refluxing for 30 minutes, the reaction mixture is cooled and evaporated under vacuum. The expected product is used as such in the next step.

C) 3-Amino-5-chloro-1,3-dihydro-3-phenylindol-2-one

A solution of the compound obtained in the previous step in 30 ml of ether is cooled to 0° C. and a stream of gaseous ammonia is passed through. After stirring for 72 hours at RT, the mixture is evaporated under vacuum and the residue is taken up with water, extracted with AcOEt, washed with water, dried over sodium sulfate and evaporated under vacuum. The residue is chromatographed on silica using a DCM/AcOEt/hexane mixture (40/40/20; v/v/v) as the eluent to give the expected product after crystallization from an AcOEt/MeOH mixture. m=1.4 g. M.p.=230°–235° C.

Preparation 2

3-Amino-5-chloro-3-(2-chlorophenyl)-1,3-dihydroindol-2-one

A) N-p-Chlorophenyl-DL-2-chloromandelamide

A mixture of 38.25 g of p-chloroaniline, 55.95 g of DL-2-chloromandelic acid and 280 ml of 1,2-dichlorobenzene is heated at 200° C. for 7 hours, the water formed being removed by means of a Dean-Stark apparatus. The reaction mixture is partially concentrated under vacuum and left to crystallize. The crystalline product formed is filtered off and washed with iso ether to give 44.92 g of the expected product.

B) 5-Chloro-3-(2-chlorophenyl)-1,3-dihydroindol-2-one 172 ml of concentrated sulfuric acid (95%) are cooled to 10° C., 39 ml of fuming sulfuric acid (30% oleum) are added and 42.92 g of the compound obtained in the previous step are then added in portions, the internal temperature being kept below 40° C. The reaction mixture is stirred for 24 hours at RT and poured into iced water and the precipitate formed is filtered off and washed with water. The precipitate is dissolved in chloroform, the organic phase is washed with water to pH 7 and dried over sodium sulfate and the solvent is evaporated off under vacuum to give 35 g of the expected product after crystallization from a DCM/THF/iso ether mixture. M.p.=198°–200° C.

C) 3-Bromo-5-chloro-3-(2-chlorophenyl)-1,3-dihydroindol-2-one

This compound is prepared according to the procedure described in step B of Preparation 1. This compound can also be prepared according to the following procedure: A solution of 11.62 g of bromine in 15 ml of chloroform is added slowly at RT to a solution of 22.44 g of the compound obtained in the previous step in 500 ml of chloroform. The mixture is then evaporated under vacuum and the residue is taken up with DCM and evaporated under vacuum. The expected product is used as such.

D) 3-Amino-5-chloro-3-(2-chlorophenyl)-1,3-dihydroindol-2-one

This compound is prepared according to the procedure described in step C of Preparation 1 from the compound obtained in the previous step. The expected product is obtained after crystallization from a DCM/iso ether mixture. M.p.=234° C.

Preparation 3

5-Chloro-3-(2-chlorophenyl)-1,3-dihydro-3-(methylamino)indol-2-one 0.460 g of gaseous methylamine dissolved in 4 ml of ether is added at RT to a solution of 4.4 g of the compound obtained in step C of Preparation 2 in 30 ml of DCM. After stirring for 30 minutes, the mixture is extracted with DCM, washed with water, dried over sodium sulfate and evaporated under vacuum. The residue is chromatographed on silica using an AcOEt/hexane mixture (50/50; v/v) as the eluent to give the expected product after crystallization from a DCM/iso ether mixture. m=0.655 g. M.p.=230° C.

The indol-2-one derivatives below are obtained by following the same procedure and varying the amine:

5-Chloro-3-(2-chlorophenyl)-1,3-dihydro-3-(dimethylamino)indol-2-one, m.p.=148°–151° C.
5-Chloro-3-(2-chlorophenyl)-3-(diethylamino)-1,3-dihydroindol-2-one, m.p.=160°–165° C.
5-Chloro-3-(2-chlorophenyl)-3-(ethylamino)-1,3-dihydroindol-2-one, m.p.=240°–242° C.
5-Chloro-3-(2-chlorophenyl)-I,3-dihydro-3-(propylamino)indol-2-one, m.p.=218°–220° C.
3-(tert-Butylamino)-5-chloro-3-(2-chlorophenyl)-1,3-dihydroindol-2-one, m.p.=203°–204° C.
5-Chloro-3-(2-chlorophenyl)-1,3-dihydro-3-(isobutylamino)indol-2-one, m.p.=185° C.
5-Chloro-3-(2-chlorophenyl)-1,3-dihydro-3-(pentylamino)indol-2-one, m.p.=155° C.
3-(Benzylamino)-5-chloro-3-(2-chlorophenyl)-1,3-dihydroindol-2-one, m.p.=170°–175° C.
5-Chloro-3-(2-chlorophenyl)-1,3-dihydro-3-[(2-methoxyethyl)amino]indol-2-one, m.p.=174°–176° C.

Preparation 4

Ethyl N-[5-chloro-3-(2-chlorophenyl)-2,3-dihydro-2-oxoindol-3-yl]glycinate 0.435 g of DIPEA is added slowly to a mixture of 0.500 g of the compound obtained in step C of Preparation 2, 0.281 g of ethyl glycinate hydrochloride and 10 ml of chloroform. After stirring for 1 hour, the mixture is washed with water, dried over sodium sulfate and evaporated under vacuum. The residue is chromatographed on silica using a DCM/AcOEt mixture (90/10; v/v) as the eluent to give the expected product after crystallization from a DCM/iso ether mixture. m=0.30 g. M.p.=175° C.

Preparation 5

3-(4-tert-Butoxycarbonylpiperazin-1-yl)-5-chloro-3-(2-chlorophenyl)-1,3-dihydroindol-2-one A solution of 1 g of the compound obtained in step C of Preparation 2 in 5 ml of chloroform is added at RT to a solution of 0.525 g of 1-tert-butoxycarbonylpiperazine and 0.348 g of DIPEA in 20 ml of chloroform. The mixture is stirred for 18 hours at RT and then washed with water, dried over sodium sulfate and evaporated under vacuum. The residue is chromatographed on silica using an AcOEt/hexane mixture (20/80; v/v) as the eluent to give the expected product after crystallization from a DCM/iso ether mixture. m=0.54 g. M.p.=235° C.

Preparation 6

5-Chloro-1,3-dihydro-3-hydroxy-3-(2-methoxyphenyl)indol-2-one

A solution of 2-methoxyphenylmagnesium bromide is prepared from 1.35 g of magnesium and 10.5 g of 1-bromo-2-methoxybenzene in 100 ml of ether. This solution is added in 10 minutes at RT, under an argon atmosphere, to a mixture of 4.1 g of 5-chloroisatin and 70 ml of THF. After stirring for 1 hour at RT, water is added and the product is filtered off, redissolved in THF, dried over magnesium sulfate and evaporated under vacuum in the presence of iso ether. The residue is chromatographed on silica using a DCM/AcOEt mixture (60/40; v/v) as the eluent to give the expected product after crystallization from a THF/iso ether mixture. m=3.7 g. M.p.=235°–238° C.

Preparation 7

3-Amino-5-chloro-1,3-dihydro-3-(2-methoxyphenyl)indol-2-one

A) 5-Chloro-1,3-dihydro-3-(2-methoxyphenyl)-3-(methylsulfonyloxy)indol-2-one

A solution of 0.500 g of the compound obtained in Preparation 6 in 7 ml of THF is cooled to −10° C. and 0.350 g of triethylamine and then 0.400 g of methanesulfonyl chloride are added. This solution is kept for 48 hours at a temperature of between 0 and +20° C. and used as such in the next step.

B) 3-Amino-5-chloro-1,3-dihydro-3-(2-methoxyphenyl)-indol-2-one

The solution obtained in the previous step is cooled to 0° C. and gaseous ammonia is introduced by bubbling. The mixture is stirred for 24 hours at RT and evaporated under vacuum. The residue is taken up with a 5% solution of potassium carbonate, extracted with AcOEt, washed with water, dried over sodium sulfate and evaporated under vacuum. The residue is chromatographed on silica using a DCM/AcOEt mixture (70/30; v/v) as the eluent to give the expected product after crystallization from a DCM/MeOH mixture. m=0.182 g. M.p.=231°–233° C.

This compound can also be obtained by following the two steps of the method described below.

A') 3,5-Dichloro-1,3-dihydro-3-(2-methoxyphenyl)indol-2-one

A mixture of 2.15 g of the compound obtained in Preparation 6 and 75 ml of DCM is cooled to 0° C. and 1.1 ml of pyridine and then 0.75 ml of thionyl chloride are added. After stirring for two hours, the reaction mixture is chromatographed directly on silica using DCM and then a DCM/AcOEt mixture (80/20; v/v) as the eluent to give the expected product after crystallization from a DCM/AcOEt mixture. m=1.9 g. M.p.=220°–224° C.

B') 3-Amino-5-chloro-1,3-dihydro-3-(2-methoxyphenyl)-indol-2-one 10 ml of a solution of ammonia in THF (1.16 g of gaseous ammonia in 110 ml of THF) are added at RT to a solution of 1.9 g of the compound obtained in the previous step in 80 ml of THF. After stirring for 2 hours at RT, a further 10 ml of the solution of ammonia in THF are added and the mixture is stirred for 30 hours. The solvent is evaporated off under vacuum and the residue is taken up with a 5% solution of potassium carbonate and extracted with AcOEt. An insoluble material, which is the expected product, is filtered off and recrystallized from a THF/MeOH mixture. M.p.= 231°–232° C. To obtain a second crop, the organic phase is taken up with AcOEt, washed with water, dried over sodium sulfate and evaporated under vacuum. The residue is chromatographed on silica using a DCM/AcOEt mixture (50/50; v/v) as the eluent to give a total of 0.88 g of the expected product.

Preparation 8

3-Azido-5-chloro-3-(2-chlorophenyl)-1,3-dihydroindol-2-one

A mixture of 3.00 g of the compound obtained in step C of Preparation 2, 1.65 g of sodium azide and 100 ml of acetonitrile is refluxed for 1 hour. After evaporation under vacuum, the residue is taken up with water, extracted with AcOEt, washed with water and with a saturated solution of NaCl, dried over sodium sulfate and evaporated under vacuum to give the expected product after crystallization from a DCM/iso ether/THF mixture. m=0.894 g. M.p.=178° C.

Preparations 9 and 10

3-Amino-5,6-dichloro-1,3-dihydro-3-phenylindol-2-one (Preparation 9) and 3-amino-4,5-dichloro-1,3-dihydro-3-phenylindol-2-one (Preparation 10)

A) 5,6-Dichloro-1,3-dihydro-3-phenylindol-2-one and 4,5-dichloro-1,3-dihydro-3-phenylindol-2-one A mixture of these two compounds is prepared according to the procedure described in step B of Preparation 2 from N-3,4-dichlorophenyl-DL-mandelamide, itself obtained according to the procedure described in step A of Preparation 2 from 3,4-dichloroaniline and DL-mandelic acid. The mixture of the two expected products is obtained after recrystallization from EtOH.

B) 3-Bromo-5,6-dichloro-1,3-dihydro-3-phenylindol-2-one and 3-bromo-4,5-dichloro-1,3-dihydro-3-phenylindol-2-one A solution of 2.6 g of bromine in 2 ml of chloroform is added in 5 minutes at RT to a suspension of 4.71 g of the mixture of the two compounds obtained in the previous step in 70 ml of chloroform. Stirring for 30 minutes and evaporation under vacuum gives the mixture of the two expected products, which is used as such in the next step.

C) 3-Amino-5,6-dichloro-1,3-dihydro-3-phenylindol-2-one (Preparation 9) and 3-amino-4,5-dichloro-1,3-dihydro-3-phenylindol-2-one (Preparation 10)

A solution of the mixture of the two compounds obtained in the previous step in 20 ml of THF is cooled to 0° C. and a solution of 0.60 g of gaseous ammonia in 10 ml of THF is added. After stirring for two hours, a further solution of 0.30 g of gaseous ammonia in 5 ml of THF is added and the mixture is stirred for 48 hours, the temperature being allowed to rise to RT. The reaction medium is evaporated under vacuum, extracted with AcOEt, washed with water, dried over sodium sulfate and evaporated under vacuum. The residue is chromatographed on silica using a DCM/AcOEt mixture (75/25; v/v) as the eluent to give the product of Preparation 9 after crystallization from a DCM/AcOEt mixture. Elution is then carried out with a DCM/AcOEt mixture (40/60; v/v) to give the product of Preparation 10 after crystallization from a DCM/iso ether mixture.

Compound of Preparation 9, m.p.=211°–212° C.
Compound of Preparation 10, m.p.=185°–187° C.

Preparation 11

5-Ethoxy-3-(2-ethoxycarbonyl-1-ethoxycarbonylhydrazino)-1,3-dihydro-3-phenylindol-2-one A) 5-Ethoxy-1,3-dihydro-3-phenylindol-2-one This compound is prepared according to the procedure described in step B of Preparation 66 from N-4-ethoxyphenyl-DL-mandelamide (138° C.), itself obtained according to the procedure described in step A of Preparation 2 from 4-ethoxyaniline and DL-mandelic acid. This gives the expected product. M.p.=125°–130° C.

B) 5-Ethoxy-3-(2-ethoxycarbonyl-1-ethoxycarbonylhydrazino)-1,3-dihydro-3-phenylindol-2-one A mixture of 3.42 g of the compound obtained in the previous step and 30 ml of THF is cooled to −70° C. and 20 ml of a 1.5M solution of lithium diisopropylamide in cyclohexane are added slowly under an argon atmosphere. The mixture is stirred for 15 minutes, the temperature being allowed to rise to −20° C., it is then cooled to −70° C. and 2.38 g of diethyl azodicarboxylate are added all at once. After stirring for 30 minutes, water is added, the temperature is allowed to rise to RT and the solvent is evaporated off under vacuum. The residue is extracted with AcOEt, washed with water and with a saturated solution of NaCl, dried over sodium sulfate and evaporated under vacuum. The residue is chromatographed on silica using a DCM/AcOEt mixture (65/35; v/v) as the eluent to give the expected product after crystallization from a DCM/iso ether mixture. m=2.7 g. M.p.=202°–204° C.

Preparations 12 and 13

5-Chloro-3-(2-chlorophenyl)-1,3-dihydro-3-[[(1S)-1-(methoxycarbonyl)ethyl]amino]indol-2-one, isomer A and isomer B 2.04 g of DIPEA are added to a mixture of 2.00 g of the compound obtained in step C of Preparation 2, 1.12 g of methyl (L)-alaninate hydrochloride and 40 ml of chloroform. After stirring for 18 hours, the mixture is washed with water, dried over sodium sulfate and evaporated under vacuum. The residue is chromatographed on silica using an AcOEt/hexane mixture (40/60; v/v) as the eluent. The two isomers are separated out:

the less polar isomer, A: compound of Preparation 12. m=0.639 g. M.p.=214° C. $\alpha_D^{20}$=+137.2° (c=0.53; chloroform);

the more polar isomer, B: compound of Preparation 13. m=0.400 g. M.p.=165° C. $\alpha_D^{20}$=155.2° (c=0.38; chloroform).

Preparation 14

5-Chloro-1,3-dihydro-3-hydroxy-3-(2-methylphenyl)indol-2-one

A solution of 2-methylphenylmagnesium bromide is prepared from 2.7 g of magnesium, 19 g of 1-bromo-2-methylbenzene and 100 ml of ether. A mixture of 5.04 g of 5-chloroisatin and 100 ml of THF is cooled in an ice bath under an argon atmosphere and the solution of magnesium compound prepared above is added slowly. After stirring for 4 hours, water is added and the solvents are evaporated off under vacuum. The residue is extracted with AcOEt, the precipitate formed is filtered off and the organic phase of the filtrate is dried over magnesium sulfate and evaporated under vacuum. The residue obtained, combined with the precipitate previously filtered off, is crystallized from MeOH to give 4.8 g of the expected product. M.p.=285°–295° C.

Preparation 15

3-Amino-5-chloro-1,3-dihydro-3-(2-methylphenyl)indol-2-one

A) 3,5-Dichloro-1,3-dihydro-3-(2-methylphenyl)indol-2-one

A mixture of 2 g of the compound obtained in Preparation 14 and 72 ml of DCM is cooled to 0° C. and 1.04 ml of pyridine and then 0.76 ml of thionyl chloride are added. After stirring for 15 minutes, the reaction mixture is chromatographed directly on silica using a gradient of a DCM/AcOEt mixture (from 95/5; v/v to 80/20; v/v) as the eluent to give the expected product, which is used as such in the next step.

B) 3-Amino-5-chloro-1,3-dihydro-3-(2-methylphenyl)-indol-2-one

A solution of 1.97 g of the compound obtained in the previous step in 80 ml of THF is cooled to 0° C. and a solution of 0.230 g of gaseous ammonia in 20 ml of THF is added. After stirring for 24 hours at RT, water is added, the solvent is evaporated off and the residue is extracted with AcOEt, washed with water, dried over sodium sulfate and evaporated under vacuum. The residue is chromatographed on silica using a gradient of a DCM/AcOEt mixture (from 80/20; v/v to 60/40; v/v) as the eluent to give the expected product after crystallization from an MeOH/iso ether mixture. m=1.10 g. M.p.=218°–222° C.

Preparation 16

3-Amino-3-(2-chlorophenyl)-5-ethoxy-1,3-dihydroindol-2-one

A) 3-(2-Chlorophenyl)-5-ethoxy-1,3-dihydroindol-2-one

This compound is prepared according to the procedure described in step B of Preparation 66 from N-4-ethoxyphenyl-DL-2-chloromandelamide (120°–130° C.), itself obtained according to the procedure described in step A of Preparation 2 from 4-ethoxyaniline and DL-2-chloromandelic acid. This gives the expected product. M.p.=176°–180° C.

B) 3-Chloro-3-(2-chlorophenyl)-5-ethoxy-1,3-dihydroindol-2-one 1.16 g of N-chlorosuccinimide are added to a suspension of 2.5 g of the compound obtained in the previous step in 100 ml of $CC_4$ and the mixture is refluxed for 1 hour. After cooling to RT, the insoluble material is filtered off and the filtrate is evaporated under vacuum. The residue is chromatographed on silica using DCM and then a DCM/AcOEt mixture (95/5; v/v) as the eluent to give the expected product after recrystallization from a DCM/hexane mixture. m=1.46 g. M.p.=128°–132° C.

This compound can also be obtained by following the two steps of the method described below.

A') 3-(2-Chlorophenyl)-5-ethoxy-1,3-dihydro-3-hydroxyindol-2-one

This compound is prepared according to the procedure described in Preparation 6 from 5-ethoxyisatin and 2-chlorophenylmagnesium bromide (prepared according to P. G. Gassman in J. Am. Chem. Soc., 1974, 9, 5512).

B') 3-Chloro-3-(2-chlorophenyl)-5-ethoxy-1,3-dihydroindol-2-one

This compound is prepared according to the procedure described in step Al of Preparation 7 from the compound obtained in the previous step and thionyl chloride. M.p.=128°–132° C.

C) 3-Azido-3-(2-chlorophenyl)-5-ethoxy-1,3-dihydroindol-2-one 0.339 g of sodium azide is added to a solution of 0.560 g of the compound obtained in step B or B' in 20 ml of acetonitrile and the mixture is refluxed for 30 minutes. The solvent is evaporated off under vacuum and the residue is taken up with water, extracted with AcOEt, washed with a saturated solution of NaCl, with water and with a 5% aqueous solution of sodium dithionite, re-extracted with DCM, dried over sodium sulfate and evaporated under vacuum. The residue is chromatographed on silica using DCM and then a DCM/AcOEt mixture (95/5; v/v) as the eluent to give 0.377 g of the expected product. Infrared spectrum in DCM: 3440 $cm^{-1}$, 2100 $cm^{-1}$, 1745 $cm^{-1}$.

D) 3-Amino-3-(2-chlorophenyl)-5-ethoxy-1,3-dihydroindol-2-one 0.83 ml of triethylamine and then 0.60 ml of propane-1,3-dithiol are added by syringe, under an argon atmosphere, to a solution of 0.975 g of the compound obtained in the previous step in 14.8 ml of MeOH and the reaction mixture is heated at 60° C. overnight. It is evaporated under vacuum and the residue is chromatographed directly on silica using DCM and then a DCM/AcOEt mixture (70/30; v/v) as the eluent to give 0.786 g of the expected product, a sample of which is recrystallized from a DCM/iso ether mixture. M.p.=173°–175° C.

Preparation 17

5-Chloro-3-cyclohexyl-1,3-dihydro-3-hydroxyindol-2-one

A suspension of 18.15 g of 5-chloroisatin in 45 ml of THF is cooled to +4° C., 200 ml of a 2M solution of cyclohexylmagnesium chloride in ether are added dropwise and the mixture is stirred for 3 hours at RT. 900 ml of a saturated solution of ammonium chloride are added and the solvents are concentrated under vacuum. The aqueous phase is extracted with AcOEt, the organic phase is washed with a saturated solution of NaCl and dried over sodium sulfate and the solvent is evaporated of f under vacuum to give 4 g of the expected product after crystallization from a THF/AcOEt mixture.

NMR spectrum at 200 MHz in DMSO-$d_6$
0.4 to 2.0 ppm: m: 11H
5.9 ppm: s: 1H
6.8 ppm: d: 1H
7.2 ppm: m: 2H
10.35 ppm: s: 1H Preparation 18

5-Chloro-3-cyclohexyl-1,3-dihydro-3-(methylamino)indol-2-one

A) 3,5-Dichloro-3-cyclohexyl-1,3-dihydroindol-2-one

A solution of 1 g of the compound obtained in Preparation 17 in 40 ml of DCM is cooled to +4° C. and 0.57 ml of pyridine and then 0.42 ml of thionyl chloride are added. After stirring for 10 minutes, the reaction mixture is chromatographed directly on silica using DCM and then a DCM/AcOEt mixture (95/5; v/v) as the eluent to give 1 g of the expected product, which is used as such in the next step.

B) 5-Chloro-3-cyclohexyl-1,3-dihydro-3-(methylamino)-indol-2-one 0.88 ml of a 33% solution of methylamine in EtOH is added at RT to a solution of 1 g of the compound obtained in the previous step in 15 ml of THF and the mixture is stirred for 24 hours. Water is added to the reaction mixture, the solvent is concentrated under vacuum, the aqueous phase is extracted with AcOEt, the organic phase is washed with a saturated solution of NaCl and dried over sodium sulfate and the solvent is evaporated off under vacuum. The residue is chromatographed on silica using DCM and then a DCM/AcOEt mixture (80/20; v/v) as the eluent to give 0.85 g of the expected product after crystallization from a DCM/iso ether mixture. M.p.=195°–198° C.

Preparation 19

5-Chloro-3-(cyclohexylmethyl)-1,3-dihydro-3-hydroxyindol-2-one

A solution of cyclohexylmethylmagnesium bromide is prepared from 5.37 g of magnesium and 30.8 ml of bromomethylcyclohexane in 15 ml of ether. This solution is added dropwise at +4° C., under an argon atmosphere, to a mixture of 10 g of 5-chloroisatin and 25 ml of THF. After stirring for 3 hours at RT, 500 ml of a saturated solution of ammonium chloride are added, extraction is carried out with AcOEt, the organic phase is washed with a saturated solution of NaCl and with water and dried over sodium sulfate and the solvent is evaporated off under vacuum to give 12 g of the expected product after crystallization from AcOEt and recrystallization from a THF/AcOEt mixture. M.p.=252°–253° C. (dec.).

This compound can also be obtained by following the three steps of the method described below.

A') 5-Chloro-3-(cyclohexylmethylene)-1,3-dihydroindol-2-one

A solution of 10 g of 5-chloro-1,3-dihydroindol-2-one, 6.18 g of cyclohexanecarboxaldehyde and 4.93 ml of pyrrolidine in 250 ml of toluene is refluxed for 1 hour, the water formed being removed by means of a Dean-Stark apparatus. The reaction mixture is concentrated to about 90 ml and left to crystallize. The crystalline product formed is filtered off and washed with toluene and then with iso ether to give 9.7 g of the expected product after recrystallization from toluene. M.p.=203°–204° C.

B') 5-Chloro-3-(cyclohexylmethyl)-1,3-dihydroindol-2-one 1.08 g of sodium borohydride are added in portions to a mixture of 7.5 g of the compound obtained in the previous step, 60 ml of MeOH and 60 ml of THF and the reaction mixture is stirred for 30 minutes at RT. The solvent is concentrated under vacuum, the residue is extracted with AcOEt, the organic phase is washed with a saturated solution of NaCl and with water and dried over sodium sulfate and the solvent is evaporated off under vacuum. The residue is chromatographed on silica using DCM and then a DCM/AcOEt mixture (90/10; v/v) as the eluent to give 3.76 g of the expected product after crystallization from a DCM/iso ether mixture. M.p.=152°–153° C.

C') 5-Chloro-3-(cyclohexylmethyl)-1,3-dihydro-3-hydroxyindol-2-one 0.083 g of sodium hydride as a 60% dispersion in oil is added to a solution of 0.5 g of the compound obtained in the previous step in 30 ml of THF and the mixture is stirred for 10 minutes at RT. 0.22 ml of dimethyl disulfide is then introduced and the mixture is stirred for 1 hour at RT. 200 ml of water are added to the reaction mixture and the precipitate formed is filtered off and washed with water and then with iso ether to give 0.45 g of the expected product.

Preparation 20

5-Chloro-3-(cyclohexylmethyl)-1,3-dihydro-3-(methylamino)indol-2-one

A) 3,5-Dichloro-3-(cyclohexylmethyl)-1,3-dihydroindol-2-one

A solution of 1 g of the compound obtained in Preparation 19 in 5 ml of DCM is cooled to +4° C. and 0.56 ml of pyridine and then 0.4 ml of thionyl chloride are added. After stirring for 3 hours, the reaction mixture is chromatographed directly on silica using DCM and then a DCM/AcOEt mixture (95/5; v/v) as the eluent to give 1.1 g of the expected product, which is used as such in the next step.

B) 5-Chloro-3-(cyclohexylmethyl)-1,3-dihydro-3-(methylamino)indol-2-one 0.33 ml of an 8.03M solution of methylamine in EtOH is added at RT to a solution of 0.4 g of the compound obtained in the previous step in 10 ml of DCM and the mixture is stirred for 3 hours at RT. It is concentrated under vacuum, the residue is taken up with a 5% solution of sodium hydrogencarbonate, extracted with AcOEt, washed with a saturated solution of NaCl and with water and dried over sodium sulfate and the solvent is evaporated off under vacuum. The residue is chromatographed on silica using DCM and then a DCM/AcOEt mixture (60/40; v/v) as the eluent to give 0.225 g of the expected product after crystallization from a DCM/iso ether mixture. M.p.=168°–169° C.

Preparation 21

5-Chloro-3-[(2-cyanoethyl)amino]-3-(cyclohexylmethyl)-1,3-dihydroindol-2-one 1.33 ml of triethylamine and then 0.412 g of 3-aminopropionitrile fumarate are added at RT to a solution of 0.960 g of the compound obtained in step A of Preparation 20 in 5 ml of DCM and the reaction mixture is heated at 50° C. for 18 hours. It is concentrated under vacuum, the residue is taken up with a 5% solution of sodium carbonate, extracted with AcOEt, washed with a saturated solution of NaCl and with water and dried over sodium sulfate and the solvent is evaporated off under vacuum to give 0.5 g of the expected product after crystallization from AcOEt. M.p.= 208°–209° C.

Preparation 22

3-Benzyl-5-chloro-1,3-dihydro-3-hydroxyindol-2-one

A suspension of 10 g of 5-chloroisatin in 150 ml of THF is cooled to +4° C., 220 ml of a 1M solution of benzylmagnesium chloride in ether are added dropwise and the mixture is stirred for 3 hours at RT. 500 ml of a saturated solution of ammonium chloride are added and the solvents are concentrated under vacuum. The aqueous phase is extracted with AcOEt, the organic phase is washed with a saturated solution of NaCl and with water and dried over sodium sulfate and the solvent is evaporated off under vacuum to give 5.6 g of the expected product after crystallization from a THF/AcOEt mixture. M.p.=204°–205° C.

Preparation 23

3-Benzyl-5-chloro-1,3-dihydro-3-(methylamino)-indol-2-one

A) 3-Benzyl-3,5-dichloro-1,3-dihydroindol-2-one

A suspension of 4.63 g of the compound obtained in Preparation 22 in 25 ml of THF is cooled to +4° C. and 2.8 ml of pyridine and then 2 ml of thionyl chloride are added. After stirring for 3 hours at +4° C., the reaction mixture is concentrated under vacuum. The residue is chromatographed on silica using DCM and then a DCM/AcOEt mixture (97/3; v/v) as the eluent to give 1.2 g of the expected product, which is used as such in the next step.

B) 3-Benzyl-5-chloro-1,3-dihydro-3-(methylamino) indol2-one 1.02 ml of an 8.03M solution of methylamine in EtOH are added at RT to a solution of 1.2 g of the compound obtained in the previous step in 3 ml of DCM and the mixture is stirred for 6 hours at RT. 50 ml of water are added to the reaction mixture, extraction is carried out with AcOEt, the organic phase is washed with a saturated solution of NaCl and with water and dried over sodium sulfate and the solvent is evaporated off under vacuum. The residue is chromatographed on silica using DCM and then a DCM/AcOEt mixture (60/40; v/v) as the eluent to give 0.8 g of the expected product after crystallization from a DCM/iso ether mixture. M.p.=196° C.

Preparations 24 and 25

5-Chloro-3-(2-chlorophenyl)-1,3-dihydro-3-[[(1S)-2-hydroxy-1-phenylethyl]amino]indol-2-one, isomer A and isomer B A mixture of 5 g of the compound obtained in step C of Preparation 2, 3.83 g of (S)-(+)-2-phenylglycinol and 100 ml of chloroform is stirred for 3 days at RT. The reaction mixture is poured into a saturated solution of potassium carbonate and extracted with AcOEt and the insoluble compound at the interphase (isomer B: compound of Preparation 25) is filtered off. After decantation of the filtrate, the organic phase is washed 4 times with water and dried over sodium sulfate and the solvent is evaporated off under vacuum. The residue is chromatographed on silica using a DCM/AcOEt mixture (80/20; v/v) as the eluent. One isomer is separated out:

the less polar isomer, A: compound of Preparation 24. m=2.3 g. M.p.=170°–172° C. after crystallization from a DCM/iso ether mixture. $\alpha_D^{25}$=+263°(c=0.38; chloroform). Elution with a DCM/MeOH mixture (50/50; v/v) gives the other isomer:

the more polar isomer, B: compound of Preparation 25. m=1.64 g (insoluble material and chromatography). M.p.=294° C. after recrystallization from an MeOH/THF mixture. $\alpha_D^{25}$=−31.8°(c=0.21; DMF).

Preparations 26 and 27

5-Chloro-3-(2-chlorophenyl)-1,3-dihydro-3-[[(1R)-2-hydroxy-1-phenylethyl]amino]indol-2-one, isomer A and isomer B A mixture of 5 g of the compound obtained in step C of Preparation 2, 3.83 g of (R)-(−)-2-phenylglycinol and 200 ml of chloroform is stirred for 12 hours at RT. The insoluble compound (isomer B: compound of Preparation 27) is filtered off. The filtrate is concentrated under vacuum and the residue is chromatographed on silica using a gradient of a DCM/AcOEt mixture (from 80/20; v/v to 70/30; v/v) as the eluent. The two isomers are separated out:

the less polar isomer, A: compound of Preparation 26. m=2.43 g. M.p.=168° C. after crystallization from a DCM/iso ether mixture. $\alpha_D^{25}$=−268° (c=0.28; chloroform);

the more polar isomer, B: compound of Preparation 27. The insoluble compound obtained above is suspended in 500 ml of AcOEt and washed 6 times with a 5% solution of sodium carbonate. The insoluble compound is filtered off again, combined with the more polar compound obtained after chromatography and recrystallized from an MeOH/THF mixture. m=1.49 g. M.p.=293°–298° C. $\alpha_D^{25}$=+39.4°(c=0.2; DMF).

Preparation 28

3-Amino-5-chloro-3-(2-chlorophenyl)-1,3-dihydroindol-2-one, (+) isomer

A solution of 2.12 g of the compound obtained in Preparation 24 (isomer A) in 40 ml of DCM and 20 ml of MeOH is cooled in an ice bath, 2.48 g of lead tetraacetate are added and the reaction mixture is stirred for 40 minutes at 0° C. A saturated solution of sodium hydrogencarbonate is added to the reaction mixture, the organic solvents are concentrated under vacuum, the aqueous phase is extracted with AcOEt, the organic phase is washed with water and dried over sodium sulfate and the solvent is evaporated off under vacuum. The residue is taken up with 80 ml of a 5N solution of HCl, 10 ml of ether are added and the mixture is stirred for 10 minutes at RT. After decantation, the aqueous phase is washed twice with ether, rendered alkaline by the addition of a 5% solution of potassium carbonate and extracted with AcOEt, the organic phase is washed with water and with a saturated solution of NaCl and dried over sodium sulfate and the solvent is evaporated off under vacuum. The residue is chromatographed on silica using a DCM/AcOEt mixture

Preparation 29

3-Amino-5-chloro-3-(2-chlorophenyl)-1,3-dihydroindol-2-one, (−) isomer

This compound is prepared according to the procedure described in Preparation 28 from 2.3 g of the compound obtained in Preparation 26 (isomer A) and 2.72 g of lead tetraacetate in 40 ml of DCM and 20 ml of MeOH. Chromatography on silica using a DCM/AcOEt mixture (75/25; v/v) as the eluent gives 0.76 g of the expected product after crystallization from a DCM/iso ether mixture. M.p.=175°–176° C. $\alpha_D^{25}$=−121°(c=0.26; chloroform).

Preparation 30

5-Chloro-3-(2-chlorophenyl)-1,3-dihydro-3-(isopentylamino)indol-2-one

A mixture of 1 g of the compound obtained in step C of Preparation 2, 0.468 g of isopentylamine and 20 ml of chloroform is stirred for 1 hour at RT. The reaction mixture is washed with a 5% solution of sodium carbonate; then, after decantation, the organic phase is dried over sodium sulfate and the solvent is evaporated off under vacuum. The residue is chromatographed on silica using a DCM/AcOEt mixture (95/5; v/v) as the eluent to give 0.78 g of the expected product after crystallization from a DCM/iso ether/hexane mixture. M.p.=152° C.

Preparation 31

5-Chloro-3-(2-chlorophenyl)-3-[(1-ethoxycarbonylpiperid-4-yl)amino]-1,3-dihydroindol-2-one A mixture of 5 g of the compound obtained in step C of Preparation 2, 2.55 g of ethyl 4-aminopiperidine-1-carboxylate, 1.91 g of DIPEA and 100 ml of chloroform is stirred for 2 hours at RT. The reaction mixture is washed with water; then, after decantation, the organic phase is dried over sodium sulfate and the solvent is evaporated off under vacuum. The residue is chromatographed on silica using a DCM/AcOEt mixture (90/10; v/v) as the eluent to give 5 g of the expected product after crystallization from a DCM/iso ether mixture. M.p.=204° C.

Preparation 32

5-Chloro-3-(2-chlorophenyl)-1,3-dihydro-3-[[2-(3-methoxyphenyl)ethyl]amino]indol-2-one 1.63 ml of 3-methoxyphenethylamine are added at RT to a solution of 2 g of the compound obtained in step C of Preparation 2 in 40 ml of DCM and the reaction mixture is stirred for 1 hour. It is washed with a 5% solution of potassium carbonate; then, after decantation, it is dried over sodium sulfate and the solvent is evaporated off under vacuum. The residue is chromatographed on silica using DCM and then a DCM/AcOEt mixture (95/5; v/v) as the eluent to give 2 g of the expected product after crystallization from a DCM/iso ether mixture. M.p.=155°–160° C.

Preparation 33

5-Chloro-3-(2-chlorophenyl)-1,3-dihydro-3-[[2-(pyrid-2-yl)ethyl]amino]indol-2-one A mixture of 5 g of the compound obtained in step C of Preparation 2, 3.56 g of 2-(2-aminoethyl)-pyridine and 50 ml of chloroform is stirred for 2 hours at RT. The reaction mixture is washed with water; then, after decantation, the organic phase is dried over sodium sulfate and the solvent is evaporated off under vacuum. The residue is chromatographed on alumina using a DCM/AcOEt mixture (50/50; v/v) as the eluent to give 3.3 g of the expected product after crystallization from a DCM/iso ether mixture. M.p.=178° C.

Preparation 34

5-Chloro-3-(2-chlorophenyl)-1,3-dihydro-3-[(2-hydroxyethyl)amino]indol-2-one

A solution of 1.03 g of 2-aminoethanol and 3.45 g of triethylamine in 10 ml of chloroform is added at RT to a suspension of 6 g of the compound obtained in step C of Preparation 2 in 20 ml of chloroform and the reaction mixture is stirred for 3 hours at RT. It is partially concentrated under vacuum and the precipitate formed is filtered off to give 4 g of the expected product after crystallization from a THF/AcOEt mixture. M.p.=198°–200° C.

Preparation 35

5-Chloro-3-(2-chlorophenyl)-1,3-dihydro-3-[[2-(trimethylsilyloxy)ethyl]amino]indol-2-one A mixture of 1.5 g of the compound obtained in Preparation 34, 0.72 g of hexamethyldisilane, 0.03 g of zinc chloride and 15 ml of acetonitrile is heated at 60° C. for 4 hours. The reaction mixture is concentrated under vacuum, the residue is extracted with AcOEt, the organic phase is washed twice with water and with a saturated solution of NaCl and dried over sodium sulfate and the solvent is evaporated off under vacuum to give 1.084 g of the expected product after trituration in iso ether followed by filtration. Said product is used as such in EXAMPLE 114.

Preparation 36

5-Chloro-3-(2-chlorophenyl)-1,3-dihydro-3-[[2-[2-(dimethylamino)ethoxy]ethyl]amino]indol-2-one A) 2-[2-(tert-Butoxycarbonylamino)ethoxy]ethanol 21.8 g of di-tert-butyl dicarbonate are added in portions at RT to a solution of 10.5 g of 2-(2-aminoethoxy)ethanol in 50 ml of 1,4-dioxane and the reaction mixture is stirred for 2 hours at RT. It is poured into water and extracted three times with AcOEt, the organic phase is washed twice with 20 ml of water and dried over sodium sulfate and the solvent is evaporated off under vacuum to give 18.5 g of the expected product in the form of an oil, which is used as such in the next step.

B) 2-[2-(tert-Butoxycarbonylamino)ethoxy]ethyl methanesulfonate

A solution of 18.5 g of the compound obtained in the previous step and 9.2 g of triethylamine in 100 ml of DCM is cooled to 0° C. and a solution of 10.4 g of methanesulfonyl chloride in 15 ml of DCM is added dropwise, the temperature being kept below 10° C. After stirring for two days at RT, the reaction mixture is concentrated under vacuum, the residue is taken up with AcOEt, the organic phase is washed with water and with a saturated solution of NaCl and dried over sodium sulfate and the solvent is evaporated off under vacuum to give 24.3 g of the expected product in the form of an oil, which is used as such in the next step.

(70/30; v/v) as the eluent to give 1.25 g of the expected product after crystallization from a DCM/iso ether mixture. M.p.=174°–176° C. $\alpha_D^{25}$=+118°(c=0.47; chloroform).

C) N,N-Dimethyl-2-[2-(tert-butoxycarbonylamino) ethoxy]-ethylamine

A solution of 8.0 g of the compound obtained in the previous step in 100 ml of ether is cooled to 0° C. and 7.5 g of a 33% solution of dimethylamine in EtOH, diluted in 10 ml of ether, are added dropwise. The reaction mixture is stirred for 4 days at RT and concentrated under vacuum. The residue is taken up with a 1N solution of HCl, the acid aqueous phase is washed with ether, rendered alkaline by the addition of potassium carbonate and extracted 3 times with ether and once with AcOEt, the combined organic phases are dried over sodium sulfate and the solvents are evaporated off under vacuum to give 1.15 g of the expected product in the form of an oil, which is used as such in the next step.

D) 5-Chloro-3-(2-chlorophenyl)-1,3-dihydro-3-[[2-[2-(dimethylamino)ethoxy]ethyl]amino]indol-2-one A mixture of 1.15 g of the compound obtained in the previous step and 10 ml of TFA is stirred for 90 minutes at 0° C. and concentrated under vacuum. The residue is dissolved in a solution of 2 g of triethylamine in 30 ml of chloroform and this solution is added dropwise at RT to a solution of 1.76 g of the compound obtained in step C of Preparation 2 in 30 ml of chloroform. The reaction mixture is stirred for 3 hours and concentrated under vacuum. The residue is taken up with a 5% solution of potassium carbonate and extracted 3 times with AcOEt, the organic phase is washed with water and with a saturated solution of NaCl and dried over sodium sulfate and the solvent is evaporated off under vacuum. The residue is chromatographed on alumina using a DCM/MeOH mixture (98/2; v/v) as the eluent to give 1.15 g of the expected product after crystallization from a DCM/iso ether mixture. M.p.=165°–168° C.

Preparation 37

3-[[2-[2-(tert-Butoxycarbonylamino)ethoxy]-ethyl]amino]-5-chloro-3-(2-chlorophenyl)-1,3-dihydroindol-2-one

A) 2-[2-(tert-Butoxycarbonylamino)ethoxy]ethyl azide

A mixture of 12.4 g of the compound obtained in step B of Preparation 36, 2.9 g of sodium azide and 50 ml of DMSO is stirred for 18 hours at RT and then heated at 80° C. for 4 hours. The reaction mixture is poured into water and extracted with AcOEt, the organic phase is dried over sodium sulfate and the solvent is evaporated off under vacuum. The residue is chromatographed on silica using a hexane/AcOEt mixture (70/30; v/v) as the eluent to give 7.4 g of the expected product in the form of an oil, which is used as such in the next step.

B) 2-[2-(tert-Butoxycarbonylamino)ethoxy] ethylamine

A mixture of 7.4 g of the compound obtained in the previous step, 1.5 g of Raney® nickel, 1.5 ml of hydrazine monohydrate and 60 ml of EtOH is stirred for 4 hours at RT. A further 1.5 ml of hydrazine monohydrate are added and the mixture is stirred for 2 hours at RT. The catalyst is filtered off and washed with EtOH and the filtrate is concentrated under vacuum to give 6.22 g of the expected product, which is used as such in the next step.

C) 3-[[2-[2-(tert-Butoxycarbonylamino)ethoxy] ethyl]-amino]-5-chloro-3-(2-chlorophenyl)-1,3-dihydroindol-2-one A solution of 6.22 g of the compound obtained in the previous step and 2 g of triethylamine in 30 ml of chloroform is added in 2 hours at RT to a suspension of 7.0 g of the compound prepared in step C of Preparation 2 in 40 ml of chloroform and the reaction mixture is stirred for 3 hours at RT. It is concentrated under vacuum, the residue is taken up with a 5% solution of potassium carbonate and extracted with AcOEt, the organic phase is washed with water and with a saturated solution of NaCl and dried over sodium sulfate and the solvent is evaporated off under vacuum. The residue is chromatographed on silica using a DCM/AcOEt mixture (50/50; v/v) as the eluent to give 7.3 g of the expected product after crystallization from a DCM/iso ether mixture. M.p.=138°–140° C.

Preparation 38

5-Chloro-3-(2-chlorophenyl)-3-[[2-(diethylamino) ethyl]amino]-1,3-dihydroindol-2-one A solution of 1.13 ml of N,N-diethylethylenediamine and 5.82 ml of triethylamine in 20 ml of DCM is added dropwise at RT to a suspension of 5 g of the compound obtained in step C of Preparation 2 in 30 ml of DCM and the reaction mixture is stirred for 3 hours at RT. It is concentrated under vacuum, the residue is taken up with a 5% solution of sodium carbonate and extracted with AcOEt, the organic phase is washed with a saturated solution of NaCl and with water and dried over sodium sulfate and the solvent is evaporated off under vacuum. The residue is chromatographed on silica using DCM and then a DCM/MeOH mixture (70/30; v/v) as the eluent to give 2.21 g of the expected product.

NMR spectrum at 200 MHz in DMSO-$d_6$
0.8 ppm: t: 6H
2.0 to 2.6 ppm: m: 8H
2.8 ppm: mt: 1H
6.5 to 8.2 ppm: m: 7H
10.75 ppm: s: 1H

Preparation 39

5-Chloro-3-(2-chlorophenyl)-3-[N-[2-(diethylamino) ethyl]-N-methylamino]-1,3-dihydroindol-2-one A mixture of 5 g of the compound obtained in step C of Preparation 2, 3.8 g of N,N-diethyl-N'-methylethylenediamine and 100 ml of chloroform is stirred for 18 hours at RT. The reaction mixture is washed with water, the organic phase is dried over sodium sulfate and the solvent is evaporated off under vacuum. The residue is chromatographed on alumina using a DCM/MeOH mixture (97/3; v/v) as the eluent to give 3.6 g of the expected product after crystallization from iso ether. M.p.=140° C.

Preparation 40

5-Chloro-3-(2-chlorophenyl)-1,3-dihydro-3-[[2-(diisopropylamino)ethyl]amino]indol-2-one A mixture of 5 g of the compound obtained in step C of Preparation 2, 4.3 g of N,N-diisopropyl-ethylenediamine and 50 ml of chloroform is stirred for 18 hours at RT. The reaction mixture is washed with water, the organic phase is dried over sodium sulfate and the solvent is evaporated off under vacuum. The residue is taken up with iso ether and, after trituration, the solid formed is filtered off to give 4.2 g of the expected product, which is used as such in EXAMPLE 159.

Preparation 41

5-Chloro-3-(2-chlorophenyl)-1,3-dihydro-3-[N-methyl-N-[3-(dimethylamino)propyl]amino]indol-2-one A mixture of 3.57 g of the compound obtained in step C of Preparation 2, 1.16 g of N,N-dimethyl-N'-methylpropane- 1,3-diamine, 1.01 g of triethylamine and 40 ml of chloroform is stirred overnight at RT. After concentration under vacuum, the residue is taken up with a 5% solution of sodium carbonate and extracted with AcOEt, the organic phase is washed with water and with a saturated solution of NaCl and dried over sodium sulfate and the solvent is evaporated off under vacuum. The residue is chromatographed on alumina using a DCM/MeOH mixture (98/2; v/v) as the eluent to give 2.36 g of the expected product, which is used as such in EXAMPLE 161.

Preparation 42

3-[[4-(tert-Butoxycarbonylamino)butyl]amino]-5-chloro-3-(2-chlorophenyl)-1,3-dihydroindol-2-one A) 3-[(4-Aminobutyl)amino]-5-chloro-3-(2-chlorophenyl)-1,3-dihydroindol-2-one A solution of 5 g of the compound obtained in step C of Preparation 2 in 50 ml of chloroform and 15 ml of THF is added dropwise at RT to a solution of 5.6 ml of 1,4-diaminobutane in 10 ml of chloroform. The reaction mixture is stirred for 3 hours at RT and partially concentrated and the precipitate formed is filtered off to give 4.48 g of the expected product.

NMR spectrum at 200 MHz in DMSO-$d_6$
1.3 ppm: mt: 4H
2.5 ppm: mt: 4H
4.2 ppm: broad signal: 4H
6.5 to 8.2 ppm: m: 7H B) 3-[[4-(tert-Butoxycarbonylamino)butyl]amino]-5-chloro-3-(2-chlorophenyl)-1,3-dihydroindol-2-one 1.95 ml of triethylamine and then 3.074 g of di-tert-butyl dicarbonate are added at RT to a suspension of 5.13 g of the compound obtained in the previous step in 150 ml of THF and the mixture is stirred for 20 hours at RT. An insoluble material is filtered off and the filtrate is concentrated under vacuum. The residue is chromatographed on silica using DCM and then a DCM/AcOEt mixture (75/25; v/v) as the eluent to give 2.8 g of the expected product after crystallization from a DCM/iso ether mixture. M.p.=175°–176° C.

Preparation 43

3-[[5-(tert-Butoxycarbonylamino)pentyl]amino]-5-chloro-3-(2-chlorophenyl)-1,3-dihydroindol-2-one A) 5-(tert-Butoxycarbonylamino)pentyl methanesulfonate A solution of 28.6 g of 5-(tert-butoxycarbonylamino)pentan-1-ol in 100 ml of pyridine is cooled to 0° C. and 16.2 g of methanesulfonyl chloride are added dropwise in 3 hours at 0° C. The reaction mixture is stirred overnight at RT and concentrated under vacuum. The residue is taken up with water and extracted with AcOEt, the organic phase is washed three times with water, three times with a 5% solution of potassium hydrogensulfate, three times with water and with a saturated solution of NaCl and dried over sodium sulfate and the solvent is evaporated off under vacuum to give 39 g of the expected product, which is used as such in the next step.

B) 5-(tert-Butoxycarbonylamino)pentyl azide

A mixture of 39 g of the compound obtained in the previous step, 9 g of sodium azide and 80 ml of DMSO is heated at 80° C. for 5 hours. The reaction mixture is poured into water and extracted with AcOEt, the organic phase is washed with water and with a saturated solution of NaCl and dried over sodium sulfate and the solvent is evaporated off under vacuum. The residue is chromatographed on silica using a hexane/AcOEt mixture (90/10; v/v) as the eluent to give 7.8 g of the expected product, which is used as such in the next step.

C) 5-(tert-Butoxycarbonylamino)pentylamine 1.5 ml of hydrazine monohydrate are added to a mixture of 7.8 g of the compound obtained in the previous step, 1.5 g of Raney® nickel and 60 ml of EtOH and the reaction mixture is stirred for 1 hour 30 minutes at RT. A further 1.5 ml of hydrazine monohydrate are added and the mixture is stirred for 1 hour 30 minutes at RT. The catalyst is filtered off and the filtrate is concentrated under vacuum. The residue is taken up with water and acidified to pH 1 by the addition of a 1N solution of HCl, the aqueous phase is washed with ether, rendered alkaline by the addition of potassium carbonate and extracted four times with ether, the organic phase is washed with water and with a saturated solution of NaCl and dried over sodium sulfate and the solvent is evaporated off under vacuum to give 3.0 g of the expected product, which is used as such in the next step.

D) 3-[[5-(tert-Butoxycarbonylamino)pentyl]amino]-5-chloro-3-(2-chlorophenyl)-1,3-dihydroindol-2-one A mixture of 2.65 g of the compound obtained in step C of Preparation 2, 3 g of the compound obtained in the previous step and 30 ml of chloroform is stirred for 3 hours at RT. The reaction mixture is concentrated under vacuum, the residue is taken up with water and extracted with AcOEt, the organic phase is washed with a 5% solution of potassium carbonate, with water and with a saturated solution of NaCl and dried over sodium sulfate and the solvent is partially evaporated off under vacuum. The crystalline product formed is filtered off to give 2.14 g of the expected product, a sample of which is recrystallized from a THF/iso ether mixture. M.p.=185° C.

Preparation 44

5-Chloro-3-(2-chlorophenyl)-1,3-dihydro-3-[[2-(piperid-1-yl)ethyl]amino]indol-2-one 3.23 g of 1-(2-aminoethyl)piperidine are added at RT to a solution of 5 g of the compound obtained in step C of Preparation 2 in 120 ml of chloroform and the reaction mixture is stirred for 2 hours at RT. It is washed with water and, after decantation, the organic phase is dried over sodium sulfate and the solvent is evaporated off under vacuum to give 4.8 g of the expected product after crystallization from an iso ether/hexane/pentane mixture; it is used as such in EXAMPLE 167.

Preparations 45 and 46

3-[[2-[4-(Benzyloxycarbonyl)piperazin-1-yl]-ethyl]amino]-5-chloro-3-(2-chlorophenyl)-1,3-dihydroindol-2-one (Preparation 45) and 3-[4-[2-(benzyloxycarbonylamino)ethyl]piperazin-1-yl]-5-chloro-3-(2-chlorophenyl)-1, 3-dihydroindol-2-one (Preparation 46)

A) 5-Chloro-3-(2-chlorophenyl)-1,3-dihydro-3-[[2-(piperazin-1-yl)ethyl]amino]indol-2-one and 3-[4-(2-aminoethyl)piperazin-1-yl]-5-chloro-3-(2-chlorophenyl)-1,3-dihydroindol-2-one A solution of 3 g of the compound obtained in step C of Preparation 2 in 30 ml of chloroform and 20 ml of THF is added in 1 hour at RT to a solution of 4.35 g of 1-(2-aminoethyl)piperazine in 70 ml of chloroform. After stirring for 1 hour at RT, the reaction mixture is concentrated under vacuum. The residue is taken up with a 5% solution of potassium carbonate and extracted with AcOEt, the organic phase is washed with water and with a saturated solution of NaCl and dried over sodium sulfate and the solvent is evaporated off under vacuum to give 3.6 g of a mixture of the two products in the form of an oil, which is used as such in the next step.

B) 3-[[2-[4-(Benzyloxycarbonyl)piperazin-1-yl]ethyl]-amino]-5-chloro-3-(2-chlorophenyl)-1,3-dihydroindol-2-one (Preparation 45) and 3-[4-[2-(benzyloxycarbonylamino)ethyl]piperazin-1-yl]-5-chloro-3-(2-chlorophenyl)-1,3-dihydroindol-2-one (Preparation 46)

A solution of 3.6 g of the mixture of the two compounds obtained in the previous step in 15 ml of DCM is cooled to 0° C. and 1.1 g of DIPEA and then 1.45 g of benzyl chloroformate are added. The reaction mixture is stirred for 60 hours at RT and concentrated under vacuum. The residue is extracted with AcOEt, the organic phase is washed with water and with a saturated solution of NaCl and dried over sodium sulfate and the solvent is evaporated off under vacuum. The residue is chromatographed on silica using a DCM/AcOEt mixture (90/10; v/v) as the eluent to give 0.86 g of the compound of Preparation 45. Elution with AcOEt then gives 1.7 g of the compound of Preparation 46.

NMR spectrum at 200 MHz in DMSO-d. of the compound of Preparation 45

2.0 to 3.6 ppm: m: 13H 5.1 ppm: s: 2H 6.6 to 8.2 ppm: m: 12H 10.8 ppm: s: 1H

NMR spectrum at 200 MHz in DMSO-$d_6$ of the compound of Preparation 46

2.0 to 3.0 ppm: m: 10H 3.15 ppm: qd: 2H 5.05 ppm: s: 2H 6.7 to 8.2 ppm: m: 13H 10.85 ppm: s: 1H The compound of Preparation 45 can also be obtained by following the two steps of the method described below.

A') 4-(2-Aminoethyl)-1-(benzyloxycarbonyl)piperazine 8.21 g of benzaldehyde are added to a solution of 10 g of 1-(2-aminoethyl)piperazine in 125 ml of toluene and the mixture is refluxed for 3 hours, the water formed being removed by means of a Dean-Stark apparatus. The reaction mixture is concentrated under vacuum, the residue is taken up with 100 ml of DCM, 13.45 ml of DIPEA are added and 11.03 ml of benzyl chloroformate are added dropwise. The reaction mixture is stirred overnight at RT and concentrated under vacuum. The residue is taken up with a saturated solution of potassium hydrogensulfate and stirred vigorously for 4 hours at RT. The aqueous phase is washed with ether, rendered alkaline to pH 9–10 by the addition of concentrated NaOH, saturated by the addition of NaCl and extracted with chloroform, the organic phase is dried over sodium sulfate and the solvent is evaporated off under vacuum to give 18.78 g of the expected product, which is used as such in the next step.

B') 3-[[2-[4-(Benzyloxycarbonyl)piperazin-1-yl]ethyl]-amino]-5-chloro-3-(2-chlorophenyl)-1,3-dihydroindol-2-one A solution of 1.77 g of the compound obtained in the previous step and 3.1 ml of triethylamine in 10 ml of chloroform is added dropwise at RT to a solution of 2 g of the compound obtained in step C of Preparation 2 in 20 ml of chloroform and 3 ml of THF and the mixture is stirred for 3 hours at RT. It is concentrated under vacuum, the residue is extracted with AcOEt, the organic phase is washed with a saturated solution of NaCl and with water and dried over sodium sulfate and the solvent is evaporated off under vacuum. The residue is chromatographed on silica using DCM and then a DCM/AcOEt mixture (40/60; v/v) as the eluent to give 2 g of the expected product.

Preparation 47

5-Chloro-3-(2-chlorophenyl)-1,3-dihydro-3-[[2-(morpholin-4-yl)ethyl]amino]indol-2-one A mixture of 5 g of the compound obtained in step C of Preparation 2, 3.5 g of 4-(2-aminoethyl)-morpholine and 120 ml of chloroform is stirred for 2 hours at RT. The reaction mixture is washed with water and, after decantation, the organic phase is dried over sodium sulfate and the solvent is evaporated off under vacuum to give 5.2 g of the expected product after trituration in a hexane/pentane mixture followed by filtration. It is used as such.

Preparation 48

5-Chloro-3-(2-chlorophenyl)-1,3-dihydro-3-[[3-(morpholin-4-yl)propyl]amino]indol-2-one A solution of 3.57 g of the compound obtained in step C of Preparation 2 in 100 ml of chloroform is cooled to 0° C. and a solution of 1.44 g of 4-(3-aminopropyl)morpholine and 2.02 g of triethylamine in 10 ml of chloroform is added dropwise in 10 minutes. The reaction mixture is stirred overnight at RT and concentrated under vacuum. The residue is taken up with water, rendered alkaline to pH 10 by the addition of potassium carbonate and extracted with AcOEt, the organic phase is washed with water and with a saturated solution of NaCl and dried over sodium sulfate and the solvent is evaporated off under vacuum. The residue is chromatographed on silica using an AcOEt/MeOH mixture (93/7; v/v) as the eluent to give 2.8 g of the expected product in the form of a foam after crystallization from a DCM/hexane mixture followed by drying at 90° C. under vacuum.

NMR spectrum at 200 MHz at DMSO-$d_6$ 1.6 ppm: mt: 2H 2.1 to 2.6 ppm: m: 8H 3.35 ppm: t: 1H 3.55 ppm: t: 4H 6.6 to 8.3 ppm: m: 7H 10.8 ppm: s: 1H Preparation 49

3-[[2-(tert-Butoxycarbonylamino)-2-methylpropyl]amino]-5-chloro-3-(2-chlorophenyl)-1,3-dihydroindol-2-one A solution of 1.17 ml of 1,2-diamino-2-methylpropane and 2.32 ml of triethylamine in 15 ml of chloroform is added dropwise at RT to a solution of 2 g of the compound obtained in step C of Preparation 2 in 20 ml of chloroform and the reaction mixture is stirred for 3 hours at RT. It is concentrated under vacuum, the residue is dissolved in 15 ml of DCM, 1.57 ml of triethylamine and then 1.45 g of di-tert-butyl dicarbonate are added and the reaction mixture is stirred for 18 hours at RT. It is concentrated under vacuum, the residue is extracted with AcOEt, the organic phase is washed with a saturated solution of NaCl and with water and dried over sodium sulfate and the solvent is evaporated off under vacuum. The residue is chromatographed on silica using DCM and then a DCM/MeOH mixture (85/15; v/v) as the eluent to give 1.4 g of the expected product after crystallization from a DCM/iso ether mixture. M.p.=164° C.

Preparation 50

5-Chloro-3-(2-chlorophenyl)-3-[[(diethylaminocarbonyl)methyl]amino]-1,3-dihydroindol-2-one A) tert-Butyl N-[5-chloro-3-(2-chlorophenyl)-2,3-dihydro-2-oxoindol-3-yl]glycinate A mixture of 6 g of the compound obtained in step C of Preparation 2, 4 g of tert-butyl glycinate and 100 ml of chloroform is stirred for 18 hours at RT. The reaction mixture is washed with water and, after decantation, the organic phase is dried over sodium sulfate and the solvent is evaporated off under vacuum. The residue is chromatographed on silica using a DCM/AcOEt mixture (95/5; v/v) as the eluent to give 2.7 g of the expected product after crystallization from a DCM/iso ether mixture. M.p.=217° C.

B) N-[5-Chloro-3-(2-chlorophenyl)-2,3-dihydro-2-oxoindol-3-yl]glycine 12 ml of TFA are added to a mixture of 2.7 g of the compound obtained in the previous step in 12 ml of DCM and the reaction mixture is stirred for 18 hours at RT. It is concentrated under vacuum at 35° C., the residue is taken up with an ether/hexane mixture and the precipitate formed is filtered off to give 2.5 g of the expected product, which is used as such in the next step.

C) 5-Chloro-3-(2-chlorophenyl)-3-[[(diethylaminocarbonyl)methyl]amino]-1,3-dihydroindol-2-one 1.3 g of BOP are added to a solution of 1 g of the compound obtained in the previous step and 0.66 g of diethylamine in 10 ml of DMF and the mixture is stirred for 18 hours at RT. Water is added to the reaction mixture and the precipitate formed is filtered off and washed with water. The precipitate is dissolved in DCM, the organic phase is washed with water and dried over sodium sulfate and the solvent is evaporated off under vacuum. The residue is chromatographed on silica using a DCM/AcOEt mixture (50/50; v/v) as the eluent to give 0.95 g of the expected product after crystallization from a DCM/iso ether mixture. M.p.=223° C.

Preparation 51

5-Chloro-3-(2-chlorophenyl)-3-[[2-(diethylaminocarbonyl)ethyl]amino]-1,3-dihydroindol-2-one A) tert-Butyl N-[5-chloro-3-(2-chlorophenyl)-2,3-dihydro-2-oxoindol-3-yl]-β-alaninate 3.2 g of tert-butyl β-alaninate hydrochloride and then 4.18 g of DIPEA are added at RT to a solution of 6 g of the compound obtained in step C of Preparation 2 in 100 ml of chloroform and the reaction mixture is stirred for 2 hours at RT. It is washed with water and, after decantation, the organic phase is dried over sodium sulfate and the solvent is evaporated off under vacuum. The residue is chromatographed on silica using a DCM/AcOEt mixture (85/15; v/v) as the eluent to give 5 g of the expected product after crystallization from a DCM/iso ether mixture. M.p.=188° C.

B) N-[5-Chloro-3-(2-chlorophenyl)-2,3-dihydro-2-oxoindol-3-yl]-β-alanine 4.7 g of the compound obtained in the previous step and 50 ml of TFA are mixed at 0° C. and the mixture is stirred for 5 hours, the temperature being allowed to rise to RT. The reaction mixture is concentrated under vacuum at 30° C., the residue is taken up with an ether/hexane mixture and the precipitate formed is filtered off to give 1.5 g of the expected product, which is used as such in the next step.

C) 5-Chloro-3-(2-chlorophenyl)-3-[[2-(diethylaminocarbonyl)ethyl]amino]-1,3-dihydroindol-2-one A solution of 1.5 g of the compound obtained in the previous step and 0.906 g of diethylamine in 20 ml of DMF is cooled to 0° C., 1.4 g of BOP are added and the mixture is stirred for 18 hours, the temperature being allowed to rise to RT. The reaction mixture is poured into water and the precipitate formed is filtered off. The precipitate is dissolved in AcOEt, the organic phase is washed with water and dried over sodium sulfate and the solvent is evaporated off under vacuum. The residue is chromatographed on silica using a DCM/AcOEt mixture (50/50; v/v) as the eluent to give 0.82 g of the expected product after crystallization from a DCM/iso ether mixture. M.p.=185° C.

Preparation 52

5-Chloro-3-(2-chlorophenyl)-3-[[3-(methoxycarbonyl)propyl]amino]-1,3-dihydroindol-2-one A mixture of 2 g of the compound obtained in step C of Preparation 2, 1.65 g of methyl 4-aminobuty-rate hydrochloride, 2.09 g of DIPEA and 20 ml of chloroform is stirred for 1 hour at RT. The reaction mixture is washed with a 5% solution of sodium carbonate and, after decantation, the organic phase is dried over sodium sulfate and the solvent is evaporated off under vacuum. The residue is chromatographed on silica using an AcOEt/hexane mixture (50/50; v/v) as the eluent to give 1.7 g of the expected product after crystallization from a DCM/iso ether mixture. M.p.=142° C.

Preparation 53

5-Chloro-3-(2-chlorophenyl)-3-[(cyanomethyl)-amino]-1,3-dihydroindol-2-one

A solution of 3 g of the compound obtained in step C of Preparation 2 in 20 ml of chloroform and 20 ml of THF is cooled to +4° C., a solution of 0.92 g of aminoacetonitrile hydrochloride and 4.6 ml of triethylamine in 20 ml of chloroform is added dropwise and the mixture is stirred for 3 hours, the temperature being allowed to rise to RT. 100 ml of water are added to the reaction mixture, the solvents are concentrated under vacuum, the aqueous phase is extracted with AcOEt, the organic phase is washed with a saturated solution of NaCl and with water and dried over sodium sulfate and the solvent is evaporated off under vacuum. The residue is chromatographed on silica using DCM and then a DCM/AcOEt mixture (95/5; v/v) as the eluent to give 1.2 g of the expected product. M.p.=240°–241° C.

Preparations 54 and 55

3-[[(1S)-5-(Benzyloxycarbonylamino)-1-(methoxycarbonyl)pentyl]amino]-5-chloro-3-(2-chlorophenyl)-1,3-dihydroindol-2-one, isomer A and isomer B A solution of 4.6 g of triethylamine in 30 ml of THF is added dropwise at RT to a mixture of 5.4 g of the compound obtained in step C of Preparation 2, 5 g of N-ε-(benzyloxycarbonyl)-L-lysine methyl ester hydrochloride and 30 ml of THF and the reaction mixture is stirred for 2 hours at RT. It is concentrated under vacuum, the residue is taken up with a 5% solution of sodium carbonate and extracted with AcOEt, the organic phase is washed with water and dried over sodium sulfate and the solvent is evaporated off under vacuum. The residue is chromatographed on silica using a gradient of a hexane/AcOEt mixture (from 95/5; v/v to 50/50; v/v) as the eluent. The two isomers are separated out:

the less polar isomer, A: compound of Preparation 54, which is rechromatographed on silica using a DCM/AcOEt mixture (60/40; v/v) as the eluent. $\alpha_D^{25}$=+105° (c=0.257; chloroform);

the more polar isomer, B: compound of Preparation 55, which is rechromatographed on silica using a DCM/AcOEt mixture (50/50; v/v) as the eluent. $\alpha_D^{25}$=−95.7° (c=0.279; chloroform).

Preparations 56 and 57

3-[[(1R)-5-(Benzyloxycarbonylamino)-1-(methoxycarbonyl)pentyl]amino]-5-chloro-3-(2-chlorophenyl)-1,3-dihydroindol-2-one, isomer A and isomer B These two compounds are prepared according to the procedure described in Preparations 54 and 55 from 4.1 g of the compound obtained in step C of Preparation 2 and 5.22 g of N-ε-(benzyloxycarbonyl)-D-lysine methyl ester hydrochloride in 40 ml of THF and 4.2 g of triethylamine in 30 ml of THF. Chromatography on silica using a gradient of a pentane/AcOEt mixture (from 95/5; v/v to 45/55; v/v) as the eluent separates out one isomer:

the less polar isomer, A: compound of Preparation 56. $\alpha_D^{25}$=−100.7 (c=0.275; chloroform).

The remaining product is rechromatographed on silica H using a gradient of a DCM/AcOEt mixture (from 94/6; v/v to 75/25; v/v) as the eluent to separate out the other isomer:

the more polar isomer, B: compound of Preparation 57. $\alpha_D^{25}$=+92.9° (c=0.254; chloroform).

Preparations 58 and 59

3-[[(1S)-5-(Benzyloxycarbonylamino)-1-(hydroxymethyl)pentyl]amino]-5-chloro-3-(2-chlorophenyl)-1,3-dihydroindol-2-one, isomer A and isomer B A) N-ε-(Benzyloxycarbonyl)-L-lysinol 5 g of N-ε-(benzyloxycarbonyl)-L-lysine methyl ester hydrochloride are added in 10 minutes to a suspension of 5 g of sodium borohydride in 100 ml of EtOH and the mixture is stirred overnight at RT. 10 ml of a 5N solution of HCl are added and the solvent is evaporated off under vacuum. The residue is taken up with water, the aqueous phase is rendered alkaline to pH 13 by the addition of concentrated NaOH and extracted with AcOEt, the organic phase is washed twice with water and with a saturated solution of NaCl and dried over sodium sulfate and the solvent is evaporated off under vacuum to give 3.58 g of the expected product, which is used as such.

B) 3-[[(1S)-5-(Benzyloxycarbonylamino)-1-(hydroxymethyl)pentyl]amino]-5-chloro-3-(2-chlorophenyl)-1,3-dihydroindol-2-one, isomer A and isomer B A solution of 3.50 g of the compound obtained in the previous step and 4 g of triethylamine in 40 ml of THF is added dropwise to a solution of 4.90 g of the compound obtained in step C of Preparation 2 in 50 ml of THF and the mixture is stirred for 2 hours at RT. A 5% solution of potassium carbonate is added, extraction is carried out with AcOEt, the organic phase is washed with water and with a saturated solution of NaCl and dried over sodium sulfate and the solvent is evaporated off under vacuum. The residue is chromatographed on silica using a DCM/AcOEt mixture (60/40; v/v) as the eluent to separate out one isomer:

the less polar isomer, A: compound of Preparation 58, which is rechromatographed on alumina using an AcOEt/MeOH mixture (97/3; v/v) as the eluent to give 2.4 g of the product in the form of an oil. $\alpha_D^{25}$=+174.3° (c=0.25; chloroform).

Elution in the 1st chromatography with a DCM/AcOEt mixture (20/80; v/v) separates out the other isomer:

the more polar isomer, B: compound of Preparation 59, which is taken up with a hexane/iso ether mixture and then, after filtration of the precipitate formed, crystallized from a DCM/iso ether mixture to give 1.3 g. M.p.=110° C. $\alpha_D^{25}$=−95.2° (c=0.25; chloroform).

Preparation 60

3-[[(1S)-5-(Benzyloxycarbonylamino)-1-[(trimethylsilyloxy)methyl]pentyl]amino]-5-chloro-3-(2-chlorophenyl)-1,3-dihydroindol-2-one A mixture of 2.1 g of the compound obtained in Preparation 58 (isomer A), 0.63 g of hexamethyldisilane, 0.025 g of zinc chloride and 20 ml of acetonitrile is heated at 60° C. overnight. It is concentrated under vacuum, the residue is extracted with AcOEt, the organic phase is rapidly washed twice with water and with a saturated solution of NaCl and dried over sodium sulfate and the solvent is evaporated off under vacuum to give the expected product, which is used as such in EXAMPLE 226.

Preparation 61

5-Chloro-3-(2-chlorophenyl)-1,3-dihydro-3-[2-(dimethylamino)acetamido]indol-2-one A mixture of 1.07 g of the compound obtained in Preparation 2, 0.32 ml of bromoacetyl bromide and 15 ml of benzene is refluxed for 1 hour. After cooling, the precipitate formed is filtered off. The precipitate is taken up with 10 ml of DCM, 3 ml of a 30% solution of dimethylamine in EtOH are added in 1 hour and the reaction mixture is stirred. It is concentrated under vacuum, the residue is taken up with a 5% solution of sodium carbonate and extracted with AcOEt, the organic phase is washed with water and with a saturated solution of NaCl and dried over sodium sulfate and the solvent is evaporated off under vacuum. The residue is chromatographed on silica using an AcOEt/MeOH mixture (90/10; v/v) as the eluent to give 0.63 g of the expected product after crystallization from an AcOEt/MeOH mixture. M.p.=236°–238° C.

Preparation 62

5-Chloro-3-(2-chlorophenyl)-1,3-dihydro-3-[2-(4-methylpiperazin-1-yl)acetamido]indol-2-one A) 5-Chloro-3-(2-chloroacetamido)-3-(2-chlorophenyl)-1,3-dihydroindol-2-one A mixture of 8 g of the compound obtained in Preparation 2 and 300 ml of benzene is heated to the reflux point, 3.4 g of chloroacetyl chloride are added and the reaction mixture is stirred for 2 hours under reflux. It is concentrated under vacuum and the residue is crystallized from a DCM/iso ether mixture to give 8 g of the expected product. M.p.=230° C.

B) 5-Chloro-3-(2-chlorophenyl)-1,3-dihydro-3-[2-(4-methylpiperazin-1-yl)acetamido]indol-2-one A mixture of 1.4 g of the compound obtained in the previous step, 0.455 g of 1-methylpiperazine, 0.523 g of potassium carbonate, 0.01 g of sodium iodide and 20 ml of DMF is heated at 60° C. for 1 hour. The reaction mixture is concentrated under vacuum, the residue is taken up with water and extracted with AcOEt, the organic phase is dried over sodium sulfate and the solvent is evaporated off under vacuum. The residue is chromatographed on silica using a DCM/MeOH mixture (96/4; v/v) as the eluent to give 1.2 g of the expected product after crystallization from a DCM/iso ether mixture. M.p.=214° C.

Preparation 63

5-Chloro-3-(2-chlorophenyl)-3-[3-(diethylamino) propionamido]-1,3-dihydroindol-2-one 0.43 ml of acryloyl chloride is added to a solution of 1.5 g of the compound obtained in Preparation 2 in 5 ml of pyridine and the mixture is stirred for 12 hours at RT. A further 0.43 ml of acryloyl chloride is added and stirring is continued for 12 hours. The reaction mixture is concentrated under vacuum, the residue is taken up with water and extracted with AcOEt, the organic phase is washed with a 1N solution of HCl and with water and dried over sodium sulfate and the solvent is evaporated off under vacuum. The residue is dissolved in 5 ml of EtOH, and 0.5 g of diethylamine is added in 4 days at RT. The mixture is concentrated under vacuum, the residue is taken up with a 1N solution of HCl, the aqueous phase is washed with AcOEt, rendered alkaline to pH 10 by the addition of a 5% solution of potassium carbonate and extracted with AcOEt, the organic phase is washed with water and with a saturated solution of NaCl and dried over sodium sulfate and the solvent is evaporated off under vacuum. The residue is chromatographed on silica using a DCM/MeOH/NH$_4$OH mixture (80/15/5; v/v/v) as the eluent to give 0.335 g of the expected product.

NMR spectrum at 200 MHz in DMSO-d$_6$
0.85 ppm: t: 6H
2.0 to 2.8 ppm: m: 8H
6.7 to 7.7 ppm: m: 7H
9.3 ppm: s: 1H
10.9 ppm: s: 1H Preparation 64

5-Chloro-3-(2-chlorophenyl)-3-[3-(diethylamino) propionamido]-1,3-dihydroindol-2-one, (+) isomer A solution of 1.88 g of the compound obtained in Preparation 28, (+) isomer, in 8 ml of pyridine is cooled to 0° C., 1.225 g of acryloyl chloride are added dropwise and the mixture is stirred for 72 hours at RT. Water is added to the reaction mixture, extraction is carried out with AcOEt, the organic phase is washed with water and with a saturated solution of NaCl and dried over sodium sulfate and the solvent is evaporated off under vacuum. The residue is dissolved in 5 ml of EtOH, 2.346 g of diethylamine are added and the mixture is stirred for two days at RT. It is concentrated under vacuum and the residue is chromatographed on silica using a DCM/MeOH mixture (75/25; v/v) as the eluent to give 0.350 g of the expected product after crystallization from a DCM/iso ether mixture. M.p.= 176°–178° C. $\alpha_D^{25}$=+56.3° (c=0.38; chloroform).

Preparation 65

3-(2-Chlorophenyl)-1,3-dihydro-5-methyl-3-(methylamino)indol-2-one

A) N-p-Methylphenyl-DL-2-chloromandelamide

A mixture of 32.1 g of p-toluidine, 55.95 g of DL-2-chloromandelic acid and 250 ml of 1,2-dichlorobenzene is refluxed for 6 hours, the water formed being removed by means of a Dean-Stark apparatus. The reaction mixture is cooled and the precipitate formed is filtered off and washed with iso ether to give 48 g of the expected product, which is used as such.

B) 3-(2-Chlorophenyl)-1,3-dihydro-5-methylindol-2-one

A mixture of 86 ml of concentrated sulfuric acid and 20 ml of fuming sulfuric acid (30% oleum) is cooled to 10° C. and 20 g of the compound obtained in the previous step are added in portions, the internal temperature being kept below 40 C. The reaction mixture is stirred for 18 hours at RT and poured onto ice and the precipitate formed is filtered off. The precipitate is dissolved in chloroform, the organic phase is washed with water to pH 7 and dried over sodium sulfate and the solvent is evaporated off under vacuum to give 12 g of the expected product after crystallization from a THF/DCM/iso ether mixture. M.p.=208° C.

C) 3-(2-Chlorophenyl)-1,3-dihydro-3-hydroxy-5-methylindol-2-one 0.952 g of sodium hydride as a 60% dispersion in oil is added at RT to a solution of 5.6 g of the compound obtained in the previous step in 150 ml of THF and the mixture is stirred for 30 minutes. 2.46 ml of dimethyl disulfide are then added and the mixture is stirred for 48 hours. Water is added to the reaction mixture and the precipitate formed is filtered off and washed with ether and then with pentane to give 5.1 g of the expected product. M.p.=295°–300° C.

D) 3-Chloro-3-(2-chlorophenyl)-1,3-dihydro-5-methylindol-2-one

A suspension of 1.5 g of the compound obtained in the previous step in 20 ml of DCM is cooled to +4° C., 0.84 ml of pyridine and then 0.6 ml of thionyl chloride are added and the mixture is stirred for 3 hours at RT. It is concentrated under vacuum and the residue is chromatographed on silica using a DCM/hexane mixture (80/20; v/v) and then DCM as the eluent to give 1.06 g of the expected product, which is used as such.

E) 3-(2-Chlorophenyl)-1,3-dihydro-5-methyl-3-(methylamino)indol-2-one 0.9 ml of an 8.03M solution of methylamine in EtOH is added at RT to a solution of 1.06 g of the compound obtained in the previous step in 5 ml of DCM and the mixture is stirred for 1 hour. It is concentrated under vacuum, the residue is extracted with AcOEt, washed with a saturated solution of NaCl and with water and dried over sodium sulfate and the solvent is evaporated off under vacuum. The residue is chromatographed on silica using DCM and then a DCM/AcOEt mixture (75/25; v/v) as the eluent to give 0.82 g of the expected product after crystallization from a DCM/iso ether mixture. M.p.=186°–187° C.

Preparation 66

3-Amino-3-(2-chlorophenyl)-1,3-dihydro-5-methoxyindol-2-one

A) N-p-Methoxyphenyl-DL-2-chloromandelamide A mixture of 33.25 g of p-anisidine, 50 g of DL-2-chloromandelic acid and 250 ml of 1,2-dichlorobenzene is heated at 225° C. for 5 hours, the water formed being removed by means of a Dean-Stark apparatus. The reaction mixture is concentrated to about 150 ml and left to crystallize overnight. The crystals formed are filtered off and washed with ether to give 43.76 g of the expected product.

B) 3-(2-Chlorophenyl)-1,3-dihydro-5-methoxyindol-2-one

A mixture of 393 g of polyphosphoric acid and 30 g of the compound obtained in the previous step is heated at 60° C. for 4 hours. 350 g of ice are added to the reaction mixture, extraction is carried out with AcOEt, the organic phase is washed with a saturated solution of NaCl to pH 7 and dried over magnesium sulfate and the solvent is evaporated off under vacuum until the product precipitates. After filtration and drying, 11.29 g of the expected product are obtained, which is used as such.

C) 3-Chloro-3-(2-chlorophenyl)-1,3-dihydro-5-methoxyindol-2-one 4.9 g of N-chlorosuccinimide are added to a suspension of 9.29 g of the compound obtained in the previous step in 100 ml of $CCl_4$ and the mixture is refluxed for 3 hours. After cooling, an insoluble material is filtered off and the filtrate is evaporated under vacuum. The residue is chromatographed on silica using DCM and then a DCM/AcOEt mixture (98/2; v/v to 96/4; v/v) as the eluent to give 6.1 g of the expected product, which is used as such.

D) 3-Azido-3-(2-chlorophenyl)-1,3-dihydro-5-methoxyindol-2-one 3.9 g of sodium azide are added to a solution of 6.1 g of the compound obtained in the previous step in 100 ml of acetonitrile and the mixture is refluxed for 4 hours. It is concentrated under vacuum, the residue is taken up with water and extracted with AcOEt, the organic phase is washed with a saturated solution of NaCl and with a 5% aqueous solution of sodium dithionite and dried over sodium sulfate and the solvent is evaporated off under vacuum. The residue is chromatographed on silica using DCM and then a DCM/AcOEt mixture (99/1; v/v) as the eluent to give 2.79 g of the expected product. Infrared spectrum in DCM: 2125 $cm^{-1}$.

E) 3-Amino-3-(2-chlorophenyl)-1,3-dihydro-5-methoxyindol-2-one 2.47 ml of triethylamine and then 1.78 ml of propane-1,3-dithiol are added by syringe, under an argon atmosphere, to a solution of 2.79 g of the compound obtained in the previous step in 44 ml of MeOH and the reaction mixture is heated at 60° C. for 4 hours. It is concentrated under vacuum and the residue is chromatographed on silica using DCM and then a DCM/AcOEt mixture (70/30; v/v) as the eluent to give 1.23 g of the expected product after crystallization from AcOEt.

NMR spectrum at 200 MHz in DMSO-$d_6$ 2.6 ppm: s: 2H 3.65 ppm: s: 3H 6.2 to 7.0 ppm: m: 3H 7.2 to 8.4 ppm: m: 4H 10.4 ppm: s: 1H

Preparation 67

3-(2-Chlorophenyl)-5-ethoxy-3-(ethylamino)-1,3-dihydroindol-2-one 5 ml of AcOH and then 0.2 ml of acetaldehyde are added at RT to a solution of 1 g of the compound obtained in Preparation 16 in 20 ml of MeOH, and 0.293 g of sodium cyanoborohydride is added in portions. The mixture is stirred for 30 minutes at RT, 5 drops of concentrated HCl are added and the reaction mixture is then neutralized by the addition of a 5% solution of potassium carbonate. The MeOH is evaporated off under vacuum, extraction is carried out with AcOEt, the organic phase is washed with water and with a saturated solution of NaCl and dried over sodium sulfate and the solvent is evaporated off under vacuum. The residue is chromatographed on alumina using DCM and then a DCM/AcOEt mixture (95/5; v/v) as the eluent to give 0.3 g of the expected product after crystallization from a DCM/iso ether mixture. M.p.=195°–200° C.

Preparation 68

3-(2-Chlorophenyl)-5-ethoxy-1,3-dihydro-3-(dimethylamino)indol-2-one 5 ml of AcOH and then 0.4 g of paraformaldehyde are added at RT to a solution of 1 g of the compound obtained in Preparation 16 in 20 ml of MeOH, and 0.532 g of sodium cyanoborohydride is added in portions in 1 hour. The mixture is stirred for 48 hours at RT, 5 drops of concentrated HCl are added and the reaction mixture is then neutralized by the addition of a 5% solution of potassium carbonate. The MeOH is evaporated off under vacuum, extraction is carried out with AcOEt, the organic phase is washed with water and with a saturated solution of NaCl and dried over sodium sulfate and the solvent is evaporated off under vacuum. The residue is chromatographed on silica using DCM and then a DCM/AcOEt mixture (90/10; v/v) as the eluent to give 1 g of the expected product after crystallization from a DCM/iso ether mixture (product in the form of a foam after drying at 90° C. under vacuum).

NMR spectrum at 200 MHz in DMSO-$d_6$
1.15 ppm: t: 3H
2.1 ppm: bs: 6H
3.75 ppm: qd: 2H
6.1 to 8.1 ppm: m: 7H
10.4 ppm: s: 1H Preparation 69

3-(2-Chlorophenyl)-5-fluoro-1,3-dihydro-3-(methylamino)indol-2-one

A) N-p-Fluorophenyl-DL-2-chloromandelamide

This compound is prepared according to the procedure described in step A of Preparation 2 from 4-fluoroaniline and DL-2-chloromandelic acid.

B) 3-(2-Chlorophenyl)-5-fluoro-1,3-dihydroindol-2-one 40 ml of fuming sulfuric acid (30% oleum) are added dropwise to 160 ml of concentrated sulfuric acid. 40 g of the compound obtained in the previous step are then added in portions, the internal temperature being kept below 40° C., and the reaction mixture is stirred for 16 hours at RT. It is poured onto 300 g of ice and extracted with AcOEt, the organic phase is washed with a saturated solution of NaCl and dried over sodium sulfate and the solvent is evaporated off under vacuum to give 42 g of the expected product, which is used as such.

C) 3-Bromo-3-(2-chlorophenyl)-5-fluoro-1,3-dihydroindol-2-one

A solution of 0.78 ml of bromine in 1 ml of chloroform is added dropwise to a suspension of 4.0 g of the compound obtained in the previous step in 100 ml of chloroform and the mixture is stirred for 30 minutes at RT. It is concentrated under vacuum, the residue is taken up with DCM and the solvent is evaporated off under vacuum to give 5.2 g of the expected product, which is used as such.

D) 3-(2-Chlorophenyl)-5-fluoro-1,3-dihydro-3-(methylamino)indol-2-one 2.8 ml of a 33% solution of methylamine in EtOH are added dropwise to a suspension of 5.2 g of the compound obtained in the previous step in 100 ml of DCM and the mixture is stirred for 2 hours at RT. It is concentrated under vacuum and extracted with AcOEt, the organic phase is washed with a 5% solution of sodium carbonate and with a saturated solution of NaCl and dried over sodium sulfate and the solvent is evaporated off under vacuum. The residue is chromatographed on silica using DCM and then a DCM/MeOH mixture (98/2; v/v) as the eluent to give 2.15 g of the expected product after crystallization from a DCM/iso ether mixture. M.p.=188°–189° C.

Preparations 70 and 71

5-Chloro-3-(2-chlorophenyl)-1,3-dihydro-4-methyl-3-(methylamino)indol-2-one (Preparation 70) and 5-chloro-3-(2-chlorophenyl)-1,3-dihydro-6-methyl-3-(methylamino)indol-2-one (Preparation 71)

A) 5-Chloro-3-(2-chlorophenyl)-1,3-dihydro-4-methylindol-2-one and 5-chloro-3-(2-chlorophenyl)-1,3-dihydro-6-methylindol-2-one A mixture of these two compounds is prepared according to the procedure described in step B of Preparation 2 from N-(4-chloro-3-methylphenyl)-DL-2-chloromandelamide, itself obtained according to the procedure described in step A of Preparation 2 from 4-chloro-3-methylaniline and DL-2-chloromandelic acid.

B) 3-Bromo-5-chloro-3-(2-chlorophenyl)-1,3-dihydro-4-methylindol-2-one and 3-bromo-5-chloro-3-(2-chlorophenyl)-1,3-dihydro-6-methylindol-2-one A solution of 0.6 ml of bromine in 60 ml of DCM is added dropwise at RT to a suspension of 3.62 g of the mixture of the two compounds obtained in the previous step in 60 ml of DCM and the mixture is stirred for 30 minutes at RT. It is concentrated under vacuum, the residue is taken up with DCM and the solvent is evaporated off under vacuum. The residue is chromatographed on silica using a DCM/AcOEt mixture (97/3; v/v) as the eluent to give 5.42 g of the mixture of the two expected products, which is used as such.

C) 5-Chloro-3-(2-chlorophenyl)-1,3-dihydro-4-methyl-3-(methylamino)indol-2-one (Preparation 70) and 5-chloro-3-(2-chlorophenyl)-1,3-dihydro-6-methyl-3-(methylamino)indol-2-one (Preparation 71)

2 ml of an 8.03M solution of methylamine in EtOH are added to a solution of 2.94 g of the mixture of the two compounds obtained in the previous step in 100 ml of EtOH and the mixture is stirred overnight at RT. It is concentrated under vacuum, the residue is taken up with 100 ml of a 5% solution of sodium carbonate and extracted four times with DCM, the organic phase is dried over sodium sulfate and the solvent is evaporated off under vacuum. The residue is chromatographed on silica using a DCM/AcOEt mixture (90/10; v/v) as the eluent to give the product of Preparation 70 after crystallization from a DCM/THF/iso ether mixture. Elution with a DCM/AcOEt mixture (75/25; v/v) then gives the product of Preparation 71 after crystallization from a DCM/THF/iso ether mixture.

the less polar compound: compound of Preparation 70.
NMR spectrum at 200 MHz in DMSO-$d_6$
1.8 ppm: s: 3H
2.1 ppm: d: 3H
3.1 ppm: qd: 1H
6.7 to 8.3 ppm: m: 6H
10.8 ppm: s: 1H
the more polar compound: compound of Preparation 71.
M.p.=234° C.

The compound of Preparation 71 can also be obtained by following the three steps of the method described below.

A') 5-Chloro-3-(2-chlorophenyl)-1,3-dihydro-6-methylindol-2-one

This compound is prepared according to the procedure described in step A above from 35 g of N-(4-chloro-3-methylphenyl)-DL-2-chloromandelamide. Crystallization of the mixture obtained in step A above from AcOEt, followed by recrystallization from a DCM/THF/AcOEt mixture, gives 8.1 g of the expected product. M.p.=203°–209° C.

B') 3-Bromo-5-chloro-3-(2-chlorophenyl)-1,3-dihydro-6-methylindol-2-one

This compound is prepared according to the procedure described in step B above from 8 g of the compound obtained in step A'. After concentration of the reaction mixture under vacuum, the residue is taken up with DCM and the precipitate formed is filtered off to give 6.0 g of the expected product. The filtrate is chromatographed on silica using a DCM/hexane mixture (30/70; v/v) as the eluent to give 1.42 g of the expected product in a second crop after crystallization from DCM. M.p.=109°–111° C.

C') 5-Chloro-3-(2-chlorophenyl)-1,3-dihydro-6-methyl-3-(methylamino)indol-2-one

This compound is prepared according to the procedure described in step C above from the compound obtained in step B'.

Preparation 72

3-[[2-(1-tert-Butoxycarbonylpiperid-4-yl)-ethyl]amino]-5,6-dichloro-3-(2-chlorophenyl)-1,3-dihydroindol-2-one A) N-3,4-Dichlorophenyl-DL-2-chloromandelamide This compound is prepared according to the procedure described in step A of Preparation 2 from 3,4-dichloroaniline and DL-2-chloromandelic acid. M.p.=160°–163° C.

B) 5,6-Dichloro-3-(2-chlorophenyl)-1,3-dihydroindol-2-one

A mixture of 53 ml of concentrated sulfuric acid and 12 ml of fuming sulfuric acid (30% oleum) is cooled to 0° C. and 13 g of the compound obtained in the previous step are added in portions. The reaction mixture is stirred for 24 hours at RT and poured into water and the precipitate formed is filtered off. The precipitate is dissolved in AcOEt, the organic phase is washed with water to pH 7 and dried over sodium sulfate and the solvent is partially evaporated off under vacuum. The crystalline product formed is filtered off and recrystallized from a THF/DCM/AcOEt mixture to give 1.3 g of the expected product. M.p.=198°–201° C.

C) 3-Bromo-5,6-dichloro-3-(2-chlorophenyl)-1,3-dihydroindol-2-one

A solution of 0.32 g of bromine in 1 ml of chloroform is added dropwise to a suspension of 1.95 g of the compound obtained in the previous step in 30 ml of chloroform and the mixture is stirred for 30 minutes at RT. It is concentrated under vacuum, the residue is taken up with DCM and the solvent is evaporated off under vacuum. The residue is extracted with AcOEt, the organic phase is washed with water to pH 7 and dried over sodium sulfate and the solvent is evaporated off under vacuum to give the expected product after crystallization from DCM. M.p.=215°–218° C.

D) 4-(2-Aminoethyl)-1-(tert-butoxycarbonyl)piperidine a) 1-(tert-Butoxycarbonyl)-4-(2-hydroxyethyl)piperidine A solution of 87 g of di-tert-butyl dicarbonate in 100 ml of tert-butanol is added dropwise at RT to a solution of 51 g of 4-(2-hydroxyethyl)piperidine in 20 ml of tert-butanol and the mixture is stirred overnight at RT. It is concentrated under vacuum, the residue is extracted with AcOEt, the organic phase is washed with a buffer solution of pH 2 and dried over sodium sulfate and the solvent is evaporated off under vacuum to give 91.5 g of the expected product, which is used as such.

b) 2-(1-tert-Butoxycarbonylpiperid-4-yl)ethyl methanesulfonate

A solution of 86.8 g of the compound obtained in the previous step in 400 ml of DCM is cooled to 0° C., a solution of 53 ml of triethylamine in 20 ml of DCM and then a solution of 33 ml of methanesulfonyl chloride in 20 ml of DCM are added and the reaction mixture is stirred for 5 hours. It is washed with water and, after decantation, the organic phase is dried over sodium sulfate and the solvent is evaporated off under vacuum to give the expected product, which is used as such.

c) 2-(1-tert-Butoxycarbonylpiperid-4-yl)ethyl azide

A mixture of 5 g of the compound obtained in the previous step, 1.2 g of sodium azide and 15 ml of DMSO is heated at 50° C. for 4 hours. The reaction mixture is poured into water, extracted with AcOEt and dried over sodium sulfate and the solvent is evaporated off under vacuum. The residue is chromatographed on silica using a hexane/AcOEt mixture (90/10; v/v) as the eluent to give 2.8 g of the expected product, which is used as such in the next step.

d) 4-(2-Aminoethyl)-1-(tert-butoxycarbonyl)piperidine

A mixture of 2.8 g of the compound obtained in the previous step, 0.5 g of Raney® nickel, 0.54 ml of hydrazine monohydrate and 20 ml of EtOH is stirred for 4 hours at RT. A further 0.54 ml of hydrazine monohydrate is added in 4 hours and the mixture is stirred for 48 hours at RT. The catalyst is filtered off and the filtrate is concentrated under vacuum to give 2.3 g of the expected product, which is used as such.

E) 3-[[2-(1-tert-Butoxycarbonylpiperid-4-yl)ethyl]amino]-5,6-dichloro-3-(2-chlorophenyl)-1,3-dihydroindol-2-one A solution of 1.05 g of 4-(2-aminoethyl)-1-(tert-butoxycarbonyl)piperidine and 0.46 g of triethylamine in 10 ml of chloroform is added at RT to a solution of 1.8 g of the compound obtained in step C in 50 ml of THF and the mixture is stirred for 2 hours at RT. It is concentrated under vacuum, the residue is taken up with a 5% solution of potassium carbonate and extracted with AcOEt, the organic phase is washed with water and with a saturated solution of NaCl, boiling THF is added to the organic phase, the latter is dried over sodium sulfate and the solvents are partially evaporated off. The crystalline product formed is filtered off to give 1.94 g of the expected product. M.p.=248°–249° C.

Preparation 73

5-Chloro-3-(2-chlorophenyl)-7-fluoro-1,3-dihydro-3-(methylamino)indol-2-one

A) N-(4-Chloro-2-fluorophenyl)-DL-2-chloromandelamide

This compound is prepared according to the procedure described in step A of Preparation 2 from 4-chloro-2-fluoroaniline and DL-2-chloromandelic acid.

B) 5-Chloro-3-(2-chlorophenyl)-7-fluoro-1,3-dihydro-indol-2-one 30 ml of concentrated sulfuric acid are cooled to +4° C., 7.5 ml of fuming sulfuric acid (30% oleum) are added and 7 g of the compound obtained in the previous step are then added in portions. The mixture is stirred for 48 hours at RT and 300 ml of water are added to the reaction mixture. Extraction is carried out with AcOEt, the organic phase is washed with a saturated solution of NaCl and with water and dried over sodium sulfate and the solvent is evaporated off under vacuum to give 3.4 g of the expected product after crystallization from AcOEt.

C) 3-Bromo-5-chloro-3-(2-chlorophenyl)-7-fluoro-1,3-dihydroindol-2-one 0.53 ml of bromine is added to a suspension of 3.4 g of the compound obtained in the previous step in 20 ml of chloroform and the mixture is stirred for 3 hours at RT. It is concentrated under vacuum, the residue is taken up with DCM and the solvent is evaporated off under vacuum to give 4.2 g of the expected product, which is used as such.

D) 5-Chloro-3-(2-chlorophenyl)-7-fluoro-1,3-dihydro-3-(methylamino)indol-2-one 2.7 ml of an 8.03M solution of methylamine in EtOH, diluted in 5 ml of DCM, are added dropwise at RT to a solution of 4.2 g of the compound obtained in the previous step in 25 ml of DCM and the reaction mixture is stirred for 3 hours at RT. It is concentrated under vacuum, the residue is taken up with a 5% solution of sodium carbonate and extracted with AcOEt, the organic phase is washed with a saturated solution of NaCl and with water and dried over sodium sulfate and the solvent is evaporated off under vacuum. The residue is chromatographed on silica using a DCM/AcOEt mixture (85/15; v/v) as the eluent to give 1.1 g of the expected product after crystallization from a DCM/THF/AcOEt mixture. M.p.=219° C.

Preparation 74

5-Chloro-3-(2-chlorophenyl)-3-[[2-(diethylamino)-2-methylpropyl]amino]-1,3-dihydroindol-2-one A) 2-(Diethylamino)-2-methylpropylamine This compound is prepared according to the procedure described in patent application EP 0429344.

B) 5-Chloro-3-(2-chlorophenyl)-3-[[2-(diethylamino)-2-methylpropyl]amino]-1,3-dihydroindol-2-one A solution of 2.42 g of the compound obtained in the previous step and 1.41 g of triethylamine in 30 ml of chloroform is cooled to 0° C., 5 g of the compound obtained in step C of Preparation 2 are added in portions and the reaction mixture is stirred for 18 hours at RT. It is washed with water and, after decantation, the organic phase is dried over sodium sulfate and the solvent is evaporated off under vacuum. The residue is chromatographed on silica using AcOEt as the eluent to give 2.4 g of the expected product after crystallization from ether. M.p.=174° C.

Preparation 75

3-[2-[N-(tert-Butoxycarbonylmethyl)-N-methylamino]acetamido]-5-chloro-3-(2-chlorophenyl)-1,3-dihydroindol-2-one A mixture of 1.5 g of the compound obtained in step A of Preparation 62, 0.957 g of tert-butyl sarcosinate hydrochloride, 1.2 g of DIPEA, 0.01 g of sodium iodide and 20 ml of acetone is refluxed for 18 hours. It is concentrated under vacuum, the residue is extracted with AcOEt, the organic phase is washed with water and dried over sodium sulfate and the solvent is evaporated off under vacuum. The residue is chromatographed on silica using a DCM/AcOEt mixture (70/30; v/v) as the eluent to give 1.7 g of the expected product after crystallization from a DCM/iso ether mixture. M.p.=200° C.

Preparation 76

5-Chloro-3-(2-chlorophenyl)-1,3-dihydro-3-(dimethylamino)indol-2-one, (+) isomer 0.6 g of paraformaldehyde and 0.6 g of sodium cyanoborohydride are added in portions in 48 hours to a solution of 1.5 g of the compound obtained in Preparation 28, (+) isomer, in 30 ml of MeOH and 20 ml of AcOH. 5 drops of concentrated HCl are added, the mixture is then rendered alkaline to pH 10 by the addition of a 5% solution of potassium carbonate, the MeOH is evaporated off under vacuum, the aqueous phase is extracted with AcOEt, the organic phase is washed with water and with a saturated solution of NaCl and dried over sodium sulfate and the solvent is evaporated off under vacuum. The residue is chromatographed on alumina using a DCM/MeOH mixture (60/40; v/v) as the eluent to give 0.62 g of the expected product after crystallization from a DCM/hexane mixture. M.p.=169°–172° C. $\alpha_D^{25}$=+325° (c=0.26; chloroform).

NMR spectrum at 200 MHz in DMSO-$d_6$ 2.2 ppm: bs: 6H 6.7 to 8.2 pp: m: 7H 10.85 ppm: s: 1H Preparation 77

3-[[2-(1-tert-Butoxycarbonylpiperid-4-yl)-ethyl]amino]-5-chloro-3-(2-chlorophenyl)-1,3-dihydro-6-methylindol-2-one A solution of 1.35 g of 4-(2-aminoethyl)-1-(tert-butoxycarbonyl)piperidine and 1.75 g of triethylamine in 20 ml of THF is added dropwise at RT to a solution of 2.1 g of 3-bromo-5-chloro-3-(2-chlorophenyl)-1,3-dihydro-6-methylindol-2-one, obtained in step B' of Preparation 71, in 20 ml of THF and the reaction mixture is stirred for 1 hour at RT. It is concentrated under vacuum, the residue is taken up with 400 ml of AcOEt and 50 ml of THF, the resulting suspension is washed twice with a 5% solution of sodium carbonate, with water and with a saturated solution of NaCl and, after decantation, the solid in suspension is filtered off. The solid is dissolved in 400 ml of boiling THF and dried over sodium sulfate and the solvent is partially evaporated off under vacuum. The crystalline product formed is filtered off to give 1.65 g of the expected product. M.p.=245°–248° C.

Preparation 78

3-[[5-(Benzyloxycarbonyl)pentyl]amino]-5-chloro-3-(2-chlorophenyl)-1,3-dihydroindol-2-one A) Benzyl 6-(tert-butoxycarbonylamino)hexanoate 1.94 ml of DBU and then 1.54 ml of benzyl bromide are added at RT to a solution of 3 g of 6-(tert-butoxycarbonylamino)hexanoic acid in 60 ml of DCM and the mixture is stirred for 24 hours at RT. It is concentrated under vacuum, the residue is taken up with 100 ml of water and extracted with AcOEt, the organic phase is washed with a 5% solution of potassium carbonate, with a saturated solution of NaCl and with water and dried over sodium sulfate and the solvent is evaporated off under vacuum to give 2.8 g of the expected product, which is used as such.

B) 3-[[5-(Benzyloxycarbonyl)pentyl]amino]-5-chloro-3-(2-chlorophenyl)-1,3-dihydroindol-2-one A solution of 4 g of the compound obtained in the previous step in 20 ml of DCM is cooled to +4° C., 40 ml of TFA are added and the mixture is stirred for 1 hour at +4° C. It is concentrated under vacuum, the residue is taken up three times with 50 ml of DCM and the solvent is evaporated off under vacuum. The oil obtained is taken up with 30 ml of chloroform, 4.5 g of the compound obtained in step C of Preparation 2 are added, a solution of 5.24 ml of triethylamine in 5 ml of chloroform is then added dropwise and the mixture is stirred for 1 hour at RT. It is concentrated under vacuum, the residue is extracted with AcOEt, the organic phase is washed with a saturated solution of NaCl and with water and dried over sodium sulfate and the solvent is evaporated off under vacuum. The residue is chromatographed on silica using DCM and then a DCM/AcOEt mixture (90/10; v/v) as the eluent to give 3.8 g of the expected product after crystallization from a DCM/hexane mixture. M.p.=98°–99° C.

The 1,3-dihydroindol-2-ones collected in TABLE I below are prepared by following the procedures described in the Preparations above.

TABLE I

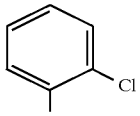

| Preparation | R'$_1$ | R'$_2$ | R$_3$ | R'$_4$ | Solvate M.p. °C. or NMR cristallization solvent |
|---|---|---|---|---|---|
| 79 (a) | 5-Cl | H |  | —NH—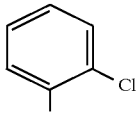 | 200 DCM/iso ether |
| 80 (b) | 5-Cl | H | 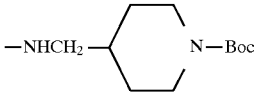 | —NHCH$_2$—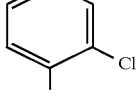N—Boc | 238 DCM/iso ether |
| 81 (a) | 5-Cl | H | 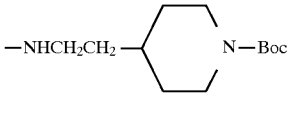 | —NHCH$_2$CH$_2$—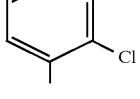N—Boc | 218 DCM/iso ether |
| 82 (c) | 5-Cl | H | 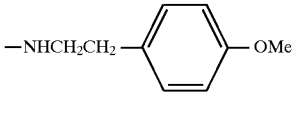 | —NHCH$_2$CH$_2$—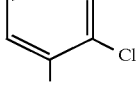—OMe | 165–168 DCM/iso ether |
| 83 (c) | 5-Cl | H | 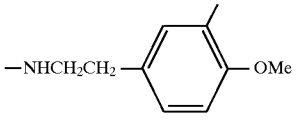 | —NHCH$_2$CH$_2$—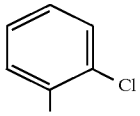 OMe, OMe | 189–193 DCM/iso ether |
| 84 (c) | 5-Cl | H | 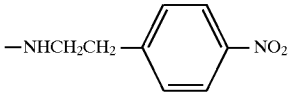 | —NHCH$_2$CH$_2$—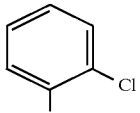—NO$_2$ | 0.33 H$_2$O 195–198 DCM/iso ether |
| 85 (a) | 5-Cl | H | 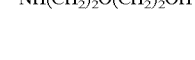 | —NH(CH$_2$)$_2$O(CH$_2$)$_2$OH | 0.5 H$_2$O 173–174 DCM/iso ether |

TABLE I-continued

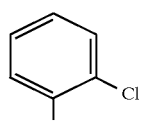

| Preparation | R'₁ | R'₂ | R₃ | R'₄ | Solvate M.p. °C. or NMR cristallization solvent |
|---|---|---|---|---|---|
| 86 (d) | 5-Cl | H | 2-Cl-phenyl | —NH(CH₂)₂O(CH₂)₂OSi(Me)₃ | 140–142 DCM/iso ether |
| 87 (a) | 5-Cl | H | 2-Cl-phenyl | —NH(CH₂)₃OMe | 192 |
| 88 (a) | 5-Cl | H | 2-Cl-phenyl | —NHCH₂CH₂N(Me)₂ | 159 DCM/iso ether |
| 89 (c) | 5-Cl | H | 2-Cl-phenyl | —NHCH₂CH₂N(nBu)₂ | 110 pentane |
| 90 (a) | 5-Cl | H | 2-Cl-phenyl | —NH(CH₂)₃N(Et)₂ | 148 DCM/iso ether |
| 91 (b) | 5-Cl | H | 2-Cl-phenyl | —NH(CH₂)₂—N(pyrrolidine) | 190 iso ether |
| 92 (f) | 5-Cl | H | 2-Cl-phenyl | —NHCH₂CON(Me)(CH₂)₂N(Me)₂ | 185 iso ether/hexane |
| 93 (g) | 5-Cl | H | 2-Cl-phenyl | —NH(CH₂)₃COOBz | used as such |
| 94 (o) | 5-Cl | H | 2-Cl-phenyl | —NH(CH₂)₄COOBz | 116–117 DCM/iso ether |
| 95 (a) | 5-Cl | H | 2-Cl-phenyl | —NH(CH₂)₅CN | 160–162 DCM/iso ether |

TABLE I-continued

[Structure: substituted indolin-2-one with R'₁, R'₂ on benzene ring and R₃, R'₄ at 3-position]

| Preparation | R'₁ | R'₂ | R₃ | R'₄ | Solvate M.p. °C. or NMR cristallization solvent |
|---|---|---|---|---|---|
| 96 (b) | 5-Cl | H | 2-Cl-phenyl | —N(piperidin-4-yl)NMe₂ (with Me on ring N) | 251 DCM/iso ether |
| 97 (h) | 5-Cl | H | 2-Cl-phenyl | —NHCOCH₂N(Et)₂ | 194–195 DCM/iso ether |
| 98 (i) | 5-Cl | H | 2-Cl-phenyl | —NHCOCH(Me)N(CH₂)₂N(Me)₂ | 120 DCM/iso ether |
| 99 (j) | 5-Et | H | 2-Cl-phenyl | —NH—Me | 139–140 DCM/iso ether |
| 100 (k) | 5-Cl | 6-Cl | 2-Cl-phenyl | —NH(CH₂)₃—OMe | 163–164 DCM/iso ether |
| 101 (l) | 5-Cl | 6-Cl | 2-Cl-phenyl | —NH(CH₂)₂O(CH₂)₂N(Me)₂ | NMR oil |
| 102 (m) | 5-Cl | 6-Cl | 2-Cl-phenyl | —NH(CH₂)₂N(Et)₂ | 130 DCM/iso ether |
| 103 (n) | 5-Cl | 6-Cl | 2-Cl-phenyl | —NH(CH₂)₅NH—Boc | 205–210 DCM/THF/ iso ether |
| 104 (p) | 5-Cl | 4-Cl | 2-Cl-phenyl | —NHCH₂-(N-Boc-piperidin-4-yl) | 238 |
| 105 (q) | 5-Cl | 6-Cl | 2-Cl-phenyl | —NHCH₂-(N-Boc-piperidin-4-yl) | 173 |

TABLE I-continued

| Preparation | R'₁ | R'₂ | R₃ | R'₄ | Solvate M.p. °C. or NMR cristallization solvent |
|---|---|---|---|---|---|
| 106 (r) | 5-Cl | 6-Me | 2-Cl-phenyl | $-NHCH_2-$[4-piperidinyl]$-N-Boc$ | 184 DCM/iso ether |
| 107 (s) | 5-Cl | H | 2-Cl-phenyl | $-NHCH_2-C(Me)_2-CH_2NH-Boc$ | 195 iso ether |
| 108 (b) | 5-Cl | H | 2-Cl-phenyl | $-NH(CH_2)_2-S-Et$ | 128 DCM/iso ether |
| 109 (c) | 5-Cl | H | 2-Cl-phenyl | $-NHCH_2CH_2-$(3,4-methylenedioxyphenyl) | 168–170 DCM/iso ether |
| 110 (t) | 5-Cl | H | 2-Cl-phenyl | $-NH-C(CH_2OH)(H)-(CH_2)_4-NH-Z$ | 96–98 DCM/iso ether |
| 111 (u) | 5-Cl | H | 2-Cl-phenyl | $-NH-C(CH_2OSi(Me)_3)(H)-(CH_2)_4-NH-Z$ | — |
| 112 (v) | 5-CF₃ | H | 2-Cl-phenyl | $-NH-Me$ | 153–155 DCM/iso ether |
| 113 (w) | 5-OEt | H | 2-Cl-phenyl | $-N(Et)_2$ | 170–172 DCM/iso ether |
| 114 (x) | 5-Cl | 4-Me | 2-Cl-phenyl | $-NHCOCH_2CH_2N(Et)_2$ | — |
| 115 (y) | 5-Cl | 6-Me | 2-Cl-phenyl | $-NHCOCH_2CH_2N(Et)_2$ | 200–203 EtOH |

(a) This compound is prepared according to the procedure described in Preparation 30 by using the appropriate amines.

(b) This compound is prepared according to the procedure described in Preparation 31 by using the appropriate amines in the presence of DIPEA.

(c) This compound is prepared according to the procedure described in Preparation 32 by using the appropriate amines.

(d) This compound is prepared according to the procedure described in Preparation 35 from the compound obtained in Preparation 85.

(e) This compound is prepared according to the procedure described in Preparation 39 by using the appropriate amines.

(f) This compound is prepared according to the procedure described in step C of Preparation 50 from the compound obtained in step B of Preparation 50 and the appropriate amines.

(g) This compound is prepared according to the procedure described in Preparation 52.

(h) This compound is prepared according to the procedure described in Preparation 61 from the compound obtained in Preparation 2, bromoacetyl bromide and diethylamine.

(i) This compound is prepared according to the procedure described in step B of Preparation 62 by using the appropriate amine.

(j) This compound is prepared according to the procedures described in steps A, B, C, D and then E of Preparation 65.

(k) This compound is prepared according to the procedure described in step E of Preparation 72 from the compound obtained in step C of Preparation 72 and (3-methoxypropyl) amine in the presence of triethylamine.

(l) This compound is prepared according to the procedure described in step E of Preparation 36 from the compound obtained in step C of Preparation 72.

(m) This compound is prepared according to the procedure described in Preparation 38 from the compound obtained in step C of Preparation 72.

(n) This compound is prepared according to the procedure described in step D of Preparation 43 from the compound obtained in step C of Preparation 72.

(o) This compound is prepared according to the procedure described in step B of Preparation 78.

(p) This compound is prepared according to the procedure described in Preparation 80 from 3-bromo-4,5-dichloro-3-(2-chlorophenyl)-1,3-dihydroindol-2-one (m.p. =230° C.), itself obtained according to the procedure described in step C of Preparation 72 from 4,5-dichloro-3-(2-chlorophenyl)-1,3-dihydroindol-2-one, obtained as a by-product in step B of Preparation 72.

(q) This compound is prepared according to the procedure described in Preparation 80 from the compound obtained in step C of Preparation 72.

(r) This compound is prepared according to the procedure described in Preparation 80 from the compound obtained in step B' of Preparation 71.

(s) This compound is prepared according to the procedure described in Preparation 49 from the compound obtained in step C of Preparation 2 and 1,3-diamino-2,2-dimethylpropane.

(t) the more polar isomer; this compound is prepared according to the procedure described in step B of Preparation 59 from the compound obtained in step C of Preparation 2 and N-ε-(benzyloxycarbonyl)-D-lysinol.

$\alpha_D^{25}$=+99.2° C. (c=0.275; chloroform).

(u) This compound is prepared according to the procedure described in Preparation 60 from the compound obtained in Preparation 110 and is used as such in EXAMPLE 269.

(v) This compound is prepared according to the procedures described in steps A, B, C and then D of Preparation 69.

(w) This compound is prepared according to the procedure described in Preparation 68 from the compound obtained in Preparation 16 and acetaldehyde.

(x) This compound is prepared according to the procedure described in Preparation 63 from 3-amino-5-chloro-3-(2-chlorophenyl)-1,3-dihydro-4-methylindol-2-one itself obtained according to the procedure described in step C of Preparation 70, by using ammonia gas.

(y) this compound is prepared according to the procedure described in Preparation 63 from 3-amino-5-chloro-3-(2-chlorophenyl)-1,3-dihydro-6-methylindol-2-one, itself obtained according to the procedure described in step C of Preparation 70, by using ammonia gas.

NMR spectrum at 200 MHz in DMSO-$d_6$ of the compound of Preparation 101

2.1 ppm:s:6H
2.35 ppm:t:2H
2.5 ppm:mt:2H
3.0 ppm:t:1H
3.4 ppm:t:4H
6.8 to 8.2 ppm:m:6H
10.95 ppm:s:1H Preparations of compounds of formula (III) or (IV)

Preparation 116

4-(N',N'-Diethylureido)benzenesulfonyl chloride

A) N',N'-Diethyl-N-phenylurea

A solution of 10 g of aniline in 50 ml of pyridine is cooled to 0° C. and a solution of 14.56 g of diethylcarbamoyl chloride in 10 ml of pyridine is added slowly. The mixture is stirred for 6 hours, the temperature being allowed to rise to RT, and is then poured into water. It is extracted with AcOEt, washed with water and with a 5% solution of potassium hydrogensulfate, dried over sodium sulfate and evaporated under vacuum. The residue is chromatographed on silica using DCM and then a DCM/AcOEt mixture (90/10; v/v) as the eluent to give 13 g of the expected product, which is used as such in the next step.

B) 4-(N',N'-Diethylureido)benzenesulfonyl chloride 3.5 ml of chlorosulfonic acid are cooled to +5° C. and 2 g of the compound obtained in the previous step are added in 15 minutes. The reaction mixture is heated at 60° C. for 2 hours, with vigorous stirring, and then cooled to RT. Ice and then water are added slowly and the mixture is extracted with AcOEt, washed with water to pH 7, dried over sodium sulfate and evaporated under vacuum to give the expected product after recrystallization from benzene. m=1.54 g. M.p.=148°–150° C.

Preparation 117 tert-Butyl 4-bromomethylbenzoate

A) tert-Butyl 4-methylbenzoate 37 g of tert-butanol and then 26 ml of pyridine are added to 39.04 g of p-toluoyl chloride and the reaction mixture is refluxed for 3 hours. After cooling, it is poured into water, extracted with AcOEt, washed with a 1N solution of HCl and then with a 5% solution of sodium hydrogencarbonate, dried over sodium sulfate and evaporated under vacuum. The residue is chromatographed on silica using hexane and then a hexane/DCM mixture (80/20; v/v) as the eluent to give 38.9 g of the expected product, which is used as such in the next step.

B) tert-Butyl 4-bromomethylbenzoate

A mixture of 10.4 g of the compound obtained in the previous step, 9.64 g of N-bromosuccinimide, 0.10 g of dibenzoyl peroxide and 250 ml of $CCl_4$ is refluxed for 40 minutes. After cooling, the insoluble material is filtered off and the filtrate is taken up with $CCl_4$, washed with a 5% solution of sodium hydrogencarbonate, dried over sodium sulfate and evaporated under vacuum to give 13 g of a clear oil, which is subsequently used as such.

Preparation 118

1-Acetylindoline-5-sulfonyl chloride

A) 1-Acetylindoline

A solution of 11.9 g of indoline in 100 ml of chloroform is cooled to 0° C. 13.9 ml of triethylamine are added and a solution of 10.4 ml of acetic anhydride in 10 ml of chloroform is then added dropwise, followed by 0.1 g of 4-dimethylaminopyridine. After stirring for two hours at RT, water is added to the reaction mixture, extraction is carried out with chloroform, the organic phase is dried over sodium sulfate and the solvent is evaporated off under vacuum to give 15.44 g of the expected product, which is used as such.

B) 1-Acetylindoline-5-sulfonyl chloride 32 ml of chlorosulfonic acid are cooled to +5° C. and 15.4 g of the compound obtained in the previous step are added rapidly in portions. The reaction mixture is heated at 60° C. for 2 hours and then cooled to RT. Ice is added slowly and the precipitate formed is filtered off to give 18.07 g of the expected product after crystallization from a DCM/iso ether mixture.

NMR spectrum at 200 MHz in DMSO-$d_6$
2.15 ppm:s:3H
3.1 ppm:t:2H
4.1 ppm:t:2H
7.3 to 8.1 ppm:m:3H Preparation 119

1-(Methoxycarbonyl)indoline-5-sulfonyl chloride

A) 1-Methoxycarbonylindoline

A solution of 10 g of indoline in 10 ml of pyridine is cooled to 0° C. a solution of 7.9 g of methyl chloroformate in 10 ml of DCM is added dropwise and the mixture is stirred for 1 hour at 0C. A further solution of 7.9 g of methyl chloroformate in 10 ml of DCM is then added and the reaction mixture is concentrated under vacuum. The residue is taken up with water and extracted with AcOEt, the organic phase is washed with a 5% solution of potassium hydrogensulfate, with water and with a saturated solution of NaCl and dried over sodium sulfate and the solvent is evaporated off under vacuum to give 8.3 g of the expected product after trituration in a DCM/iso ether mixture and then filtration. M.p.=69°–70° C.

B) 1-(Methoxycarbonyl)indoline-5-sulfonyl chloride

A mixture of 3 g of the compound obtained in the previous step and 7 ml of chlorosulfonic acid is stirred for 90 minutes at RT. Ice and then water are successively added to the reaction mixture, extraction is carried out with AcOEt, the organic phase is washed with water to pH 7 and dried over sodium sulfate and the solvent is evaporated off under vacuum to give 2.8 g of the expected product after crystallization from a DCM/iso ether mixture. M.p.=113°–114° C.

Preparation 120

1-(Diethylaminocarbonyl)indoline-5-sulfonyl chloride

A) 1-(Diethylaminocarbonyl)indoline

A solution of 6 g of indoline in 10 ml of pyridine is cooled to 0° C. 6.4 ml of diethylcarbamoyl chloride are added dropwise and the mixture is stirred for 18 hours at RT. Water is added to the reaction mixture, extraction is carried out with AcOEt, the organic phase is washed with water and with a 5% solution of potassium hydrogensulfate and dried over sodium sulfate and the solvent is evaporated off under vacuum. The residue is chromatographed on silica using DCM as the eluent to give 8 g of the expected product, which is used as such.

B) 1-(Diethylaminocarbonyl)indoline-5-sulfonyl chloride 12.3 ml of chlorosulfonic acid are cooled to +5° C. and 8 g of the compound obtained in the previous step are added rapidly. The reaction mixture is heated at 60° C. for 2 hours, with vigorous stirring, and then cooled to RT. Ice and then water are added slowly, extraction is carried out with AcOEt, the organic phase is washed with water to pH 7 and dried over sodium sulfate and the solvent is evaporated off under vacuum. The residue is chromatographed on silica using a DCM/ AcOEt mixture (95/5; v/v) as the eluent to give 4.54 g of the expected product.

NMR spectrum at 200 MHz in DMSO-$d_6$
1.15 ppm:t:6H
2.95 ppm:t:2H
3.2 ppm:qd:4H
3.75 ppm:t:2H
6.7 to 7.5 ppm:m:3H

EXAMPLE 1

3-Amino-5-chloro-1,3-dihydro-1-(2,4-dimethoxybenzenesulfonyl)-3-phenylindol-2-one A solution of 0.3 g of 3-amino-5-chloro-1,3-dihydro-3-phenylindol-2-one in 7 ml of DMF is cooled to 0C under an argon atmosphere and 0.037 g of sodium hydride as an 80% dispersion in oil is added. After stirring for 20 minutes, 0.275 g of 2,4-dimethoxybenzenefulfonyl chloride is added and the reaction mixture is stirred overnight, the temperature being allowed to rise to RT. It is poured into water, extracted with AcOEt, washed with water and with a saturated solution of NaCl, dried over sodium sulfate and evaporated under vacuum. The residue is chromatographed on silica using a DCM/AcOEt mixture (95/5; v/v) as the eluent to give the expected product after crystallization from a DCM/ iso ether/hexane mixture. m=0.31 g. M.p.=108-110° C.

EXAMPLE 2

3-Acetamido-5-chloro-1,3-dihydro-1-(2,4-di-methoxybenzenesulfonyl)-3-phenylindol-2-one 0.051 g of triethylamine and then 0.04 g of acetyl chloride are added to a solution of 0.234 g of the compound obtained in EXAMPLE 1 in 2 ml of DCM and the reaction mixture is stirred for two hours at RT. It is poured into water, extracted with DCM, washed with water, dried over sodium sulfate and evaporated under vacuum to give the expected product after crystallization and recrystallization from a DCM/iso ether/ MeOH mixture. m=0.146 g. M.p.=253° C.

EXAMPLE 3

3-Amino-5-chloro-3-(2-chlorophenyl)-1,3-dihydro-1-(2,4-dimethoxybenzenesulfonyl)indol-2-one This compound is prepared according to the procedure described in EXAMPLE 1 from 0.315 g of 3-amino-5-chloro-3-(2-chlorophenyl)-1,3-dihydroindol-2-one 0.256 g of 2,4-dimethoxybenzenesulfonyl chloride. This gives the expected product after crystallization from a DCM/iso ether mixture. m=0.300 g. M.p.= 179-180° C.

EXAMPLE 4

5-Chloro-3-(ethanecarboxamido)-3-(2-chlorophenyl)-1,3-dihydro-1-(2,4-dimethoxybenzenesulfonyl)indol-2-one 0.08 g of propionyl chloride is added to a solution of 0.33 g of the compound obtained in EXAMPLE 3 in 3 ml of pyridine and the reaction mixture is stirred for 1 hour at RT. It is poured into water, extracted with AcOEt, dried over sodium sulfate and evaporated under vacuum. The residue is chromatographed on silica using a DCM/AcOEt mixture (98/2; v/v) as the eluent to give the expected product after crystallization from a DCM/iso ether mixture. m=0.18 g. M.p.=188° C.

EXAMPLE 5

5-Chloro-3-(2-chlorophenyl)-1,3-dihydro-1-(2,4-dimethoxybenzenesulfonyl)-3-(methoxycarboxamido)indol-2-one 0.066 g of pyridine and then 0.095 g of methyl chloroformate are added at RT to a solution of 0.205 g of the compound obtained in EXAMPLE 3 in 2 ml of DCM. The reaction mixture is stirred for 72 hours at between 0° and +4° C. and poured into water. It is extracted with DCM, washed with a 5% solution of potassium hydrogensulfate and with water, dried over sodium sulfate and evaporated under vacuum to give the expected product after crystallization from a DCM/iso ether mixture. m=0.175 g. M.p.=225°–228° C.

EXAMPLE 6

5-Chloro-3-(2-chlorophenyl)-1,3-dihydro-1-(2,4-dimethoxybenzenesulfonyl)-3-(methylsulfonamido)indol-2-one A solution of 0.4 g of the compound obtained in EXAMPLE 3 in 5 ml of pyridine is cooled to 0° C. and 0.1 g of methanesulfonyl chloride is added. The mixture is stirred for 18 hours, the temperature being allowed to rise to RT, and evaporated under vacuum. The residue is extracted with AcOEt, washed with a 5% solution of potassium hydrogensulfate, dried over sodium sulfate and evaporated under vacuum. The residue due is chromatographed on silica using a DCM/AcOEt mixture (98/2; v/v) as the eluent to give the expected product after crystallization from a DCM/iso ether mixture. m=0.22 g. M.p.=252° C.

EXAMPLE 7

5-Chloro-3-(2-chlorophenyl)-1,3-dihydro-1-(2,4-dimethoxybenzenesulfonyl)-3-(phenoxycarboxamido)indol-2-one 0.250 g of phenyl chloroformate is added at RT to a solution of 0.530 g of the compound obtained in EXAMPLE 3 in 4 ml of pyridine. The mixture is stirred for 18 hours at RT and evaporated under vacuum. The residue is extracted with DCM, washed with a 5% solution of potassium hydrogensulfate and with water, dried over sodium sulfate and evaporated under vacuum. The residue is chromatographed on silica using a DCM/AcOEt mixture (98/2; v/v) as the eluent to give the expected product after crystallization from a DCM/iso ether mixture. m=0.47 g. M.p.=95°–100° C.

EXAMPLE 8

5-Chloro-3-(2-chlorophenyl)-1,3-dihydro-1-(2,4-dimethoxybenzenesulfonyl)-3-ureidoindol-2-one 1 ml of concentrated aqueous ammonia is added at RT to a solution of 0.400 g of the compound obtained in EXAMPLE 7 in 6 ml of EtOH and the reaction mixture is stirred for 18 hours. It is evaporated under vacuum and the residue is taken up with AcOEt, washed with water and dried over sodium sulfate. After evaporation under vacuum, the residue is chromatographed on silica using a DCM/AcOEt mixture (50/50; v/v) as the eluent to give the expected product after crystallization from a DCM/iso ether mixture. m=0.15 g. M.p.=285° C.

EXAMPLE 9

5-Chloro-3-(2-chlorophenyl)-1,3-dihydro-1-(2,4-dimethoxybenzenesulfonyl)-3-(N',N'-dimethylureido)indol-2-one This compound is prepared according to the procedure described in EXAMPLE 8 from 0.400 g of the compound obtained in EXAMPLE 7 and 0.3 ml of a 33% solution of dimethylamine in EtOH. The expected product is obtained after crystallization from a DCM/iso ether mixture. m=0.30 g. M.p.=246° C.

EXAMPLE 10

5-Chloro-3-(2-chlorophenyl)-3-(N',N'-diethylureido)-1,3-dihydro-1-(2,4-dimethoxybenzenesulfonyl)-indol-2-one A mixture of 0.460 g of the compound obtained in EXAMPLE 7, 0.082 g of diethylamine, 4 ml of chloroform and 4 ml of EtOH is heated at 60° C. for 18 hours. The reaction mixture is evaporated under vacuum and the residue is chromatographed on silica using a DCM/AcOEt mixture (95/5; v/v) as the eluent to give the expected product after crystallization from a DCM/iso ether mixture. m=0.20 g. M.p.=222° C.

EXAMPLE 11

3-Amino-5-chloro-3-(2-chlorophenyl)-1,3-di-hydro-1-(4-nitrobenzenesulfonyl)indol-2-one This compound is prepared according to the procedure described in EXAMPLE 1 from 10 g of 3-amino-5-chloro-3-(2-chlorophenyl)-1,3-dihydroindol-2-one and 7.55 g of 4-nitrobenzenesulfonyl chloride. The expected product is obtained after crystallization from a DCM/iso ether mixture. m=14 g. M.p.=202° C.

EXAMPLE 12

5-Chloro-3-(2-chlorophenyl)-3-(N',N'-diethylureido)-1,3-dihydro-1-(4-nitrobenzenesulfonyl)indol-2-one A) 5-Chloro-3-(2-chlorophenyl)-1,3-dihydro-1-(4-nitrobenzenesulfonyl)-3-(phenoxycarboxamido)indol-2-one This compound is prepared according to the procedure described in EXAMPLE 7 from 11 g of the compound obtained in EXAMPLE 11 and 4.63 g of phenyl chloroformate. Chromatography on silica using DCM as the eluent gives 12.3 g of the expected product, which is used as such in the next step.

B) 5-Chloro-3-(2-chlorophenyl)-3-(N',N'-diethylureido)-1,3-dihydro-1-(4-nitrobenzenesulfonyl)indol-2-one This compound is prepared according to the procedure described in EXAMPLE 10 from 10 g of the compound obtained in the previous step and 1.9 g of diethylamine. The expected product is obtained after crystallization from a DCM/iso ether mixture. m=7.7 g. M.p.=185° C.

EXAMPLE 13

1-(4-Aminobenzenesulfonyl)-5-chloro-3-(2-chlorophenyl)-3-(N',N'-diethylureido)-1,3-dihydroindol-2-one 7.6 g of the compound obtained in EXAMPLE 12 in 100 ml of EtOH and 50 ml of THF are reduced with hydrogen under a pressure of 50 bar for 6 hours at RT, in the presence of 2 g of Raney nickel. The mixture is filtered on Célite and the filtrate is evaporated under vacuum. The residue is chromatographed on silica using a DCM/AcOEt mixture (95/5; v/v) as the eluent to give the expected product after crystallization from a DCM/ iso ether mixture. m=3.2 g. M.p.=210° C.

EXAMPLE 14

1-[4-(tert-Butanecarboxamido)benzenesulfonyl]-5-chloro-3-(2-chlorophenyl)-3-(N',N'-diethylureido)-1,3-dihydroindol-2-one A solution of 0.400 g of the compound obtained in EXAMPLE 13 in 3 ml of pyridine is cooled to 0° C. and 0.100 g of pivaloyl chloride is added. The mixture is stirred for 18 hours, the temperature being allowed to rise to RT, and then evaporated under vacuum. The residue is extracted with AcOEt, washed with a 5% solution of potassium hydrogensulfate, dried over sodium sulfate and evaporated under vacuum. The residue is chromatographed on silica using a DCM/AcOEt mixture (95/5; v/v) as the eluent to give the expected product after crystallization from a DCM/iso ether mixture. m=0.180 g. M.p.=228° C.

EXAMPLE 15

5-Chloro-3-(2-chlorophenyl)-3-(N', N'-diethylureido)-1-[4-(N',N'-diethylureido)benzenesulfonyl]-1,3-dihydroindol-2-one A) 5-Chloro-3-(2-chlorophenyl)-3-(N',N'-diethylureido)-1,3-dihydro-1-[4-(phenoxycarboxamido)benzenesulfonyl]indol-2-one A solution of 0.500 g of the compound obtained in EXAMPLE 13 in 10 ml of pyridine is cooled to 0°–5° C. and 0.156 g of phenyl chloroformate is added. The mixture is stirred for 18 hours, the temperature being allowed to rise to RT, and then evaporated under vacuum. The residue is extracted with AcOEt, washed with a 5% solution of potassium hydrogensulfate, dried over sodium sulfate and evaporated under vacuum. The residue is chromatographed on silica using an AcOEt/ hexane mixture (30/70; v/v) as the eluent to give 0.53 g of the expected product, which is used as such in the next step.

B) 5-Chloro-3-(2-chlorophenyl)-3-(N',N'-diethylureido)-1-[4-(N',N'-diethylureido)benzenesulfonyl]-1,3-dihydroindol-2-one This compound is prepared according to the procedure described in EXAMPLE 10 from 0.53 g of the compound obtained in the previous step and 0.136 g of diethylamine. The expected product is obtained after crystallization from a DCM/iso ether mixture. m=0.24 g. M.p.=200° C.

EXAMPLE 16

3-Amino-5-chloro-3-(2-chlorophenyl)-1,3-dihydro-1-(2-methoxy-4-nitrobenzenesulfonyl)indol-2-one This compound is prepared according to the procedure described in EXAMPLE 1 from 7 g of 3-amino-5-chloro-3-(2-chlorophenyl)-1,3-dihydroindol-2-one and 6 g of 2-methoxy-4-nitrobenzenesulfonyl chloride. The expected product is obtained after crystallization from a DCM/iso ether/THF mixture. m=9.4 g. M.p.=229° C.

EXAMPLE 17

3-Amino-1-(4-amino-2-methoxybenzenesulfonyl)-5-chloro-3-(2-chlorophenyl)-1,3-dihydroindol-2-one 2.17 g of the compound obtained in EXAMPLE 16 in 30 ml of MeOH and 30 ml of THF are reduced with hydrogen under a pressure of 40 bar for 4 hours at RT, in the presence of 1 g of Raney nickel. The mixture is filtered on Célite and the filtrate is evaporated under vacuum. The residue is chromatographed on silica using DCM and then a DCM/AcOEt mixture (90/10; v/v) as the eluent to give the expected product after crystallization from a DCM/iso ether mixture. m=1.3 g. M.p.=198° C.

EXAMPLE 18 and EXAMPLE 19

5-Chloro-3-(2-chlorophenyl)-1,3-dihydro-1-[2-methoxy-4-(phenoxycarboxamido)benzenesulfonly]-3-(phenoxycarboxamido)indol-2-one (EXAMPLE 18) and 3-amino-5-chloro-3-(2-chlorophenyl)-1,3-dihydro-1-[2-methoxy-4-(phenoxycarboxamido) benzenesulfonyl]indol-2-one (EXAMPLE 19)

These compounds are prepared according to the procedure described in EXAMPLE 7 from 1.15 g of the compound obtained in EXAMPLE 17 and 0.32 ml of phenyl chloroformate. The product is chromatographed on silica using DCM and then a DCM/AcOEt mixture (95/5; v/v) as the eluent. Two compounds are separated out:

the less polar isomer: compound of EXAMPLE 18. m=0.610 g.

the more polar isomer: compound of EXAMPLE 19. m=0.406 g.

NMR spectrum at 200 MHz in DMSO-$d_6$ of the compound of EXAMPLE 18

3.45 ppm:s:3H 6.6 to 8.0 ppm:m:20H 9.3 ppm:s:1H 10.8 ppm:s: 1H

NMR spectrum at 200 MHz in DMSO-$d_6$ of the compound of EXAMPLE 19

3.1 ppm:s:2H 3.6 ppm:s:3H 6.6 to 8.3 ppm:m:15H 10.8 ppm:s:1H

EXAMPLE 20

5-Chloro-3-(2-chlorophenyl)-3-(N',N'-diethylureido)-1-[4-(N',N'-diethylureido)-2-methoxybenzenesulfonyl]-1,3-dihydroindol-2-one This compound is prepared according to the procedure described in EXAMPLE 10 from 0.610 g of the compound obtained in EXAMPLE 18 and 0.248 g of diethylamine. Chromatography on silica using a gradient of a DCM/AcOEt mixture (from 95/5; v/v to 80/20; v/v) as the eluent gives the expected product after crystallization from a DCM/iso ether mixture. m=0.456 g. M.p.=185°–190° C.

EXAMPLE 21

3-Amino-5-chloro-3-(2-chlorophenyl)-1-[4-(N',N'-diethylureido)-2-methoxybenzenesulfonyl]-1,3-dihydroindol-2-one A mixture of 0.406 g of the compound obtained in EXAMPLE 19, 0.100 g of diethylamine and 5 ml of chloroform is heated at 600° C. for 4 hours. It is evaporated under vacuum and the residue is chromatographed on silica using DCM and then a DCM/AcOEt mixture (90/10; v/v) as the eluent to give the expected product after crystallization from a DCM/iso ether mixture. m=0.280 g. M.p.=152°–158° C.

EXAMPLE 22

5-Chloro-3-(2-chlorophenyl)-1,3-dihydro-3-(methoxycarboxamido)-1-(2-methoxy-4-nitrobenzenesulfonyl)indol-2-one A solution of 2.8 g of the compound obtained in EXAMPLE 16 in 15 ml of pyridine is cooled in an ice bath and a solution of 0.85 ml of methyl chloroformate in 3 ml of DCM is added. The reaction medium is stirred for 3 days at RT and poured into water. It is extracted with AcOEt, washed with water, with a 1N solution of HCl and with water, dried over sodium sulfate and evaporated under vacuum. The residue is chromatographed on silica using DCM and then a DCM/AcOEt mixture (90/10; v/v) as the eluent to give 0.800 g of the expected product.

NMR spectrum at 200 MHz in DMSO-$d_6$ 3.4 ppm:s:3H 3.7 ppm:s:3H 7.1 to 8.3 ppm:m:10H 8.75 ppm:s:1H

EXAMPLE 23

1-(4-Amino-2-methoxybenzenesulfonyl)-5-chloro-3-(2-chlorophenyl)-1,3-dihydro-3-(methoxycarboxamido)-indol-2-one This compound is prepared according to the procedure described in EXAMPLE 17 from 0.800 g of the compound obtained in EXAMPLE 22. After filtration on Célite, the filtrate is evaporated under vacuum to give 0.742 g of the expected product.

NMR spectrum at 200 MHz in DMSO-$d_6$ 3.45 ppm:s:3H 3.55 ppm:s:3H 6.0 to 8.0 ppm:m:10H and 2H 8.65 ppm:s:1H

EXAMPLE 24

5-Chloro-3-(2-chlorophenyl)-1-[4-(N',N'-diethylureido)-2-methoxybenzenesulfonyl]-1,3-dihydro-3-(methoxycarboxamido)indol-2-one A) 5-Chloro-3-(2-chlorophenyl)-1,3-dihydro-3-(methoxycarboxamido)-1-[2-methoxy-4-(phenoxycarboxamido)-benzenesulfonly]indol-2-one This compound is prepared according to the procedure described in EXAMPLE 7 from 0.742 g of the compound obtained in EXAMPLE 23 and 0.18 ml of phenyl chloroformate. Chromatography on silica using a gradient of a DCM/AcOEt mixture (from 95/5; v/v to 80/20; v/v) as the eluent gives 0.905 g of the expected product, which is used as such in the next step.

B) 5-Chloro-3-(2-chlorophenyl)-1-[4-(N',N'-diethylureido)-2-methoxybenzenesulfonyl]-1,3-dihydro-3-(methoxycarboxamido)indol-2-one This compound is prepared according to the procedure described in EXAMPLE 10 from 0.100 g of the compound obtained in the previous step and 0.022 g of diethylamine. The expected product is obtained after crystallization from a hot EtOH/DMF mixture. m=0.050 g. M.p.=240°–245° C.

EXAMPLE 25

3-Acetamido-5-chloro-3-(2-chlorophenyl)-1,3-dihydro-1-(2-methoxy-4-nitrobenzenesulfonyl)indol-2-one A solution of 2.8 g of the compound obtained in EXAMPLE 16 in 10 ml of pyridine is cooled in an ice bath and 0.51 ml of acetyl chloride is added. The reaction medium is stirred for 3 hours at RT and poured into water. It is extracted with AcOEt, washed with water and with a 5% solution of potassium hydrogensulfate, dried over sodium sulfate and evaporated under vacuum. The residue is taken up with DCM and the precipitate formed is filtered off to give 2.8 g of the expected product, a sample of which is crystallized from an MeOH/iso ether mixture. M.p.=205°–210° C.

EXAMPLE 26

3-Acetamido-1-(4-amino-2-methoxybenzenesulfonyl)-5-chloro-3-(2-chlorophenyl)-1,3-dihydroindol-2-one This compound is prepared according to the procedure described in EXAMPLE 17 from 2.17 g of the compound obtained in EXAMPLE 25. After filtration on Célite and evaporation of the filtrate under vacuum, the residue is taken up with DCM and the precipitate formed is filtered off, washed with iso ether and dried in an oven at 90° C. to give 1.53 g of the expected product.

NMR spectrum at 200 MHz in DMSO-$d_6$ 1.8 ppm:s:3H
3.35 ppm:s:3H
5.9 to 7.9 ppm:m:10H and 2H
9.0 ppm:s:1H

EXAMPLE 27

3-Acetamido-5-chloro-3-(2-chlorophenyl)-1-[4-(N', N'-diethylureido)-2-methoxybenzenesulfonyl]-1,3-dihydroindol-2-one A) 3-Acetamido-5-chloro-3-(2-chlorophenyl)-1,3-dihydro-1-[2-methoxy-4-(phenoxycarboxamido)benzenesulfonyl]-indol-2-one This compound is prepared according to the procedure described in EXAMPLE 7 from 1.53 g of the compound obtained in EXAMPLE 26. Drying over sodium sulfate and evaporation under vacuum gives 1.60 g of the expected product, which is used as such in the next step.

B) 3-Acetamido-5-chloro-3-(2-chlorophenyl)-1-[4-(N',N'-diethylureido)-2-methoxybenzenesulfonyl]-1,3-dihydroindol-2-one This compound is prepared according to the procedure described in EXAMPLE 10 from 0.300 g of the compound obtained in the previous step and 0.068 g of diethylamine. The expected product is obtained after crystallization from a DCM/iso ether mixture. m=0.160 g. M.p.=180°–185° C.

EXAMPLE 28

3-Acetamido-1-[4-(N-tert-butylcarbamoyl)-2-methoxybenzenesulfonyl]-5-chloro-3-(2-chlorophenyl)-1,3-dihydroindol-2-one A) Benzyl 4-[3-amino-5-chloro-3-(2-chlorophenyl)-2,3-dihydro-2-oxoindol-1-yl]sulfonyl-3-methoxybenzoate This compound is prepared according to the procedure described in EXAMPLE 1 from 0.860 g of 3-amino-5-chloro-3-(2-chlorophenyl)-1,3-dihydroindol-2-one and 1 g of benzyl 4-chlorosulfonylate3-methoxybenzoate. Chromatography on silica using a DCM/AcOEt mixture (99/1; v/v) as the eluent gives 1.38 g of the expected product, which is used as such in the next step.

B) Benzyl 4-[3-acetamido-5-chloro-3-(2-chlorophenyl)-2,3-dihydro-2-oxoindol-1-yl]sulfonyl-3-methoxybenzoate A solution of 0.600 g of the compound obtained in the previous step in 4 ml of pyridine is cooled to 0° C. and a solution of 0.102 g of acetyl chloride in 2 ml of DCM is added. The reaction mixture is stirred for 30 minutes and poured into water. It is extracted with AcOEt, washed with a 5% solution of potassium hydrogensulfate, dried over sodium sulfate and evaporated under vacuum. The residue is chromatographed on silica using a DCM/AcOEt mixture (90/10; v/v) as the eluent to give the expected product after crystallization from a DCM/iso ether mixture. m=0.466 g. M.p.=177° C.

C) 4-[3-Acetamido-5-chloro-3-(2-chlorophenyl)-2,3-dihydro-2-oxoindol-1-yl]sulfonyl-3-methoxybenzoic acid A mixture of 0.400 g of the compound obtained in the previous step, 0.040 g of 10% palladium-on-charcoal and 15 ml of ACOH is hydrogenolyzed at atmospheric pressure for 30 minutes at RT. It is filtered on Célite and the filtrate is evaporated under vacuum. The residue is taken up with ether and the precipitate formed is filtered off to give 0.310 g of the expected product, which is used as such in the next step.

D) 3-Acetamido-1-[4-(N-tert-butylcarbamoyl)-2-methoxy-benzenesulfonyl]-5-chloro-3-(2-chlorophenyl)-1,3-dihydroindol-2-one A solution of 0.310 g of the compound obtained in the previous step in 8 ml of DMF is cooled to 0° C. and 0.074 g of DIPEA and then 0.269 g of BOP are added. After stirring for 15 minutes, 0.055 g of tert-butylamine is added and the mixture is stirred for 6 hours, the temperature being allowed to rise to RT. It is evaporated under vacuum and the residue is taken up with water, extracted with AcOEt, washed with a 5% solution of potassium hydrogensulfate and with water, dried over sodium sulfate and evaporated under vacuum. The residue is chromatographed on silica using a DCM/AcOEt mixture (80/20; v/v) as the eluent to give the expected product after crystallization from a DCM/iso ether mixture. m=0.15 g. M.p.=265° C.

EXAMPLE 29

3-Amino-1-[4-(N-tert-butylcarbamoyl)-2-methoxybenzenesulfonyl]-5-chloro-3-(2-chlorophenyl)-1,3-dihydroindol-2-one A) 4-[3-Amino-5-chloro-3-(2-chlorophenyl)-2,3-dihydro-2-oxoindol-1-yl]sulfonyl-3-methoxybenzoic acid This compound is prepared according to the procedure described in step C of EXAMPLE 28 from 0.700 g of the compound obtained in step A of EXAMPLE 28. After filtration on Célite and evaporation of the filtrate under vacuum, the residue is taken up with iso ether. Filtration gives 0.530 g of the expected product, which is used as such in the next step.

B) 3-Amino-1-[4-(N-tert-butylcarbamoyl)-2-methoxybenzenesulfonyl]-5-chloro-3-(2-chlorophenyl)-1,3-dihydroindol-2-one A mixture of 0.530 g of the compound obtained in the previous step, 0.134 g of DIPEA, 0.228 g of tert-butylamine and 6 ml of DMF is cooled to 0° C. and 0.483 g of BOP is added gradually. The mixture is stirred for 18 hours, the temperature being allowed to rise to RT. Water is added to the reaction medium, extraction is carried out with AcOEt and the extract is dried over sodium sulfate and evaporated under vacuum. The residue is chromatographed on silica using a DCM/AcOEt mixture (95/5; v/v) as the eluent to give the expected product after crystallization from iso ether. m=0.150 g. M.p.=263°–265° C.

EXAMPLE 30

5-Chloro-3-(2-chlorophenyl)-1-[4-(N',N'-diethylureido)benzenesulfonyl]-1,3-dihydro-3-(dimethylamino)indol-2-one This compound is prepared according to the procedure described in EXAMPLE 1 from 0.500 g of 5-chloro-3-(2-chlorophenyl)-1,3-dihydro-3-(dimethylamino)indol-2-one and 0.453 g of 4-(N',N'-diethylureido)benzenesulfonyl chloride. Chromatography on silica using a gradient of a hexane/AcOEt mixture (80/20; v/v to 60/40; v/v) as the eluent gives

EXAMPLE 31

5-Chloro-3-(2-chlorophenyl)-1-[4-(N',N'-diethyl-N-methylureido)benzenesulfonyl]-1,3-dihydro-3-(dimethylamino)indol-2-one A solution of 0.420 g of the compound obtained in EXAMPLE 30 in 7 ml of DMF is cooled to 0° C. under an argon atmosphere and 0.027 g of sodium hydride as an 80% dispersion in oil is added. After stirring for 30 minutes, 0.05 ml of methyl iodide is added and the reaction mixture is stirred for 10 minutes. It is poured into water, extracted with AcOEt, washed with water, dried over sodium sulfate and evaporated under vacuum. The residue is chromatographed on silica using DCM and then a DCM/AcOEt mixture (95/5; v/v) as the eluent to give the expected product after crystallization from a DCM/iso ether mixture. m=0.211 g. M.p.=145°–148° C.

EXAMPLE 32

3-Amino-5-chloro-1-[4-(N',N'-diethylureido)-benzenesulfonyl]-1,3-dihydro-3-(2-methoxyphenyl)indol-2-one This compound is prepared according to the procedure described in EXAMPLE 1 from 0.266 g of 3-amino-5-chloro-1,3-dihydro-3-(2-methoxyphenyl)indol-2-one and 0.280 g of 4-(N',N'-diethylureido)benzenesulfonyl chloride. The expected product is obtained after crystallization from a DCM/iso ether mixture. m=0.160 g. M.p.=214°–217° C.

EXAMPLE 33

5-Chloro-3-(2-chlorophenyl)-1-(4-ethylamino-2-methoxybenzenesulfonyl)-1,3-dihydro-3-(methoxycarboxamido)indol-2-one 2 ml of AcOH and then 0.15 ml of acetaldehyde are added at RT to a solution of 0.750 g of the compound obtained in EXAMPLE 23 in 17 ml of MeOH and 5 ml of THF, and 0.108 g of sodium cyanoborohydride is added in 10 minutes. As the reaction is immediate, 2 drops of concentrated HCl are added and the reaction medium is then neutralized by the addition of a 5% solution of potassium carbonate. The solvents are evaporated off under vacuum and the residue is extracted with AcOEt, washed with water, dried over sodium sulfate and evaporated under vacuum. The residue is chromatographed on silica using DCM and then a DCM/AcOEt mixture (97/3; v/v) as the eluent to give the expected product after crystallization from a DCM/iso ether mixture. m=0.435 g. M.p.=192°–195° C.

EXAMPLE 34

5-Chloro-3-(2-chlorophenyl)-1-(4-diethylamino-2-methoxybenzenesulfonyl)-1,3-dihydro-3-(methoxycarboxamido)indol-2-one 0.8 ml of AcOH and then 0.12 ml of acetaldehyde are added at RT to a solution of 0.311 g of the compound obtained in EXAMPLE 33 in 7 ml of MeOH and 2 ml of THF. 0.086 g of sodium cyanoborohydride is then added in 3 portions in 4 days. When the reaction has ended, 2 drops of concentrated HCl are added and the reaction medium is then neutralized by the addition of a 5% solution of potassium carbonate. The solvents are evaporated off under vacuum and the residue is extracted with AcOEt, washed with water, dried over sodium sulfate and evaporated under vacuum. The residue is chromatographed on silica using DCM and then a DCM/ AcOEt mixture (95/5; v/v) as the eluent to give the expected product after crystallization from a DCM/iso ether mixture. m=0.140 g. M.p.=210°–215° C.

EXAMPLE 35

5-Chloro-3-(2-chlorophenyl)-1-[4-(N',N'-diethylureido)benzenesulfonyl]-1,3-dihydro-3-[(1S)-1-(methoxycarbonyl)ethylamino]indol-2-one This compound is prepared according to the procedure described in EXAMPLE 1 from 0.639 g of the compound obtained in Preparation 12 (isomer A) and 0.490 g of 4-(N',N'-diethylureido)benzenesulfonyl chloride. Chromatography on silica using a DCM/AcOEt mixture (95/5; v/v) as the eluent gives the expected product after crystallization from a DCM/iso ether mixture. m=0.350 g. M.p.=204° C. $\alpha_D^{20}$=+114.5° (c=0.22; chloroform).

EXAMPLE 36

5-Chloro-3-(2-chlorophenyl)-1-[4-(N',N'-diethylureido)benzenesulfonyl]-1,3-dihydro-3-[(1S)-1-(methoxycarbonyl)ethylamino]indol-2-one This compound is prepared according to the procedure described in EXAMPLE 1 from 0.392 g of the compound obtained in Preparation 13 (isomer B) and 0.329 g of 4-(N',N'-diethylureido)benzenesulfonyl chloride. Chromatography on silica using a DCM/AcOEt mixture (95/5; v/v) as the eluent gives the expected product after crystallization from a DCM/iso ether/ hexane mixture. m=0.225 g. M.p.=204° C. $\alpha_D^{20}$=−139.4° (c=0.19; chloroform).

The compounds according to the invention collected in TABLE II below are prepared from the 1,3-dihydroindol-2-ones described in the Preparations by following the procedures described in the Examples above.

TABLE II

| Example | R₃ | R₄ | R₅ | R₆ | M.p. °C. or NMR cristallization solvent |
|---|---|---|---|---|---|
| 37 (a) | phenyl | —NH₂ | 3-OMe | 4-OMe | 150 DCM/iso ether |
| 38 (a) | 2-Cl-phenyl | —NH₂ | 3-OMe | 4-OMe | 161 DCM/iso ether |
| 39 (a) | 2-Cl-phenyl | —NH—Me | 2-OMe | 4-OMe | 205 DCM/iso ether |
| 40 (a) | 2-Cl-phenyl | —NH—Me | 3-OMe | 4-OMe | 182 DCM/iso ether |
| 41 (b) | 2-Cl-phenyl | —NH—Me | 2-OMe | 4-NO₂ | 145 DCM/iso ether |
| 42 (c) | 2-Cl-phenyl | —NH—Me | 2-OMe | 4-NH₂ | — |
| 43 (d) et (m) | 2-Cl-phenyl | —NH—Me | 2-OMe | 4-NHCON(Et)₂ | 208–210 DCM/iso ether |
| 44 (f) | 2-Cl-phenyl | —NH—Me | H | 4-NHCON(Et)₂ | 232 DCM/iso ether |
| 45 (f) | 2-Cl-phenyl | —NHCH₂Me | H | 4-NHCON(Et)₂ | 224–229 DCM/iso ether |

TABLE II-continued

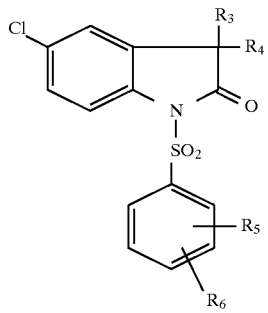

| Example | R₃ | R₄ | R₅ | R₆ | M.p. °C. or NMR cristallization solvent |
|---|---|---|---|---|---|
| 46 (f) | 2-Cl-phenyl | —NHCH₂CH₂Me | H | 4-NHCON(Et)₂ | 160–164 DCM/iso ether |
| 47 (f) | 2-Cl-phenyl | —NH(CH₂)₄Me | H | 4-NHCON(Et)₂ | 219–221 DCM/iso ether |
| 48 (f) | 2-Cl-phenyl | —NH—C(Me)₃ | H | 4-NHCON(Et)₂ | 220–223 DCM/iso ether |
| 49 (f) | 2-Cl-phenyl | —NHCH₂CH(Me)₂ | H | 4-NHCON(Et)₂ | 177 DCM/iso ether |
| 50 (f) | 2-Cl-phenyl | —NHCH₂-phenyl | H | 4-NHCON(Et)₂ | 246–248 DCM/iso ether |
| 51 (a) | 2-Cl-phenyl | —N(Me)₂ | 2-OMe | 4-OMe | 215–217 DCM/iso ether |
| 52 (a) | 2-Cl-phenyl | —N(Me)₂ | 3-OMe | 4-OMe | 168–170 DCM/iso ether |
| 53 (g) | 2-Cl-phenyl | —N(Me)₂ | H | 4-NO₂ | 245–247 DCM/iso ether |
| 54 (h) | 2-Cl-phenyl | —N(Me)₂ | H | 4-NH₂ | NMR |

TABLE II-continued

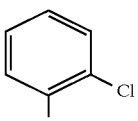

| Example | $R_3$ | $R_4$ | $R_5$ | $R_6$ | M.p. °C. or NMR cristallization solvent |
|---|---|---|---|---|---|
| 55 (b) | 2-Cl-phenyl | —N(Me)Me | 2-OMe | 4-NO$_2$ | NMR |
| 56 (c) | 2-Cl-phenyl | —N(Me)Me | 2-OMe | 4-NH$_2$ | 155–158 DCM/hexane |
| 57 (d) et (m) | 2-Cl-phenyl | —N(Me)Me | 2-OMe | 4-NHCON(Et)Et | 205–210 DCM/iso ether |
| 58 (a) | 2-Cl-phenyl | —N(Et)Et | 2-OMe | 4-OMe | 180–185 DCM/iso ether |
| 59 (g) | 2-Cl-phenyl | —N(Et)Et | H | 4-NO$_2$ | 198–205 DCM/iso ether |
| 60 (h) | 2-Cl-phenyl | —N(Et)Et | H | 4-NH$_2$ | 205–208 DCM/iso ether |
| 61 (n) | 2-Cl-phenyl | —N(Et)Et | H | 4-NHCON(Et)Et | 176–180 DCM/iso ether |
| 62 (f) | 2-Cl-phenyl | —NHCH$_2$CH$_2$OMe | H | 4-NHCON(Et)Et | 149–151 DCM/iso ether |
| 63 (f) | 2-Cl-phenyl | —NHCH$_2$CH$_2$N(Et)Et | H | 4-NHCON(Et)Et | 165 DCM/iso ether |

TABLE II-continued

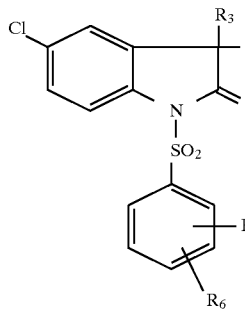

| Example | R₃ | R₄ | R₅ | R₆ | M.p. °C. or NMR cristallization solvent |
|---|---|---|---|---|---|
| 64 (a) | 2-Cl-phenyl | —NH—CH₂—CO₂Et | 2-OMe | 4-OMe | 178 DCM/iso ether |
| 65 (a) | 2-Cl-phenyl | —N(piperazine)N—Boc | 2-OMe | 4-OMe | 244 DCM/iso ether |
| 66 (i) | 2-Cl-phenyl | —NHCOMe | 2-OMe | 4-OMe | 220–223 DCM/iso ether |
| 67 (i) | 2-Cl-phenyl | —NHCOisoBu | 2-OMe | 4-OMe | 255 DCM/iso ether |
| 68 (i) | 2-Cl-phenyl | —NHCO-cyclohexyl | 2-OMe | 4-OMe | 260 DCM/iso ether |
| 69 (j) | 2-Cl-phenyl | —NHCOOEt | 2-OMe | 4-OMe | 199 DCM/iso ether |
| 70 (j) | 2-Cl-phenyl | —NHCOOisoBu | 2-OMe | 4-OMe | 299 DCM/iso ether |
| 71 (k) | 2-Cl-phenyl | —NH—CO—N(Et)(Et) | H | 4-NHCO—CH(Et)(Et) | 188 DCM/iso ether |
| 72 (e) | 2-Cl-phenyl | —NHCON(CH₂)₂N(Me)(Et)(Et) | 2-OMe | 4-OMe | 180 DCM/iso ether |

TABLE II-continued

[Structure: 5-chloro-indolin-2-one with R3, R4 at 3-position, N-SO2-phenyl with R5, R6 substituents]

| Example | R₃ | R₄ | R₅ | R₆ | M.p. °C. or NMR cristallization solvent |
|---|---|---|---|---|---|
| 73 (e) | 2-Cl-phenyl | —NHCON(CH₂)₂N(Me)Me (with N-Me) | 2-OMe | 4-OMe | NMR DCM/iso ether |
| 74 (d) et (m) | 2-Cl-phenyl | —NHCOMe | 2-OMe | 4-NHCON(Et)(iPr) | 190–200 DCM/iso ether |
| 75 (d) et (m) | 2-Cl-phenyl | —NHCOMe | 2-OMe | 4-NHCONH-cycloheptyl | 190–200 DCM/iso ether |
| 76 (d) et (m) | 2-Cl-phenyl | —NHCOMe | 2-OMe | 4-NHCON(thiomorpholine) | 255–260 DCM/iso ether |
| 77 (a) | 2-Cl-phenyl | —N₃ | 2-OMe | 4-OMe | 122–125 DCM/iso ether |
| 78 (b) | 2-OMe-phenyl | —NH₂ | 2-OMe | 4-NO₂ | 198–200 DCM/iso ether |
| 79 (c) | 2-OMe-phenyl | —NH₂ | 2-OMe | 4-NH₂ | 229–232 THF/iso ether |
| 80 (l) et (m) | 2-OMe-phenyl | —NH₂ | 2-OMe | 4-NHCON(Et)(Et) | NMR DCM/iso ether |
| 81 (l) et (m) | 2-OMe-phenyl | —NHCON(Me)Me | 2-OMe | 4-NHCON(Me)Me | 204–210 DCM/iso ether |

TABLE II-continued

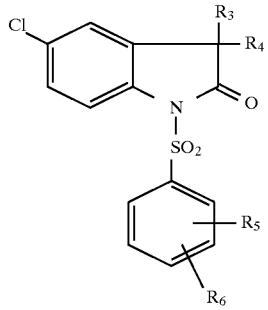
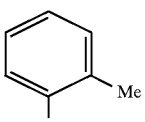

| Example | R₃ | R₄ | R₅ | R₆ | M.p. °C. or NMR cristallization solvent |
|---|---|---|---|---|---|
| 82 (f) | (o-tolyl) | —NH₂ | H | 4-NHCON(Et)(Et) | 170–176 DCM/iso ether |

(a) Compound prepared according to the procedure described in EXAMPLE 1.

(b) Compound prepared according to the procedure described in EXAMPLE 16.

(c) Compound prepared according to the procedure described in EXAMPLE 17.

(d) Compound prepared according to the procedure described in step A of EXAMPLE 27.

(e) Compound prepared according to the procedure described in EXAMPLE 10 by using the appropriate amines or the appropriate heterocycles.

(f) Compound prepared according to the procedure described in EXAMPLE 30.

(g) Compound prepared according to the procedure described in EXAMPLE 11.

(h) Compound prepared according to the procedure described in EXAMPLE 13.

(i) Compound prepared according to the procedure described in EXAMPLE 4 by using the appropriate acid chlorides.

(j) Compound prepared according to the procedure described in EXAMPLE 5 by using the appropriate chloroformates.

(k) Compound prepared according to the procedure described in EXAMPLE 14 by using the appropriate acid chlorides.

(l) Compound prepared according to the procedure described in EXAMPLES 18 and 19.

(m) Compound prepared according to the procedure described in step B of EXAMPLE 27 by using the appropriate amines or the appropriate heterocycles.

(n) Compound prepared according to the procedures described in step A and then step B of EXAMPLE 15.

NMR spectrum at 200 MHz in DMSO-$d_6$ of the compound of EXAMPLE 54

2.05 ppm:bs:3H
2.3 ppm:bs:3H
6.5 ppm:s:2H
6.6 to 8.2 ppm:m:11H

NMR spectrum at 200 MHz in DMSO-$d_6$ of the compound of EXAMPLE 55

1.8 to 2.4 ppm:mt:6H
3.8 ppm:s:3H
6.9 ppm:d:1H
7.2 to 7.8 ppm:mt:4H
7.9 ppm:d:1H
8.1 ppm:mt:3H
8.4 ppm:d:1H NMR spectrum at 200 MHz in DMSO-$d_6$ of the compound of EXAMPLE 73

1.9 ppm:s:6H
2.2 ppm:mt:3H
3.1 ppm:t:2H
3.4 ppm:s:3H
3.8 ppm:s:3H
6.6 to 7.8 ppm:10H
8.2 to 8.8 ppm:bs:1H NMR spectrum at 200 MHz in DMSO-$d_6$ of the compound of EXAMPLE 80

1.1 ppm:t:6H
2.7 ppm:s:2H
3.2 to 3.5 ppm:qd+s:7H
6.9 ppm:mt:2H
7.1 ppm:t:1H
7.3 to 7.5 ppm:mt:3H
7.6 ppm:s:1H
7.75 to 8.1 ppm:t:of d 3H
8.8 ppm:s:1H

EXAMPLE 83

5-Chloro-3-(2-chlorophenyl)-1,3-dihydro-1-(2,4-dimethoxybenzenesulfonyl)-3-(piperazin-1-yl)indol-2-one A solution of 0.300 g of the compound obtained in EXAMPLE 65 in 5 ml of DCM is cooled to 0° C. and 5 ml of TFA are added. The mixture is stirred for 2 hours at 0° C.

and evaporated under vacuum. The residue is taken up with a 5% solution of potassium carbonate, extracted with AcOEt, dried over sodium sulfate and evaporated under vacuum. The residue is chromatographed on silica using a DCM/MeOH mixture (90/10; v/v) as the eluent to give the expected product after crystallization from a DCM/iso ether mixture. m=0.105 g. M.p.=210° C.

EXAMPLE 84

3-Amino-5,6-dichloro-1-[4-(N',N'-diethylureido)-benzenesulfonyl]-1,3-dihydro-3-phenylindol-2-one This compound is prepared according to the procedure described in EXAMPLE 1 from 0.293 g of 3-amino-5,6-dichloro-1,3-dihydro-3-phenylindol-2-one and 0.290 g of 4-(N',N'-diethylureido)benzenesulfonyl chloride. Chromatography on silica using a DCM/AcOEt mixture (85/15; v/v) as the eluent gives the expected product after crystallization from a DCM/iso ether mixture. m=0.26 g. M.p.=119°–121° C.

EXAMPLE 85

3-Amino-4,5-dichloro-1-[4-(N',N'-diethylureido)-benzenesulfonyl]-1,3-dihydro-3-phenylindol-2-one This compound is prepared according to the procedure described in EXAMPLE 1 from 0.4 g of 3-amino-4,5-dichloro-1,3-dihydro-3-phenylindol-2-one and 0.4 g of 4-(N',N'-diethylureido)benzenesulfonyl chloride. Chromatography on silica using a DCM/AcOEt mixture (85/15; v/v) as the eluent gives the expected product after crystallization from a DCM/iso ether mixture. m=0.46 g. M.p.=161°–163° C.

EXAMPLE 86

5-Ethoxy-3-(2-ethoxycarbonyl-1-ethoxycarbonylhydrazino)-1,3-dihydro-1-(2,4-dimethoxybenzenesulfonyl)-3-phenylindol-2-one This compound is prepared according to the procedure described in EXAMPLE 1 from 0.500 g of 5-ethoxy-3-(2-ethoxycarbonyl-1-ethoxycarbonylhydrazino)-1,3-dihydro-3-phenylindol-2-one and 0.280 g of 2,4-dimethoxybenzenesulfonyl chloride. The expected product is obtained after crystallization from a DCM/iso ether mixture. m=0.383 g. M.p.=228°–229° C.

EXAMPLE 87

3-Amino-3-(2-chlorophenyl)-5-ethoxy-1-[4-(N',N'-diethylureido)benzenesulfonyl]-1,3-dihydroindol-2-one This compound is prepared according to the procedure described in EXAMPLE 30 from 3-amino-3-(2-chlorophenyl)-5-ethoxy-1,3-dihydroindol-2-one and 4-(N',N'-diethylureido)benzenesulfonyl chloride.

NMR spectrum at 200 MHz in DMSO-$d_6$ 1.0 ppm:t:6H
1.1 ppm:t:3H
2.95 ppm:s:2H
3.3 ppm:qd:4H
6.2 ppm:d:1H
6.9 ppm:d of d:1H
7.1 ppm:d:1H
7.25 ppm:t:1H
7.4 ppm:t:1H
7.6 to 7.9 ppm:mt:5H
8.1 ppm:d:1H
8.7 ppm:s:1H

EXAMPLE 88

3-Amino-3-(2-chlorophenyl)-5-ethoxy-1,3-dihydro-1-(2,4-dimethoxybenzenesulfonyl)indol-2-one This compound is prepared according to the procedure described in EXAMPLE 1 from 3-amino-3-(2-chlorophenyl)-5-ethoxy-1,3-dihydroindol-2-one and 2,4-dimethoxybenzenesulfonyl chloride. The expected product is obtained after crystallization from a DCM/ hexane/iso ether mixture. M.p.=196°–198° C.

EXAMPLE 89

Methyl 4-[3-amino-5-chloro-3-(2-chlorophenyl)-2,3-dihydro-2-oxoindol-1-yl]methyl-3-methoxybenzoate A solution of 1.13 g of 3-amino-5-chloro-3-(2-chlorophenyl)-1,3-dihydroindol-2-one in 7 ml of DMF is cooled to 0° C. under an argon atmosphere and 0.120 g of sodium hydride as an 80% dispersion in oil is added. After stirring for 30 minutes, 1 g of methyl 4-bromomethyl-3-methoxybenzoate is added and the reaction mixture is stirred for 1 hour at 0° C. It is poured into water and the precipitate formed is filtered off, washed with water, taken up with AcOEt, dried over sodium sulfate and evaporated under vacuum. The residue is chromatographed on silica using a DCM/AcOEt mixture (93/7; v/v) as the eluent to give the expected product after crystallization from a DCM/iso ether mixture. m=1.88 g. M.p.=152° C.

EXAMPLE 90

Methyl 4-[5-chloro-3-(2-chlorophenyl)-2,3-dihydro-3-(methoxycarboxamido)-2-oxoindol-1-yl]methyl-3-methoxybenzoate A mixture of 1.67 g of the compound obtained in EXAMPLE 89 and 10 ml of pyridine is cooled to 0° C. and a solution of 0.669 g of methyl chloroformate in 2 ml of DCM is added. The reaction mixture is stirred for 1 hour at between 0° and +4° C. and poured into water. It is extracted with DCM, washed with a 5% solution of potassium hydrogensulfate, dried over sodium sulfate and evaporated under vacuum. The residue is chromatographed on silica using a DCM/AcOEt mixture (95/5; v/v) as the eluent to give the expected product after crystallization from a DCM/ iso ether mixture. m=1.6 g. M.p.=174° C.

EXAMPLE 91

1-[4-(N-tert-Butylcarbamoyl)-2-methoxybenzyl]-5-chloro-3-(2-chlorophenyl)-1,3-dihydro-3-(methoxy-carboxamido)indol-2-one A) 4-[5-Chloro-3-(2-chlorophenyl)-2,3-dihydro-3-(methoxycarboxamido)-2-oxoindol-1-yl]methyl-3-methoxybenzoic acid 0.317 g of lithium hydroxide monohydrate is added to a mixture of 0.8 g of the compound obtained in EXAMPLE 90, 9 ml of THF, 9 ml of MeOH and 3 ml of water and the reaction mixture is stirred for 4 hours at RT. Water is then added and the mixture is acidified to pH 1 by the addition of 1N HCl, extracted with DCM, dried over sodium sulfate and evaporated under vacuum to give the expected product, which is used as such in the next step.

B) 1-[4-(N-tert-Butylcarbamoyl)-2-methoxybenzyl]-5-chloro-3-(2-chlorophenyl)-1,3-dihydro-3-(methoxycarboxamido)indol-2-one A solution of 0.450 g of the compound obtained in the previous step in 10 ml of DCM is cooled to 0° C., 0.113 g of DIPEA and 0.403 g of BOP are added and the mixture is stirred for 15 minutes. 0.095 g of tert-butylamine is then added and the mixture is stirred for 3 hours at 0° C. Water is added and the mixture is extracted with DCM, washed with a 5% solution of potassium hydrogensulfate, dried over sodium sulfate and evaporated under vacuum. The residue is chromatographed on silica using a DCM/AcOEt mixture (90/10; v/v) as the eluent to give the expected product after crystallization from a DCM/iso ether mixture. m=0.260 g. M.p.=215° C.

EXAMPLE 92

3-Amino-1-[4-(N-tert-butylcarbamoyl)-2-methoxybenzyl]-5-chloro-3-(2-chlorophenyl)-1,3-dihydroindol-2-one A mixture of 0.70 g of the compound obtained in EXAMPLE 91 and 35 ml of a 33% solution of hydrobromic acid in AcOH is stirred for 2 hours at RT. It is evaporated under vacuum and the residue is taken up with water, rendered alkaline to pH 10 by the addition of sodium carbonate, extracted with AcOEt, dried over sodium sulfate and evaporated under vacuum. The residue is chromatographed on silica using DCM and then a DCM/AcOEt mixture (80/20; v/v) as the eluent to give the expected product after crystallization from a DCM/ iso ether mixture. m=0.370 g. M.p.=234° C.

EXAMPLE 93 tert-Butyl 4-[5-chloro-3-(2-chlorophenyl)-2,3-dihydro-3-dimethylamino-2-oxoindol-1-yl]methylbenzoate This compound is prepared according to the procedure described in EXAMPLE 89 from 1.5 g of 5-chloro-3-(2-chlorophenyl)-1,3-dihydro-3-dimethylaminoindol-2-one and 1.40 g of tert-butyl 4-bromomethylbenzoate. Chromatography on silica using a gradient of an AcOEt/ hexane mixture (from 10/90; v/v to 20/80; v/v) as the eluent gives the expected product. m=1.5 g.

NMR spectrum at 200 MHz in DMSO-$d_6$
1.5 ppm:s:9H
2.0 to 2.4 ppm:m:6H
4.8 to 5.2 ppm:d of d:2H
6.8 ppm:d:1H
7.0 ppm:d:1H
7.2 to 7.6 ppm:mt:6H
7.8 ppm:d:2H
8.1 ppm:d:1H

EXAMPLE 94

1-[4-(N-tert-Butylcarbamoyl)benzyl]-5-chloro-3-(2-chlorophenyl)-1,3-dihydro-3-dimethylaminoindol-2-one A) 4-[5-Chloro-3-(2-chlorophenyl)-2,3-dihydro-3-dimethylamino-2-oxoindol-1-yl]methylbenzoic acid A solution of 0.615 g of the compound obtained in EXAMPLE 93 in 2 ml of DCM is cooled to 0° C. and 2 ml of TFA are added. The mixture is stirred for 30 minutes and evaporated under vacuum and the residue is then taken up with DCM and evaporated under vacuum again to give the expected product, which is used as such in the next step.

B) 1-[4-(N-tert-Butylcarbamoyl)benzyl]-5-chloro-3-(2-chlorophenyl)-1,3-dihydro-3-dimethylaminoindol-2-one A solution of 0.546 g of the compound obtained in the previous step in 5 ml of DCM is cooled to 0° C. and neutralized to pH 7 by the addition of DIPEA, and 0.530 g of BOP is then introduced. The pH is readjusted to 7 by the addition of DIPEA, 0.2 ml of tert-butylamine is added and the mixture is stirred for 16 hours, the temperature being allowed to rise to RT. It is evaporated under vacuum, extracted with AcOEt, washed with a 5% solution of sodium carbonate, dried over sodium sulfate and evaporated under vacuum. The residue is chromatographed on silica using a gradient of a hexane/AcOEt mixture (from 80/20; v/v to 70/30; v/v) as the eluent to give the expected product after crystallization from a DCM/iso ether mixture. m=0.280 g. M.p.=158° C.

EXAMPLE 95

5-Chloro-3-(2-chlorophenyl)-1-[4-(N-1-ethylpropylcarbamoyl)benzyl]-1,3-dihydro-3-dimethylamino-indol-2-one This compound is prepared according to the procedure described in step B of EXAMPLE 94 from 0.623 g of the compound obtained in step A of EXAMPLE 94 and 0.24 ml of 1-ethylpropylamine, in the presence of 0.605 g of BOP and in the presence of DIPEA in order to maintain a pH of 7. Chromatography on silica using a gradient of a hexane/AcOEt mixture (from 90/10; v/v to 70/30; v/v) as the eluent gives the expected product after crystallization from a DCM/hexane mixture. m=0.490 g. M.p.=208° C.

EXAMPLE 96

3-Amino-1-[4-(N-tert-butylcarbamoyl)benzyl]-5-chloro-3-(2-chlorophenyl)-1,3-dihydroindol-2-one A) tert-Butyl 4-[3-amino-5-chloro-3-(2-chlorophenyl)-2,3-dihydro-2-oxoindol-1-yl]methylbenzoate This compound is prepared according to the procedure described in EXAMPLE 89 from 1.0 g of 3-amino-5-chloro-3-(2-chlorophenyl)-1,3-dihydroindol-2-one and 1.01 g of tert-butyl 4-bromomethylbenzoate. Chromatography on silica using DCM and then a DCM/AcOEt mixture (95/5; v/v) as the eluent gives 0.98 g of the expected product, which is used as such in the next step.

B) 4-[3-Amino-5-chloro-3-(2-chlorophenyl)-2,3-dihydro-2-oxoindol-1-yl]methylbenzoic acid A solution of 0.98 g of the compound obtained in the previous step in 2 ml of DCM is cooled to 0° C. and 4.5 ml of TFA are added. The mixture is stirred for 30 minutes and evaporated under vacuum and the residue is then taken up with DCM and evaporated under vacuum again to give the expected product, which is used as such in the next step.

C) 3-Amino-1-[4-(N-tert-butylcarbamoyl)benzyl]-5-chloro-3-(2-chlorophenyl)-1,3-dihydroindol-2-one A solution of 0.867 g of the compound obtained in the previous step in 8 ml of DCM is cooled to 0° C. and neutralized to pH 7 by the addition of DIPEA, and 1.12 g of BOP are then introduced. The pH is re-adjusted to 7 by the addition of DIPEA, 0.64 ml of tert-butylamine is added and the mixture is stirred for 16 hours, the temperature being allowed to rise to RT. It is evaporated under vacuum, extracted with AcOEt, washed with a 5% solution of sodium carbonate, dried over sodium sulfate and evaporated under vacuum. The residue is chromatographed on silica using a gradient of a hexane/AcOEt mixture (from 80/20; v/v to 70/30; v/v) as the eluent to give the expected product after crystallization from a DCM/MeOH/iso ether mixture. m=0.610 g. M.p.=173°–178° C.

EXAMPLE 97

3-Acetamido-3-(2-chlorophenyl)-5-ethoxy-1-[4-(N',N'-diethylureido)benzenesulfonyl]-1,3-dihydroindol-2-one This compound is prepared according to the procedure described in EXAMPLE 2 from the compound obtained in EXAMPLE 87 and acetyl chloride. Crystallization from a DCM/iso ether mixture gives the expected product, which crystallizes with 0.25 mol of iso ether.

NMR spectrum at 200 MHz in DMSO-$d_6$ 1.0 ppm:t and d:6H and 12H (iso ether)
1.2 ppm:t:3H
1.8 ppm:s:3H
3.3 ppm:qd:4H
3.55 ppm:sep:2H (iso ether)
3.9 ppm:qd:2H
6.7 ppm:d:1H
6.9 ppm:d of d:1H
7.2 to 7.4 ppm:mt:4H
7.6 to 7.9 ppm:mt:5H
8.7 ppm:s:1H
9.1 ppm:s:1H

EXAMPLE 98

3-Amino-3-(2-chlorophenyl)-5-ethoxy-1,3-dihydro-1-(2-methoxy-4-nitrobenzenesulfonyl)indol-2-one This compound is prepared according to the procedure described in EXAMPLE 16 from 3-amino-3-(2-chlorophenyl)-5-ethoxy-1,3-dihydroindol-2-one and 2-methoxy-4-nitrobenzenesulfonyl chloride. Crystallization from a DCM/iso ether mixture gives the expected product, which crystallizes with 0.25 mol of iso ether. M.p.=129°–132° C.

EXAMPLE 99

3-Amino-5-chloro-3-(2-chlorophenyl)-1-[4-(N',N'-diethylureido)benzenesulfonyl]-1,3-dihydroindol-2-one This compound is prepared according to the procedure described in EXAMPLE 30 from 3-amino-5-chloro-3-(2-chlorophenyl)-1,3-dihydroindol-2-one and 4-(N',N'-diethylureido)benzenesulfonyl chloride. M.p.=195°–196° C.

EXAMPLE 100

3-(2-Chlorophenyl)-5-ethoxy-1-[4-(N',N'-diethylureido)-2-methoxybenzenesulfonyl]-1,3-dihydro-3-(methoxycarboxamido)indol-2-one This compound is prepared according to the procedures described in EXAMPLES 22, then 23 and then 24 from the compound obtained in EXAMPLE 98. The expected product is obtained after crystallization from chloroform. M.p.=263°–266° C.

EXAMPLE 101

3-Amino-3-(2-chlorophenyl)-5-ethoxy-1-[4-(N',N'-diethylureido)-2-methoxybenzenesulfonyl]-1,3-dihydroindol-2-one hemihydrate This compound is prepared according to the procedure described in EXAMPLE 92 from the compound obtained in EXAMPLE 100. M.p.=218°–220° C.

EXAMPLE 102

5-Chloro-3-(cyclohexylmethyl)-1,3-dihydro-1-(2-methoxy-4-nitrobenzenesulfonyl)-3-(methylamino)indol-2-one This compound is prepared according to the procedure described in EXAMPLE 16 from 1.49 g of 5-chloro-3-(cyclohexylmethyl)-1,3-dihydro-3-(methylamino)indol-2-one and 1.8 g of 2-methoxy-4-nitrobenzenesulfonyl chloride. Chromatography on silica using DCM and then a DCM/AcOEt mixture (95/5; v/v) as the eluent gives 1.5 g of the expected product after crystallization from AcOEt. M.p.=207° C.

EXAMPLE 103

5-Chloro-3-(cyclohexylmethyl)-1-[4-(N',N'-diethylureido)-2-methoxybenzenesulfonyl]-1,3-dihydro-3-(methylamino)indol-2-one A) 5-Chloro-3-(cyclohexylmethyl)-1,3-dihydro-1-(2-methoxy-4-nitrobenzenesulfonyl)-3-(N-methylmethoxycarboxamido)indol-2-one A solution of 1.62 g of the compound obtained in EXAMPLE 102 in 10 ml of pyridine is cooled to +4° C., a solution of 0.27 ml of methyl chloroformate in 5 ml of DCM is added dropwise and the mixture is stirred for 3 hours at +4° C. 50 ml of water are added to the reaction mixture, extraction is carried out with AcOEt, the organic phase is washed with a saturated solution of sodium chloride and with water and dried over sodium sulfate and the solvent is evaporated off under vacuum. The residue is chromatographed on silica using DCM as the eluent to give 1.14 g of the expected product after crystallization from a DCM/iso ether mixture.

NMR spectrum at 200 MHz in DMSO-$d_6$ 0.5 to 1.7 ppm:m:11H
1.9 ppm:mt:2H
3.1 ppm:s:3H
3.3 ppm:s:3H
3.7 ppm:s:3H
7.4 to 8.4 ppm:m:6H B) 1-(4-Amino-2-methoxybenzenesulfonyl)-5-chloro-3-(cyclohexylmethyl)-1,3-dihydro-3-(N-methylmethoxycarboxamido)indol-2-one A mixture of 1.14 g of the compound obtained in the previous step, 0.5 g of Raney® nickel and 50 ml of MeOH is hydrogenated at atmospheric pressure for 20 minutes at RT. The catalyst is filtered off on Célite® and the filtrate is evaporated under vacuum to give 1.19 g of the expected product after crystallization from MeOH.

NMR spectrum at 200 MHz in DMSO-$d_6$
0.4 to 1.6 ppm:m:11H
1.8 ppm:mt:2H
3.15 ppm:s:3H
3.35 ppm:s:3H
3.55 ppm:s:3H
6.1 to 7.9 ppm:m:8H C) 5-Chloro-3-(cyclohexylmethyl)-1,3-dihydro-3-(N-methylmethoxycarboxamido)-1-[2-methoxy-4-(phenoxycarboxamido)benzenesulfonyl]indol-2-one A solution of 1.19 g of the compound obtained in the previous step in 10 ml of pyridine is cooled to +4° C., a solution of 0.3 ml of phenyl chloroformate in 10 ml of DCM is added dropwise and the mixture is stirred for 3 hours at RT. 50 ml of water are added to the reaction mixture, extraction is carried out with AcOEt, the organic phase is washed with a saturated solution of NaCl and with water and dried over sodium sulfate and the solvent is evaporated off under vacuum. The residue is chromatographed on silica using DCM and then a DCM/AcOEt mixture (95/5; v/v) as the eluent to give 0.755 g of the expected product after crystallization from a DCM/iso ether mixture.

D) 5-Chloro-3-(cyclohexylmethyl)-1-[4-(N',N'-diethylureido)-2-methoxybenzenesulfonyl]-1,3-dihydro-3-(N-methylmethoxycarboxamido)indol-2-one 0.09 ml of diethylamine is added to a solution of 0.268 g of the compound obtained in the previous step in 15 ml of chloroform and the reaction mixture is heated at 60° C. for 3 hours. It is concentrated under vacuum and the residue is chromatographed on silica using DCM and then a DCM/AcOEt mixture (85/15; v/v) as the eluent to give 0.18 g of the expected product after crystallization from a DCM/iso ether mixture.

NMR spectrum at 200 MHz in DMSO-$d_6$
0.4 to 2.1 ppm:m:19H
3.15 ppm:s:3H
3.35 ppm:m:7H
3.6 ppm:s:3H
7.2 to 7.9 ppm:m:6H
8.65 ppm:s:1H E) 5-Chloro-3-(cyclohexylmethyl)-1-[4-(N',N'-diethylureido)-2-methoxybenzenesulfonyl]-1,3-dihydro-3-(methylamino)indol-2-one This compound is prepared according to the procedure described in EXAMPLE 92 from the compound obtained in the previous step. The expected product is obtained after crystallization from a DCM/iso ether mixture. M.p.=210° C.

EXAMPLE 104

5-Chloro-3-(cyclohexylmethyl)-1-[4-(N',N'-diethylureido)-2-methoxybenzenesulfonyl]-1,3-dihydro-3-(N-methylphenoxycarboxamido)indol-2-one A) 1-(4-Amino-2-methoxybenzenesulfonyl)-5-chloro-3-(cyclohexylmethyl)-1,3-dihydro-3-(methylamino)indol-2-one A mixture of 1.2 g of the compound obtained in EXAMPLE 102, 3 g of Raney® nickel, 30 ml of MeOH and 40 ml of THF is hydrogenated at atmospheric pressure and at RT. After 40 minutes, the catalyst is filtered off on Célite® and the filtrate is evaporated under vacuum. The residue is chromatographed on silica using DCM and then a DCM/AcOEt mixture (75/25; v/v) as the eluent to give 0.6 g of the expected product, which is used as such in the next step.

B) 5-Chloro-3-(cyclohexylmethyl)-1,3-dihydro-1-[2-methoxy-4-(phenoxycarboxamido)benzenesulfonyl]-3-(N-methylphenoxycarboxamido)indol-2-one A solution of 0.6 g of the compound obtained in the previous step in 2 ml of pyridine is cooled to +4° C., a solution of 0.17 ml of phenyl chloroformate in 3 ml of DCM is added dropwise and the mixture is stirred for 4 hours, the temperature being allowed to rise to RT. 40 ml of water are added to the reaction mixture, extraction is carried out with AcOEt, the organic phase is washed with a saturated solution of sodium chloride and with water and dried over sodium sulfate and the solvent is evaporated off under vacuum to give 0.9 g of the expected product, which is used as such in the next step.

C) 5-Chloro-3-(cyclohexylmethyl)-1-[4-(N',N'-diethylureido)-2-methoxybenzenesulfonyl]-1,3-dihydro-3-(N-methylphenoxycarboxamido)indol-2-one 0.31 ml of diethylamine is added to a solution of 0.9 g of the compound obtained in the previous step in 5 ml of chloroform and the mixture is heated at 60° C. for 4 hours. 50 ml of water are added to the reaction mixture, extraction is carried out with AcOEt, the organic phase is washed with a saturated solution of sodium chloride and with water and dried over sodium sulfate and the solvent is evaporated off under vacuum. The residue is chromatographed on silica using DCM and then a DCM/AcOEt mixture (85/15; v/v) as the eluent to give 0.45 g of the expected product after crystallization from a DCM/iso ether mixture. M.p.=130° C.

EXAMPLE 105

3-Amino-5-chloro-3-(2-chlorophenyl)-1,3-dihydro-1-(4-methoxy-2-nitrobenzenesulfonyl)indol-2-one This compound is prepared according to the procedure described in EXAMPLE 1 from 2 g of 3-amino-5-chloro-3-(2-chlorophenyl)-1,3-dihydroindol-2-one and 1.71 g of 4-methoxy-2-nitrobenzenesulfonyl chloride. Chromatography on silica using a DCM/hexane mixture (80/20; v/v) and then DCM as the eluent gives 2.8 g of the expected product after crystallization from a DCM/ iso ether mixture. M.p.=192°–195° C.

EXAMPLE 106

3-Amino-1-(2-amino-4-methoxybenzenesulfonyl)-5-chloro-3-(2-chlorophenyl)-1,3-dihydroindol-2-one A mixture of 2.4 g of the compound obtained in EXAMPLE 105, 1 g of Raney® nickel, 50 ml of MeOH and 50 ml of THF is hydrogenated at atmospheric pressure for 1 hour at RT. The catalyst is filtered off on Célite® and the filtrate is evaporated under vacuum. The residue is chromatographed on silica using DCM and then a DCM/AcOEt mixture (95/5; v/v) as the eluent to give 0.316 g of the expected product after crystallization from a DCM/iso ether mixture. M.p.=160°–166° C.

EXAMPLE 107

3-Amino-5-chloro-3-(2-chlorophenyl)-1-[2-(ethylamino)-4-methoxybenzenesulfonyl]-1,3-dihydro-indol-2-one 2.6 ml of AcOH and then 0.09 ml of acetaldehyde and 0.038 g of sodium cyanoborohydride are added at RT to a solution of 0.830 g of the compound obtained in EXAMPLE 106 in 22 ml of MeOH. After stirring for 4 hours at RT, 2 drops of concentrated HCl are added and the reaction mixture is then neutralized by the addition of a 5% solution of potassium carbonate. The solvent is concentrated under vacuum, the residue is extracted with AcOEt, the organic phase is washed with water and with a saturated solution of sodium chloride and dried over sodium sulfate and the solvent is evaporated off under vacuum. The residue is chromatographed on silica using a DCM/hexane mixture (80/20; v/v) and then DCM as the eluent to give 0.396 g of the expected product after crystallization from a DCM/iso ether mixture. M.p.=192°–196° C.

EXAMPLE 108

3-Amino-5-chloro-3-(2-chlorophenyl)-1-[4-(N',N'-diethylureido)benzenesulfonyl]-1,3-dihydroindol-2-one, (+) isomer This compound is prepared according to the procedure described in EXAMPLE 30 from 0.293 g of 3-amino-5-chloro-3-(2-chlorophenyl)-1,3-dihydroindol-2-one, (+) isomer, and 0.290 g of 4-(N',N'-diethylureido) benzenesulfonyl chloride. Chromatography on silica using a DCM/AcOEt mixture (90/10; v/v) as the eluent gives 0.24 g of the expected product after crystallization from a DCM/iso ether mixture. $\alpha_D^{25}$=+127° (c=0.24; chloroform).

EXAMPLE 109

3-Amino-5-chloro-3-(2-chlorophenyl)-1-[4-(N',N'-diethylureido)benzenesulfonyl]-1,3-dihydroindol-2-one, (−) isomer This compound is prepared according to the procedure described in EXAMPLE 30 from 0.293 g of 3-amino-5-chloro-3-(2-chlorophenyl)-1,3-dihydroindol-2-one, (−) isomer, and 0.290 g of 4-(N',N'-diethylureido) benzenesulfonyl chloride. Chromatography twice on silica using a DCM/AcOEt mixture (90/10; v/v) as the eluent gives 0.065 g of the expected product after crystallization and then recrystallization from a DCM/iso ether mixture and drying at 90° C. under vacuum. $\alpha_D^{25}$=−133° (c=0.24; chloroform).

EXAMPLE 110

5-Chloro-1-[4-(2-chlorobenzamido)benzenesulfonyl]-3-(2-chlorophenyl)-1,3-dihydro-3-(methylamino)-indol-2-one A) 5-Chloro-3-(2-chlorophenyl)-1,3-dihydro-3-(methylamino)-1-(4-nitrobenzenesulfonyl)indol-2-one This compound is prepared according to the procedure described in EXAMPLE 11 from 7.03 g of 5-chloro-3-(2-chlorophenyl)-1,3-dihydro-3-(methylamino)-indol-2-one and 5.73 g of 4-nitrobenzenesulfonyl chloride. Chromatography on silica using DCM as the eluent gives 7.76 g of the expected product after crystallization from iso ether. M.p.=220°–221° C.

B) 1-(4-Aminobenzenesulfonyl)-5-chloro-3-(2-chlorophenyl)-1,3-dihydro-3-(methylamino)indol-2-one A mixture of 7.7 g of the compound obtained in the previous step, 3 g of Raney® nickel, 140 ml of EtOH and 150 ml of THF is hydrogenated at atmospheric pressure and at RT. The catalyst is filtered off on Célite® and the filtrate is concentrated under vacuum to give 6.3 g of the expected product after crystallization from iso ether. M.p.=240° C.

C) 5-Chloro-1-[4-(2-chlorobenzamido) benzenesulfonyl]-3-(2-chlorophenyl)-1,3-dihydro-3-(methylamino)indol-2-one A solution of 0.7 g of the compound obtained in the previous step in 100 ml of DCM is cooled to +5° C., 2.5 ml of triethylamine are added, a solution of 0.35 ml of 2-chlorobenzoyl chloride in 4 ml of DCM is then added dropwise and the reaction mixture is stirred for 12 hours, the temperature being allowed to rise to RT. It is concentrated under vacuum, the residue is extracted with AcOEt, the organic phase is washed with water and dried over sodium sulfate and the solvent is evaporated off under vacuum. The residue is chromatographed on silica using DCM as the eluent to give 0.31 g of the expected product after crystallization from iso ether. M.p.=221°–222° C.

EXAMPLE 111

5-Chloro-3-(2-chlorophenyl)-1,3-dihydro-3-(methylamino)-1-[4-(nicotinoylamino)benzenesulfonyl]-indol-2-one A solution of 0.5 g of the compound obtained in step B of EXAMPLE 110 in 5 ml of DCM is cooled to +5° C., 1.5 ml of triethylamine and then 0.1 g of 4-dimethylaminopyridine are added and a solution of 0.64 g of nicotinoyl chloride hydrochloride in 15 ml of DCM is added dropwise. The reaction mixture is stirred for 19 hours, the temperature being allowed to rise to RT, and concentrated under vacuum. The residue is taken up with water and extracted with AcOEt, the organic phase is washed with water and dried over sodium sulfate and the solvent is evaporated off under vacuum to give 0.41 g of the expected product, which contains 0.25 mol of iso ether after crystallization from iso ether. M.p.=228° C.

EXAMPLE 112

5-Chloro-3-(2-chlorophenyl)-1-[4-[N-(1-ethoxycarbonyl-1-methylethyl)carbamoyl]-2-methoxybenzenesulfonyl]-1,3-dihydro-3-(methylamino)indol-2-one A) Benzyl 4-[[5-chloro-3-(2-chlorophenyl)-2,3-dihydro-3-(methylamino)-2-oxoindol-1-yl]sulfonyl]-3-methoxybenzoate This compound is prepared according to the procedure described in step A of EXAMPLE 28 from 6 g of 5-chloro-3-(2-chlorophenyl)-1,3-dihydro-3-(methylamino)-indol-2-one and 6.66 g of benzyl 4-chlorosulfonyl-3-methoxybenzoate. 10.3 g of the expected product are obtained after crystallization from iso ether.

NMR spectrum at 200 MHz in DMSO-$d_6$ 1.95 ppm:d:3H 3.55 ppm:qd:1H 3.7 ppm:s:3H 5.3 ppm:s:2H 6.6 to 8.2 ppm:m:15H B) 4-[[5-Chloro-3-(2-chlorophenyl)-2,3-dihydro-3-(methylamino)-2-oxoindol-1-yl]sulfonyl]-3-methoxybenzoic acid A mixture of 10.3 g of the compound obtained in the previous step, 1 g of 10% palladium-on-charcoal and 300 ml of AcOEt is hydrogenolyzed at atmospheric pressure and at RT. The catalyst is filtered off on Célite® and the filtrate is concentrated under vacuum to give 8.05 g of the expected product after crystallization from iso ether. M.p.=248° C.

C) 5-Chloro-3-(2-chlorophenyl)-1-[4-[N-(1-ethoxycarbonyl-1-methylethyl)carbamoyl]-2-methoxybenzenesulfonyl]-1,3-dihydro-3-(methylamino)indol-2-one 1.02 g of DIPEA, 3.5 g of BOP and 1.91 g of ethyl 2-amino-2-methylpropionate hydrochloride are added successively at RT to a solution of 2 g of the compound obtained in the previous step in 25 ml of DCM. After stirring for 2 hours 30 minutes at RT, the reaction mixture is concentrated under vacuum, the residue is taken up with water and extracted with AcOEt, the organic phase is dried over sodium sulfate and the solvent is evaporated off under vacuum. The residue is chromatographed on silica using DCM and then a DCM/ AcOEt mixture (95/5; v/v) as the eluent to give 0.708 g of the expected product after crystallization from iso ether. M.p.=141° C.

EXAMPLE 113

5-Chloro-3-(2-chlorophenyl)-1-[4-[(2-furoyl)-amino]-2-methoxybenzenesulfonyl]-1,3-dihydro-3-(dimethylamino)indol-2-one A solution of 0.45 g of the compound obtained in EXAMPLE 56 in 5 ml of DCM is cooled to 0° C. and 0.6 ml of triethylamine and then 0.1 ml of 2-furoyl chloride and 0.02 g of 4-dimethylaminopyridine are added. The mixture is stirred for 1 hour at RT, 0.1 ml of 2-furoyl chloride is added and the reaction mixture is stirred for 12 hours at RT. It is concentrated under vacuum, the residue is taken up with water and extracted with AcOEt, the organic phase is washed with a 5% solution of sodium carbonate, with water and with a saturated solution of sodium chloride and dried over sodium sulfate and the solvent is evaporated off under vacuum. The residue is chromatographed on silica using DCM and then a DCM/AcOEt mixture (95/5; v/v) as the eluent to give 0.511 g of the expected product after crystallization from a DCM/iso ether mixture. M.p.=255° C.

EXAMPLE 114

5-Chloro-3-(2-chlorophenyl)-1-[4-(N',N'-diethylureido)benzenesulfonyl]-1,3-dihydro-3-[(2-hydroxyethyl)amino]indol-2-one A solution of 1.084 g of 5-chloro-3-(2-chlorophenyl)-1,3-dihydro-3-[[2-(trimethylsilyloxy)ethyl]-amino]indol-2-one in 20 ml of DMF is cooled to 0° C. under an argon atmosphere and 0.111 g of sodium hydride as a 60% dispersion in oil is added. After stirring for 25 minutes, 0.78 g of 4-(N',N'-diethylureido)-benzenesulfonyl chloride is added and the reaction mixture is stirred for 3 hours at RT. It is poured into water and extracted with AcOEt, the organic phase is washed with water and with a saturated solution of NaCl and dried over sodium sulfate and the solvent is evaporated off under vacuum. The residue is chromatographed on silica using a DCM/AcOEt mixture (70/30; v/v) as the eluent to give 0.505 g of the expected product after crystallization and then recrystallization from a DCM/iso ether mixture. M.p.=192°–193° C.

EXAMPLE 115

5-Chloro-3-(2-chlorophenyl)-1-[4-(N',N'-diethylureido)benzenesulfonyl]-1,3-dihydro-3-[[2-(2-hydroxyethoxy)ethyl]amino]indol-2-one This compound is prepared according to the procedure described in EXAMPLE 114 from 1.5 g of 5-chloro-3-(2-chlorophenyl)-1,3-dihydro-3-[[2-[2-(trimethylsilyloxy)ethoxy]ethyl]amino]indol-2-one and 1.03 g of 4-(N',N'-diethylureido)benzenesulfonyl chloride. Chromatography on silica using a DCM/AcOEt mixture (50/50; v/v) as the eluent gives 1 g of the expected product after crystallization from a DCM/iso ether mixture. M.p.=114°–118° C.

EXAMPLE 116

5-Chloro-3-(2-chlorophenyl)-1,3-dihydro-1-[4-(1,1-dimethylpropyl)benzenesulfonyl]-3-[[2-(morpholin-4-yl)ethyl]amino]indol-2-one A solution of 1 g of 5-chloro-3-(2-chlorophenyl)-1,3-dihydro-3-[[2-(morpholin-4-yl)ethyl]amino]-indol-2-one in 10 ml of DMF is cooled to 0° C. under an argon atmosphere and 0.108 g of sodium hydride as a 60% dispersion in oil is added. After stirring for 30 minutes, 0.607 g of 4-(1,1-dimethylpropyl)benzenesulfonyl chloride is added and the reaction mixture is stirred for 2 hours, the temperature being allowed to rise to RT. It is poured into water and extracted with AcOEt, the organic phase is washed with water and dried over sodium sulfate and the solvent is evaporated off under vacuum. The residue is chromatographed on silica using a DCM/AcOEt mixture (80/20; v/v) as the eluent to give 0.45 g of the expected product after crystallization from a DCM/iso ether mixture. M.p.=147° C.

EXAMPLE 117

3-[[(1S)-5-(Benzyloxycarbonylamino)-1-(methoxycarbonyl)pentyl]amino]-5-chloro-3-(2-chlorophenyl)-1-[4-(N',N'-diethylureido)benzenesulfonyl]-1,3-dihydro-indol-2-one This compound is prepared according to the procedure described in EXAMPLE 30 from 1.44 g of the compound obtained in Preparation 54 (isomer A) and 0.738 g of 4-(N',N'-diethylureido)benzenesulfonyl chloride. Chromatography on silica using a DCM/AcOEt mixture (85/15; v/v) as the eluent gives 1.10 g of the expected product in the form of a thick oil. $\alpha_D^{25}$=+65.5° (c=0.281; chloroform).

EXAMPLE 118

3-[[(1S)-5-(Benzyloxycarbonylamino)-1-(methoxycarbonyl)pentyl]amino]-5-chloro-3-(2-chlorophenyl)-1-[4-(N',N'-diethylureido)benzenesulfonyl]-1,3-dihydroindol-2-one This compound is prepared according to the procedure described in EXAMPLE 30 from 0.8 g of the compound obtained in Preparation 55 (isomer B) and 0.410 g of 4-(N',N'-diethylureido)benzenesulfonyl chloride. Chromatography on silica using a DCM/AcOEt mixture (80/20; v/v) as the eluent gives 0.85 g of the expected product in the form of an oil. $\alpha_D^{25}$=-66.9° (c=0.245; chloroform).

EXAMPLE 119

3-[[(1R)-5-(Benzyloxycarbonylamino)-1-(methoxycarbonyl)pentyl]amino]-5-chloro-3-(2-chlorophenyl)-1-[4-(N',N'-diethylureido)benzenesulfonyl]-1,3-dihydro-indol-2-one This compound is prepared according to the procedure described in EXAMPLE 30 from 0.899 g of the compound obtained in Preparation 56 (isomer A) and 0.445 g of 4-(N',N'-diethylureido)benzenesulfonyl chloride. Chromatography on silica using a gradient of a DCM/AcOEt mixture (from 95/5; v/v to 85/15; v/v) as the eluent gives 0.68 g of the expected product in the form of a foam. $\alpha_D^{25}=-60.5°$ (c=0.249; chloroform).

EXAMPLE 120

3-[[(1R)-5-(Benzyloxycarbonylamino)-1-(methoxycarbonyl)pentyl]amino]-5-chloro-3-(2-chlorophenyl)-1-[4-(N',N'-diethylureido)benzenesulfonyl]-1,3-dihydroindol-2-one This compound is prepared according to the procedure described in EXAMPLE 30 from 0.88 g of the compound obtained in Preparation 57 (isomer B) and 0.449 g of 4-(N',N'-diethylureido)benzenesulfonyl chloride. Chromatography on silica using a DCM/AcOEt mixture (80/20; v/v) as the eluent gives 0.65 g of the expected product in the form of a foam. $\alpha_D^{25}=+92.50°$ (c=0.245; chloroform).

EXAMPLE 121

3-[[(1S)-5-Amino-1-(methoxycarbonyl)pentyl]-amino]-5-chloro-3-(2-chlorophenyl)-1-[4-(N',N'-diethylureido)benzenesulfonyl]-1,3-dihydroindol-2-one trifluoroacetate A) 3-[[(1S)-5-Amino-1-(methoxycarbonyl)pentyl]amino]-5-chloro-3-(2-chlorophenyl)-1-[4-(N',N'-diethylureido)-benzenesulfonyl]-1,3-dihydroindol-2-one A solution of 1.0 g of the compound obtained in EXAMPLE 117 in 5 ml of DCM is cooled to 0° C. and 15 ml of TFA and then 0.8 g of anisole and 3 ml of trifluoromethanesulfonic acid are added. The mixture is stirred for 22 minutes at 0° C. ether is then added to the reaction mixture and the precipitate formed is filtered off. The precipitate is dissolved in AcOEt, the organic phase is washed with a 5% solution of potassium carbonate and with water and dried over sodium sulfate and the solvent is evaporated off under vacuum. The residue is chromatographed on silica using a DCM/MeOH/ triethylamine mixture (90/10/1; v/v/v) as the eluent. The product obtained is dissolved in AcOEt, the organic phase is washed twice with a 5% solution of potassium carbonate and with a saturated solution of NaCl and dried over sodium sulfate and the solvent is evaporated off under vacuum to give 0.7 g of the expected product, which is used as such.

B) 3-[[(1S)-5-(tert-Butoxycarbonylamino)-1-(methoxycarbonyl)pentyl]amino]-5-chloro-3-(2-chlorophenyl)-1-[4-(N',N'-diethylureido)benzenesulfonyl]-1,3-dihydroindol-2-one A mixture of 0.684 g of the compound obtained in the previous step, 0.26 g of di-tert-butyl dicarbonate, 0.1 g of triethylamine and 5 ml of THF is stirred for 3 hours at RT. The reaction mixture is concentrated under vacuum and the residue is chromatographed on silica using a DCM/AcOEt mixture (80/20; v/v) as the eluent to give 0.46 g of the expected product, which is used as such.

C) 3-[[(1S)-5-Amino-1-(methoxycarbonyl)pentyl]amino]-5-chloro-3-(2-chlorophenyl)-1-[4-(N',N'-diethylureido)-benzenesulfonyl]-1,3-dihydroindol-2-one trifluoroacetate A solution of 0.46 g of the compound obtained in the previous step in 3 ml of DCM is cooled to 0° C., 4 ml of TFA are added and the reaction mixture is stirred for 3 hours at 0° C. It is concentrated under vacuum, the residue is extracted with AcOEt, the organic phase is washed three times with water and with a saturated solution of NaCl and dried over sodium sulfate and the solvent is evaporated off under vacuum. The residue is taken up with iso ether and, after trituration, the solid formed is filtered off to give 0.35 g of the expected product in the form of a solid containing 0.33 mol of iso ether. M.p.=140° C. $\alpha_D^{25}=+69.8°$ (c =0.3; MeOH).

EXAMPLE 122

5-Chloro-3-(2-chlorophenyl)-3-(ethoxycarboxamido)-1,3-dihydro-1-(2-methoxy-4-nitrobenzenesulfonyl)indol-2-one This compound is prepared according to the procedure described in EXAMPLE 22 from 4.75 g of the compound obtained in EXAMPLE 16 and 1.81 ml of ethyl chloroformate. Chromatography on silica using a DCM/ hexane mixture (90/10; v/v) and then DCM as the eluent gives 4.7 g of the expected product after crystallization from a DCM/ iso ether mixture. M.p.=155°–160° C.

EXAMPLE 123

5-Chloro-3-(2-chlorophenyl)-3-(ethoxycarboxamido)-1,3-dihydro-1-[2-methoxy-4-[(morpholin-4-yl)-carbonylamino]benzenesulfonyl]indol-2-one A) 1-(4-Amino-2-methoxybenzenesulfonyl)-5-chloro-3-(2-chlorophenyl)-3-(ethoxycarboxamido)-1,3-dehydroindol-2-one A mixture of 4.45 g of the compound obtained in EXAMPLE 122, 1 g of Raney® nickel, 30 ml of MeOH and 60 ml of THF is hydrogenated at atmospheric pressure for 1 hour at RT. The catalyst is filtered off on Célite® and the filtrate is evaporated under vacuum. The residue is chromatographed on silica using DCM and then a DCM/AcOEt mixture (95/5; v/v) as the eluent to give 3.62 g of the expected product, which is used as such.

B) 5-Chloro-3-(2-chlorophenyl)-3-(ethoxycarboxamido)-1,3-dihydro-1-[2-methoxy-4-(phenoxycarboxamido)-benzenesulfonyl]indol-2-one A solution of 3.6 g of the compound obtained in the previous step in 7 ml of pyridine is cooled to 0°–5° C. and a solution of 0.9 ml of phenyl chloroformate in 10 ml of DCM is added. The mixture is stirred for 1 hour at RT, water is then added to the reaction mixture, extraction is carried out with AcOEt, the organic phase is washed with water and with a saturated solution of NaCl and dried over sodium sulfate and the solvent is evaporated off under vacuum. The residue is chromatographed on silica using DCM and then a DCM/ AcOEt mixture (95/5; v/v) as the eluent to give 3.55 g of the expected product, which is used as such.

C) 5-Chloro-3-(2-chlorophenyl)-3-(ethoxycarboxamido)-1,3-dihydro-1-[2-methoxy-4-[(morpholin-4-yl)carbonylamino]benzenesulfonyl]indol-2-one A mixture of 0.6 g of the compound obtained in the previous step, 0.16 ml of morpholine and 10 ml of THF is heated at 60° C. for 4 hours. After cooling, the precipitate formed is filtered off and dried to give 0.552 g of the expected product containing 0.33 mol of THF. M.p.= 255°–260° C.

EXAMPLE 124

5-Chloro-3-(2-chlorophenyl)-1-[4-(N',N'-diethylureido)benzenesulfonyl]-1,3-dihydro-3-[N'-methyl-N'-(2-dimethylaminoethyl)ureido]indol-2-one A) 5-Chloro-3-(2-chlorophenyl)-1-[4-(N',N'-diethylureido)benzenesulfonyl]-1,3-dihydro-3-(phenoxycarboxamido)indol-2-one 0.275 g of phenyl chloroformate is added to a solution of 0.8 g of the compound obtained in EXAMPLE 99 in 10 ml of pyridine and the mixture is stirred for 18 hours at RT. It is concentrated under vacuum, the residue is extracted with AcOEt, the organic phase is washed with water and with a 5% solution of potassium hydrogensulfate and dried over sodium sulfate and the solvent is evaporated off under vacuum. The residue is chromatographed on silica using a DCM/AcOEt mixture (90/10; v/v) as the eluent to give 0.63 g of the expected product, which is used as such.

B) 5-Chloro-3-(2-chlorophenyl)-1-[4-(N',N'-diethylureido)benzenesulfonyl]-1,3-dihydro-3-[N'-methyl-N'-(2-dimethylaminoethyl)ureido]indol-2-one A mixture of 0.63 g of the compound obtained in the previous step, 0.15 g of N,N,N'-trimethylethylenediamine, 10 ml of chloroform and 10 ml of EtOH is heated at 60° C. for 18 hours. It is concentrated under vacuum and the residue is chromatographed on silica using a DCM/MeOH mixture (90/10; v/v) as the eluent to give 0.35 g of the expected product after crystallization from a DCM/iso ether mixture. M.p.=155° C.

EXAMPLE 125

3-[N'-(Carbamoylmethyl)-N'-methylureido]-5-chloro-3-(2-chlorophenyl)-1-[4-(N',N'-diethylureido)-benzenesulfonyl]-1,3-dihydroindol-2-one hemihydrate A mixture of 1 g of the compound obtained in step A of EXAMPLE 124, 0.224 g of sarcosinamide hydrochloride, 0.234 g of DIPEA and 20 ml of chloroform is heated at 60° C. for 3 hours. It is concentrated under vacuum and the residue is chromatographed on silica using a DCM/MeOH mixture (97/3; v/v) as the eluent to give 0.65 g of the expected product after crystallization from a DCM/iso ether mixture. M.p.=150° C.

EXAMPLE 126

3-[[(1R)-5-Amino-1-(methoxycarbonyl)pentyl]-amino]-5-chloro-3-(2-chlorophenyl)-1-[4-(N',N'-diethylureido)benzenesulfonyl]-1,3-dihydroindol-2-one trifluoroacetate A) 3-[[(1R)-5-Amino-1-(methoxycarbonyl)pentyl]amino]-5-chloro-3-(2-chlorophenyl)-1-[4-(N',N'-diethylureido)-benzenesulfonyl]-1,3-dihydroindol-2-one A solution of 0.37 g of the compound obtained in EXAMPLE 120 in 7.5 ml of TFA is cooled to 0° C. and 0.2 g of anisole and 0.8 ml of trifluoromethanesulfonic acid are then added. The mixture is stirred for 22 minutes at 0° C., 50 ml of ether are then added to the reaction mixture and the precipitate formed is filtered off. The precipitate is dissolved in AcOEt, the organic phase is washed with a 5% solution of potassium carbonate to pH 9 and with water and dried over sodium sulfate and the solvent is evaporated off under vacuum to give 0.27 g of the expected product, which is used as such.

B) 3-[[(1R)-5-(tert-Butoxycarbonylamino-1-(methoxycarbonyl)pentyl]amino]-5-chloro-3-(2-chlorophenyl)-1-[4-(N',N'-diethylureido)benzenesulfonyl]-1,3-dihydroindol-2-one A mixture of 0.254 g of the compound obtained in the previous step, 0.098 g of di-tert-butyl dicarbonate, 0.05 ml of triethylamine and 4 ml of THF is stirred for one week at RT. The reaction mixture is concentrated under vacuum and the residue is chromatographed on silica using a gradient of a DCM/AcOEt mixture (from 90/10; v/v to 80/20; v/v) as the eluent to give 0.17 g of the expected product, which is used as such.

C) 3-[[(1R)-5-Amino-1-(methoxycarbonyl)pentyl]amino]-5-chloro-3-(2-chlorophenyl)-1-[4-(N',N'-diethylureido)-benzenesulfonyl]-1,3-dihydroindol-2-one trifluoroacetate A solution of 0.17 g of the compound obtained in the previous step in 0.5 ml of DCM is cooled to 0° C., 2 ml of TFA are added and the reaction mixture is stirred for 2 hours at 0° C. It is concentrated under vacuum, the residue is taken up with DCM and the solvent is evaporated off under vacuum. The residue is taken up with a DCM/iso ether mixture and, after trituration, the solid formed is filtered off to give 0.07 g of the expected product in the form of a foam after drying at 60° C. $\alpha_D^{25}$ =+82.2° (c=0.16; chloroform).

NMR spectrum at 200 MHz in DMSO-$d_6$ 0.9 to 1.18 ppm:m:12H 2.75 ppm:t:2H 3.0 ppm:qd:1H 3.35 ppm:qd:4H 3.6 ppm:s:3H 3.9 ppm:d:1H 6.7 to 8.3 ppm:m:14H 8.8 ppm:s:1H The compounds according to the invention collected in TABLE III below are prepared from the 1,3-dihydroindol-2-ones described in the Preparations by following the procedures described in the EXAMPLES above.

TABLE III

[Structure: 5-chloro-indolin-2-one with R3, R4 at 3-position; N-SO2-phenyl with R5, R6 substituents]

| Example | R3 | R4 | R5 | R6 | Salt, solvate; M.p. °C. or NMR; cristallization solvent |
|---|---|---|---|---|---|
| 127 (a) | cyclohexyl | —NH—Me | H | 4-NHCON(Et)(Et) | 255–228 DCM/iso ether |
| 128 (a) | —CH2-cyclohexyl | —NH—Me | H | 4-NHCON(Et)(Et) | 169 DCM/iso ether |
| 129 (a) | —CH2-cyclohexyl | —NHCH2CH2CN | H | 4-NHCON(Et)(Et) | 180 DCM/iso ether |
| 130 (a) | —CH2-phenyl | —NH—Me | H | 4-NHCON(Et)(Et) | 0.5 DCM 96 DCM/iso ether |
| 131 (b) | 2-chlorophenyl | —NH—Me | H | 4-NHCO-(2-methylphenyl) | 223 iso ether |
| 132 (b) | 2-chlorophenyl | —NH—Me | H | 4-NHCO-(2-methoxyphenyl) | 0.25 DCM 153–154 iso ether |
| 133 (b) | 2-chlorophenyl | —NH—Me | H | 4-NHCO-(2-thienyl) | 251 DCM |
| 134 (b) | 2-chlorophenyl | —NH—Me | H | 4-NHCO-(2-furyl) | 239 DCM |
| 135 (c) | 2-chlorophenyl | —NH—Me | 2-OMe | 4-CONH—C(Me)(Me)—CH2OH | 0.25 H2O 162 iso ether |

TABLE III-continued

[Structure: 5-chloro-indolin-2-one with N-SO2-phenyl(R5,R6) substituent, and R3, R4 at 3-position]

| Example | R3 | R4 | R5 | R6 | Salt, solvate; M.p. °C. or NMR; cristallization solvent |
|---|---|---|---|---|---|
| 136 (c) | 2-Cl-phenyl | —NH—Me | 2-OMe | 4-CONH—C(Me)(CH2OH)—CH2OH | 150 iso ether |
| 137 (c) | 2-Cl-phenyl | —NH—Me | 2-OMe | 4-CONH—C(Me)(CH2OH)—CH2CH3 | 220 DCM/iso ether |
| 138 (a) | 2-Cl-phenyl | —NHCH2CH2CH(Me)Me | H | 4-NHCON(Et)Et | 224 DCM/iso ether |
| 139 (a) | 2-Cl-phenyl | —NH-cyclohexyl | H | 4-NHCON(Et)Et | 212 DCM/iso ether |
| 140 (a) | 2-Cl-phenyl | —NH-(piperidin-4-yl, N—CO2Et) | H | 4-NHCON(Et)Et | 207 DCM/iso ether |
| 141 (a) | 2-Cl-phenyl | —NHCH2-(piperidin-4-yl, N—Boc) | H | 4-NHCON(Et)Et | 232 DCM/iso ether |
| 142 (a) 142990 | 2-Cl-phenyl | —NHCH2CH2-(piperidin-4-yl, N—Boc) | H | 4-NHCON(Et)Et | 158–160 DCM/iso ether |
| 143 (a) | 2-Cl-phenyl | —NHCH2CH2-(3-OMe-phenyl) | H | 4-NHCON(Et)Et | 138–142 DCM/iso ether |
| 144 (a) | 2-Cl-phenyl | —NHCH2CH2-(4-OMe-phenyl) | H | 4-NHCON(Et)Et | 120 DCM/iso ether |

TABLE III-continued

| Example | R₃ | R₄ | R₅ | R₆ | Salt, solvate; M.p. °C. or NMR; cristallization solvent |
|---|---|---|---|---|---|
| 145 (d) | 2-Cl-phenyl | —NHCH₂CH₂-(4-OMe-phenyl) | 2-OMe | 4-NO₂ | 75–76 |
| 146 (e), (f) et (g) | 2-Cl-phenyl | —NHCH₂CH₂-(4-OMe-phenyl) | 2-OMe | 4-NHCONEt₂ | 190–195 DCM/iso ether |
| 147 (a) | 2-Cl-phenyl | —NHCH₂CH₂-(3,4-di-OMe-phenyl) | H | 4-NHCONEt₂ | 95–100 DCM/iso ether/hexane |
| 148 (a) | 2-Cl-phenyl | —NHCH₂CH₂-(4-NO₂-phenyl) | H | 4-NHCONEt₂ | 135–138 DCM/iso ether |
| 149 (a) | 2-Cl-phenyl | —NHCH₂CH₂-(2-pyridyl) | H | 4-NHCONEt₂ | 208 DCM/iso ether |
| 150 (a) | 2-Cl-phenyl | —NH(CH₂)₂O(CH₂)₂NMe₂ | H | 4-NHCONEt₂ | 155–158 DCM/iso ether |
| 151 (h) | 2-Cl-phenyl | —NH(CH₂)₂O(CH₂)₂—NH—Boc | 2-OMe | 4-OMe | 111 DCM/iso ether |
| 152 (h) | 2-Cl-phenyl | —NH(CH₂)₂O(CH₂)₂—NH—Boc | 3-OMe | 4-OMe | oil NMR |
| 153 (a) | 2-Cl-phenyl | —NH(CH₂)₂O(CH₂)₂—NH—Boc | H | 4-NHCONEt₂ | 165 DCM/iso ether |

TABLE III-continued

| Example | R₃ | R₄ | R₅ | R₆ | Salt, solvate; M.p. °C. or NMR; cristallization solvent |
|---|---|---|---|---|---|
| 154 (h) | 2-Cl-phenyl | —NH(CH₂)₃OMe | 3-OMe | 4-OMe | 158–160 DCM/iso ether |
| 155 (a) | 2-Cl-phenyl | —NH(CH₂)₃OMe | H | 4-NHCON(Et)₂ | 175 DCM/iso ether |
| 156 (a) | 2-Cl-phenyl | —NHCH₂CH₂N(Me)₂ | H | 4-NHCON(Et)₂ | oxalate; 155 isopropanol |
| 157 (h) | 2-Cl-phenyl | —NHCH₂CH₂N(Me)₂ | 3-OMe | 4-OMe | 127 DCM/iso ether |
| 158 (a) | 2-Cl-phenyl | —N(Me)CH₂CH₂—N(Et)₂ | H | 4-NHCON(Et)₂ | 123 pentane |
| 159 (a) | 2-Cl-phenyl | —NHCH₂CH₂—N(iPr)₂ | H | 4-NHCON(Et)₂ | 180 DCM/iso ether |
| 160 (a) | 2-Cl-phenyl | —NHCH₂CH₂N(nBu)₂ | H | 4-NHCON(Et)₂ | oxalate 138 ether |
| 161 (a) | 2-Cl-phenyl | —N(Me)(CH₂)₃N(Me)₂ | H | 4-NHCON(Et)₂ | NMR |
| 162 (a) | 2-Cl-phenyl | —NH(CH₂)₃N(Et)₂ | H | 4-NHCON(Et)₂ | 159 DCM/iso ether |

TABLE III-continued

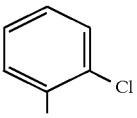

| Example | R₃ | R₄ | R₅ | R₆ | Salt, solvate; M.p. °C. or NMR; cristallization solvent |
|---|---|---|---|---|---|
| 163 (a) | 2-Cl-phenyl | —NH(CH₂)₄—NH—Boc | H | 4-NHCON(Et)₂ | 178–179 DCM/iso ether |
| 164 (h) | 2-Cl-phenyl | —NH(CH₂)₅—NH—Boc | 3-OMe | 4-OMe | 0.5 H₂O 155–156 DCM/iso ether |
| 165 (a) | 2-Cl-phenyl | —NH(CH₂)₅—NH—Boc | H | 4-NHCON(Et)₂ | 175–177 DCM/iso ether |
| 166 (a) | 2-Cl-phenyl | —NH(CH₂)₂—N(pyrrolidinyl) | H | 4-NHCON(Et)₂ | 206 DCM/iso ether |
| 167 (i) | 2-Cl-phenyl | —NH(CH₂)₂—N(piperidinyl) | H | 4-NO₂ | 140 iso ether/ hexane |
| 168 (j) | 2-Cl-phenyl | —NH(CH₂)₂—N(piperidinyl) | H | 4-NH₂ | 173 DCM/iso ether |
| 169 (k) | 2-Cl-phenyl | —NH(CH₂)₂—N(piperidinyl) | H | 4-NHCON(Et)₂ | 204 DCM/iso ether |
| 170 (a) | 2-Cl-phenyl | —NH(CH₂)₂—N(piperazinyl)N—Z | H | 4-NHCON(Et)₂ | 174–176 DCM/iso ether |
| 171 (a) | 2-Cl-phenyl | —N(piperazinyl)N—(CH₂)₂—NH—Z | H | 4-NHCON(Et)₂ | 133–138 DCM/hexane/ iso ether |

TABLE III-continued

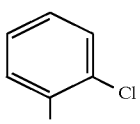

| Example | R$_3$ | R$_4$ | R$_5$ | R$_6$ | Salt, solvate; M.p. °C. or NMR; cristallization solvent |
|---|---|---|---|---|---|
| 172 (a) | 2-Cl-C$_6$H$_4$ | —NH(CH$_2$)$_2$—N(morpholino) | H | 4-NHCONEt$_2$ | 180 DCM/iso ether |
| 173 (h) | 2-Cl-C$_6$H$_4$ | —NH(CH$_2$)$_3$—N(morpholino) | 3-OMe | 4-OMe | 0.33 iso ether; 85–88 DCM/iso ether |
| 174 (a) | 2-Cl-C$_6$H$_4$ | —NH(CH$_2$)$_3$—N(morpholino) | H | 4-NHCONEt$_2$ | 184–187 DCM/iso ether |
| 175 (a) | 2-Cl-C$_6$H$_4$ | —NH—CH$_2$—C(Me)$_2$—NH—Boc | H | 4-NHCONEt$_2$ | 0.5 H$_2$O 168 DCM/iso ether |
| 176 (a) | 2-Cl-C$_6$H$_4$ | —NHCH$_2$CONEt$_2$ | H | 4-NHCONEt$_2$ | 0,5 H$_2$O 154 DCM/iso ether |
| 177 (a) | 2-Cl-C$_6$H$_4$ | —NHCH(Me)CON(CH$_2$)$_2$NMe$_2$ | H | 4-NHCONEt$_2$ | 130 DCM/iso ether |
| 178 (a) | 2-Cl-C$_6$H$_4$ | —NH(CH$_2$)$_2$CONEt$_2$ | H | 4-NHCONEt$_2$ | 164 DCM/iso ether |
| 179 (a) | 2-Cl-C$_6$H$_4$ | —NH(CH$_2$)$_3$COOMe | H | 4-NHCONEt$_2$ | 151 DCM/iso ether |
| 180 (a) | 2-Cl-C$_6$H$_4$ | —NH(CH$_2$)$_3$COOBz | H | 4-NHCONEt$_2$ | 149 DCM/iso ether |

TABLE III-continued

[Structure: 5-chloro-indolin-2-one with N-SO2-phenyl(R5,R6) substituent, 3-position bears R3 and R4]

| Example | R₃ | R₄ | R₅ | R₆ | Salt, solvate; M.p. °C. or NMR; cristallization solvent |
|---|---|---|---|---|---|
| 181 (a) | 2-Cl-phenyl | —NHCH₂CN | H | 4-NHCON(Et)₂ | 201 DCM/iso ether |
| 182 (a) | 2-Cl-phenyl | —NH(CH₂)₅CN | H | 4-NHCON(Et)₂ | 176–180 DCM/iso ether |
| 183 (a) | 2-Cl-phenyl | 4-(dimethylamino)piperidin-1-yl | H | 4-NHCON(Et)₂ | 220 DCM/iso ether |
| 184 (a) | 2-Cl-phenyl | —NHCOCH₂N(Me)₂ | H | 4-NHCON(Et)₂ | 203–205 DCM/iso ether |
| 185 (a) | 2-Cl-phenyl | —NHCOCH₂N(Et)₂ | H | 4-NHCON(Et)₂ | 132–135 DCM/iso ether |
| 186 (a) | 2-Cl-phenyl | —NHCOCH₂—N(4-Me-piperazin-1-yl) | H | 4-NHCON(Et)₂ | 137 DCM/iso ether |
| 187 (a) | 2-Cl-phenyl | —NHCO(CH₂)₂N(Et)₂ | H | 4-NHCON(Et)₂ | 174 DCM/iso ether |
| 188 (l) | 2-Cl-phenyl | —NHCOOEt | 2-OMe | 4-NHCO—N(4-Me-piperazin-1-yl) | 254–257 THF |
| 189 (m) | 2-Cl-phenyl | —NHCON(Me)(CH₂)₃N(Me)₂ | H | 4-NHCON(Et)₂ | 195-RMN DCM/iso ether |

TABLE III-continued

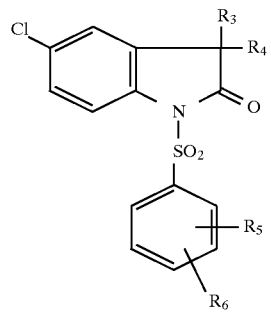

| Example | R₃ | R₄ | R₅ | R₆ | Salt, solvate; M.p. °C. or NMR; cristallization solvent |
|---|---|---|---|---|---|
| 190 (m) | 2-Cl-phenyl | —NHCON(piperidine-N(Me)₂) | H | 4-NHCON(Et)₂ | 173 DCM/iso ether |
| 191 (n) | 2-OMe-phenyl | —NH₂ | 2-OMe | 4-CONHtBu | 269 DCM/iso ether |

(a) Compound prepared according to the procedure described in EXAMPLE 30.

(b) Compound prepared according to the procedure described in step C of EXAMPLE 110 from the compound obtained in step B of EXAMPLE 110 by using the appropriate acid chlorides.

(c) Compound prepared according to the procedure described in step C of EXAMPLE 112 from the compound obtained in step B of EXAMPLE 112 by using the appropriate amines.

(d) Compound prepared according to the procedure described in EXAMPLE 16.

(e) Compound prepared according to the procedure described in EXAMPLE 103, step B.

(f) Compound prepared according to the procedure described in step A of EXAMPLE 27.

(g) Compound prepared according to the procedure described in step B of EXAMPLE 27.

(h) Compound prepared according to the procedure described in EXAMPLE 1.

(i) Compound prepared according to the procedure described in EXAMPLE 11.

(j) Compound prepared according to the procedure described in EXAMPLE 110, step B.

(k) Compound prepared according to the procedures described in step A and then step B of EXAMPLE 15.

(l) Compound prepared according to the procedure described in step C of EXAMPLE 123 using 1-methylpiperazine.

(m) Compound prepared according to the procedure described in step B of EXAMPLE 124 using the appropriate amines or heterocycles.

(n) Compound prepared according to the procedures described in steps A, C and then D of EXAMPLE 28.

NMR spectrum at 200 MHz in DMSO-$d_6$ of the compound of EXAMPLE 152

1.35 ppm:s:9H
2.4 ppm:mt:2H
3.1 ppm:qd:2H
3.3 to 3.7 ppm:m:5H
3.75 to 3.95 ppm:2s:6H
6.65 to 8.20 ppm:m:11H NMR spectrum at 200 MHz in DMSO-$d_6$ of the compound of EXAMPLE 161

1.1 ppm:t:6H
1.3 to 2.9 ppm:m:15H
3.3 ppm:qd:4H
6.6 to 8.1 ppm:m:11H
8.75 ppm:s:1H NMR spectrum at 200 MHz in DMSO-$d_6$ of the compound of EXAMPLE 189

1.0 ppm:t:6H
1.4 to 1.8 ppm:m:8H
1.8 to 2.3 ppm:mt:2H
2.5 ppm:s:3H
2.8 to 3.7 ppm:m:6H
7.1 to 7.9 ppm:m:11H
8.65 ppm s:1H
9.1 ppm bs:1H

EXAMPLE 192

5-Chloro-3-(2-chlorophenyl)-1-[4-(N',N'-diethylureido)benzenesulfonyl]-1,3-dihydro-3-[(piperid-4-yl)-amino]indol-2-one hydrobromide A mixture of 1 g of the compound obtained in EXAMPLE 140 and 40 ml of a 33% solution of hydrobromic acid in AcOH is stirred for 18 hours at RT. The reaction mixture is concentrated under vacuum at 30° C., the residue is taken up with ether and the precipitate formed is filtered off to give 0.425 g of the expected product after crystallization from an MeOH/iso ether mixture. M.p.=210° C.

EXAMPLE 193

5-Chloro-3-(2-chlorophenyl)-1-[4-(N',N'-diethylureido)benzenesulfonyl]-1,3-dihydro-3-[[(piperid-4-yl)-methyl]amino]indol-2-one trifluoroacetate A solution of 0.5 g of the compound obtained in EXAMPLE 141 in 6 ml of DCM is cooled to 0° C., 6 ml of TFA are added and the reaction mixture is stirred for two hours at 0° C. It is concentrated under vacuum and the residue is taken up with DCM and evaporated under vacuum. The residue is taken up with ether and the precipitate formed is filtered off to give 0.34 g of the expected product after crystallization from an MeOH/iso ether mixture. M.p.=218° C.

EXAMPLE 194

5-Chloro-3-(2-chlorophenyl)-1-[4-(N',N'-diethylureido)benzenesulfonyl]-1,3-dihydro-3-[[2-(piperid-4-yl)ethyl]amino]indol-2-one A solution of 0.63 g of the compound obtained in EXAMPLE 142 in 4 ml of DCM is cooled to 0° C., 7 ml of TFA are added and the reaction mixture is stirred for 5 hours 30 minutes at 0° C. It is concentrated under vacuum, the residue is taken up with a 5% solution of sodium carbonate and extracted with AcOEt, the organic phase is washed with water and dried over magnesium sulfate and the solvent is evaporated off under vacuum. The residue is chromatographed on silica using a DCM/ MeOH/triethylamine mixture (85/15/2; v/v/v) as the eluent. The product obtained is chromatographed again on silica using a DCM/MeOH/triethylamine mixture (90/10/0.5; v/v/v) as the eluent. The product obtained is dissolved in AcOEt, the organic phase is washed with water and with a saturated solution of sodium chloride and dried over magnesium sulfate and the solvent is evaporated off under vacuum to give 0.085 g of the expected product after trituration in hexane and then filtration.

NMR spectrum at 200 MHz in DMSO-$d_6$
0.6 to 1.5 ppm:m:13H
1.8 to 2.95 ppm:m:6H
3.3 ppm:qd:4H
6.6 to 8.1 ppm:m:11H
8.7 ppm:s:1H

EXAMPLE 195

3-[[2-(2-Aminoethoxy)ethyl]amino]-5-chloro-3-(2-chlorophenyl)-1,3-dihydro-1-(2,4-dimethoxybenzenesulfonyl)indol-2-one 1.25 trifluoroacetate A solution of 0.618 g of the compound obtained in EXAMPLE 151 in 2.6 ml of DCM is cooled to 0° C. and 7.7 ml of TFA are added. The mixture is stirred for 2 hours at 0° C. and concentrated under vacuum to give 0.506 g of the expected product after crystallization from a DCM/iso ether mixture. M.p.=145°–148° C.

EXAMPLE 196

3-[[2-(2-Aminoethoxy)ethyl]amino]-5-chloro-3-(2-chlorophenyl)-1,3-dihydro-1-(3,4-dimethoxybenzenesulfonyl)indol-2-one trifluoroacetate This compound is prepared according to the procedure described in EXAMPLE 195 from 2 g of the compound obtained in EXAMPLE 152 in 8.3 ml of DCM and 24.9 ml of TFA. 1.44 g of the expected product are obtained after crystallization from a DCM/THF/iso ether mixture. M.p.= 110°–114° C.

EXAMPLE 197

3-[[2-(2-Aminoethoxy)ethyl]amino]-5-chloro-3-(2-chlorophenyl)-1,3-dihydro-1-[4-(N',N'-diethylureido)benzenesulfonyl]indol-2-one trifluoroacetate This compound is prepared according to the procedure described in EXAMPLE 195 from 2.3 g of the compound obtained in EXAMPLE 153 in 14 ml of DCM and 28 ml of TFA. After concentration of the reaction mixture under vacuum, the residue is taken up with DCM and the solvent is evaporated off under vacuum. The residue is taken up with iso ether and, after trituration, the solid formed is filtered off to give 1.9 g of the expected product after crystallization from a DCM/iso ether mixture. M.p.=183° C.

EXAMPLE 198

3-[(4-Aminobutyl)amino]-5-chloro-3-(2-chlorophenyl)-1-[4-(N',N'-diethylureido)benzenesulfonyl]-1,3-dihydroindol-2-one A suspension of 0.82 g of the compound obtained in EXAMPLE 163 in 5 ml of DCM is cooled to +4° C. and 10 ml of TFA are added. The reaction mixture is stirred for 3 hours at +4° C. and concentrated under vacuum, the residue is taken up with DCM and the solvent is evaporated off under vacuum. The residue is taken up with a 5% solution of sodium carbonate and extracted with AcOEt, the organic phase is washed with a saturated solution of NaCl and with water and dried over sodium sulfate and the solvent is evaporated off under vacuum to give 0.44 g of the expected product after crystallization from a DCM/iso ether mixture. M.p.=259° C.

EXAMPLE 199

3-[(5-Aminopentyl)amino]-5-chloro-3-(2-chlorophenyl)-1-[4-(N',N'-diethylureido)benzenesulfonyl]-1,3-dihydroindol-2-one trifluoroacetate A solution of 0.9 g of the compound obtained in EXAMPLE 165 in 5 ml of DCM is cooled to 0° C. and 10 ml of TFA are added. The reaction mixture is stirred for 5 hours at 0° C. and concentrated under vacuum. The residue is taken up with water, and AcOEt and solid potassium carbonate are added. The insoluble product present at the interphase is filtered off. This insoluble product is dissolved in a DCM/MeOH mixture, the organic phase is dried over sodium sulfate and the solvents are evaporated off under vacuum to give 0.155 g of the expected product after crystallization and then recrystallization from an MeOH/iso ether mixture. M.p.=202°–204° C.

NMR spectrum at 200 MHz in DMSO-$d_6$
1.15 ppm:t:6H
1.25 to 1.7 ppm:m:6H
2.3 ppm:mt:2H
2.8 ppm:t:2H
3.3 to 3.5 ppm:m:5H
6.7 to 8.2 ppm:m:13H
8.85 ppm:s:1H

EXAMPLE 200

3-[[5-(Acetylamino)pentyl]amino]-5-chloro-3-(2-chlorophenyl)-1-[4-(N',N'-diethylureido)benzenesulfonyl]-1,3-dihydroindol-2-one A solution of 0.034 g of acetyl chloride in 0.5 ml of DCM is added at RT to a solution of 0.276 g of the compound obtained in EXAMPLE 199, in the form of the free base, and 2 ml of pyridine in 2 ml of DCM and the mixture is stirred for 1 hour. A further 0.034 g of acetyl chloride is added and the reaction mixture is stirred for 30 minutes at RT and concentrated under vacuum. The residue is taken up with AcOEt, the organic phase is washed with water and with a saturated solution of NaCl and dried over sodium sulfate and the solvent is evaporated off under vacuum. The residue is chromatographed on silica using a DCM/AcOEt mixture (50/50; v/v) as the eluent to give 0.14 g of the expected product after crystallization from a DCM/iso ether mixture. M.p.=195°–198° C.

EXAMPLE 201

5-Chloro-3-(2-chlorophenyl)-1-[4-(N',N'-diethylureido)benzenesulfonyl]-1,3-dihydro-3-[[2-(piperazin-1-yl)ethyl]amino]indol-2-one 3.3 ml of trifluoromethanesulfonic acid are added at RT to a solution of 1.2 g of the compound obtained in EXAMPLE 170 and 0.7 g of anisole in 24 ml of TFA. The mixture is stirred for precisely 10 minutes, 35 ml of ether are added and the precipitate formed is filtered off. The precipitate is dissolved in an AcOEt/water mixture, sodium carbonate is added to pH 10 and then, after decantation, the organic phase is washed with water and dried over sodium sulfate and the solvent is evaporated off under vacuum. The residue is chromatographed on silica using a DCM/MeOH/triethylamine mixture (90/10/1; v/v/v) as the eluent to give 0.825 g of the expected product after trituration in a DCM/iso ether mixture and then filtration. M.p.=260° C.

NMR spectrum at 200 MHz in DMSO-$d_6$ 1.1 ppm:t:6H
2.0 to 2.8 ppm:m:12H
3.4 ppm:qd:4H
6.7 to 8.3 ppm:m:12H
8.8 ppm:s:1H

EXAMPLE 202

5-Chloro-3-(2-chlorophenyl)-1-[4-(N',N'-diethylureido)benzenesulfonyl]-1,3-dihydro-3-[[2-(4-methyl-piperazin-1-yl)ethyl]amino]indol-2-one 0.03 g of paraformaldehyde and 0.02 g of sodium cyanoborohydride are added in portions in 4 hours to a solution of 0.16 g of the compound obtained in EXAMPLE 201 in 4 ml of MeOH and 1 ml of AcOH. The mixture is stirred overnight at RT, 5 drops of concentrated HCl are added, water is then added after 10 minutes and the reaction mixture is rendered alkaline by the addition of potassium carbonate. The organic solvents are concentrated under vacuum, the residue is extracted with DCM and dried over sodium sulfate and the solvent is evaporated off under vacuum. The residue is chromatographed on silica using a DCM/MeOH mixture (88/12; v/v) as the eluent to give 0.099 g of the expected product after crystallization from a DCM/hexane/iso ether mixture.

NMR spectrum at 200 MHz in DMSO-$d_6$ 1.1 ppm:t:6H
1.9 to 3.6 ppm:m:19H
6.6 to 8.2 ppm:m:11H
8.8 ppm:s:1H

EXAMPLE 203

3-[4-(2-Aminoethyl)piperazin-1-yl]-5-chloro-3-(2-chlorophenyl)-1-[4-(N',N'-diethylureido)benzenesulfonyl]-1,3-dihydroindol-2-one monohydrate 1.5 ml of trifluoromethanesulfonic acid are added at RT to a solution of 0.7 g of the compound obtained in EXAMPLE 171 and 0.4 g of anisole in 15 ml of TFA. The mixture is stirred for 12 minutes, ether is added and the precipitate formed is filtered off. The precipitate is dissolved in an AcOEt/water mixture, potassium carbonate is added to pH 10 and then, after decantation, the organic phase is washed with water and with a saturated solution of NaCl and dried over sodium sulfate and the solvent is evaporated off under vacuum. The residue is chromatographed on silica using a DCM/ MeOH/triethylamine mixture (90/10/1; v/v/v) as the eluent. The product obtained is dissolved in AcOEt, the organic phase is washed twice with a 5% solution of potassium carbonate and dried over sodium sulfate and the solvent is evaporated off under vacuum. The residue is taken up with a DCM/iso ether/hexane mixture, an insoluble material is filtered off and the filtrate is concentrated under vacuum. The residue is taken up with a DCM/hexane mixture to give 0.192 g of the expected product after trituration and then filtration.

NMR spectrum at 200 MHz in DMSO-$d_6$ 1.1 ppm:t:6H
1.8 to 3.0 ppm:m:12H
3.3 ppm:qd:4H
6.6 to 8.1 ppm:m:11H
8.6 ppm:s:1H

EXAMPLE 204

3-[(3-Carbamoylpropyl)amino]-5-chloro-3-(2-chlorophenyl)-1-[4-(N',N'-diethylureido)benzenesulfonyl]-1,3-dihydroindol-2-one A) 4-[N-[5-Chloro-3-(2-chlorophenyl)-1-[4-(N',N'-diethylureido)benzenesulfonyl]-2,3-dihydro-2-oxoindol-3-yl]amino]butyric acid A mixture of 0.78 ml of the compound obtained in EXAMPLE 180, 0.17 g of 5% palladium-on-charcoal and 15 ml of AcOH is hydrogenolyzed at atmospheric pressure and at RT. After 30 minutes, the catalyst is filtered off on Célite® and washed with AcOH and the filtrate is concentrated under vacuum. The residue is taken up with iso ether and, after trituration, the precipitate formed is filtered off to give 0.67 g of the expected product, which is used as such.

B) 3-[(3-Carbamoylpropyl)amino]-5-chloro-3-(2-chlorophenyl)-1-[4-(N',N'-diethylureido)benzenesulfonyl]-1,3-dihydroindol-2-one A solution of 0.67 g of the compound obtained in the previous step in 10 ml of DMF is cooled to 0° C., 0.467 g of BOP is added and the mixture is stirred for 15 minutes. 0.2 ml of a concentrated aqueous solution of ammonia is then added at 0° C. and the reaction mixture is stirred for 18 hours, the temperature being allowed to rise to RT. It is poured into water and extracted with AcOEt, the organic phase is washed with water and dried over sodium sulfate and the solvent is evaporated off under vacuum. The residue is chromatographed graphed on silica using a DCM/MeOH mixture (95/5; v/v) as the eluent to give 0.32 g of the expected product after crystallization from a DCM/iso ether mixture. M.p.=192° C.

EXAMPLE 205

5-Chloro-3-(2-chlorophenyl)-7-fluoro-1,3-dihydro-1-(2,4-dimethoxybenzenesulfonyl)-3-(methylamino) indol-2-one This compound is prepared according to the procedure described in EXAMPLE 1 from 0.25 g of 5-chloro-3-(2-chlorophenyl)-7-fluoro-1,3-dihydro-3-(methylamino)indol-2-one and 0.165 g of 2,4-dimethoxybenzenesulfonyl chloride. 0.075 g of the expected product is obtained after crystallization and recrystallization from a DCM/iso ether mixture. M.p.=183°–185° C.

EXAMPLE 206

3-(2-Chlorophenyl)-5-ethoxy-1-[4-(N',N'-diethylureido)-2-methoxybenzenesulfonyl]-1,3-dihydro-3-(dimethylamino)indol-2-one A) 3-(2-Chlorophenyl)-5-ethoxy-1,3-dihydro-1-(2-methoxy-4-nitrobenzenesulfonyl)-3-(dimethylamino) indol-2-one This compound is prepared according to the procedure described in EXAMPLE 16 from 1 g of the compound obtained in Preparation 68 and 0.762 g of 2-methoxy-4-nitrobenzenesulfonyl chloride. Chromatography on silica using DCM and then a DCM/AcOEt mixture (90/10; v/v) as the eluent gives 0.8 g of the expected product, which is used as such.

B) 1-(4-Amino-2-methoxybenzenesulfonyl)-3-(2-chlorophenyl)-5-ethoxy-1,3-dihydro-3-(dimethylamino)indol-2-one This compound is prepared according to the procedure described in step B of EXAMPLE 103 from 1.5 g of the compound obtained in the previous step. Chromatography on silica using DCM and then a DCM/AcOEt mixture (95/5; v/v) as the eluent gives 0.756 g of the expected product, which is used as such.

C) 3-(2-Chlorophenyl)-5-ethoxy-1,3-dihydro-1-[2-methoxy-4-(phenoxycarboxamido)benzenesulfonyl]-3-(dimethylamino)indol-2-one This compound is prepared according to the procedure described in step A of EXAMPLE 27 from 0.756 g of the compound obtained in the previous step and 0.22 ml of phenyl chloroformate. Chromatography on silica using DCM and then a DCM/AcOEt mixture (95/5; v/v) as the eluent gives 0.785 g of the expected product, which is used as such.

D) 3-(2-Chlorophenyl)-5-ethoxy-1-[4-(N',N'-diethylureido)-2-methoxybenzenesulfonyl]-1,3-dihydro-3-(dimethylamino)indol-2-one This compound is prepared according to the procedure described in step B of EXAMPLE 27 from 0.780 g of the compound obtained in the previous step and 0.25 ml of diethylamine. 0.605 g of the expected product is obtained after crystallization from a DCM/iso ether mixture. M.p.=212°–214° C.

The compounds according to the invention collected in TABLE IV below are prepared from the 1,3-dihydroindol-2-ones described in the Preparations and 4-(N',N'-diethylureido)benzenesulfonyl chloride by following the procedure described in EXAMPLE 30.

TABLE IV

| Example | $R_1$ | $R_2$ | $R_3$ | $R_4$ | Salt, solvate; M.p. °C. or NMR cristallization solvent |
|---|---|---|---|---|---|
| 207 | —Me | H | 2-chlorophenyl | —NH—Me | 227–228 DCM/iso ether |

TABLE IV-continued

[Structure: indolin-2-one with R1, R2 on benzene ring, R3, R4 on C-3, N-SO2-phenyl-NHCON(Et)2]

| Example | R₁ | R₂ | R₃ | R₄ | Salt, solvate; M.p. °C. or NMR cristallization solvent |
|---------|------|------|------------------|--------------------------|-----------------------------------|
| 208 | 5-Et | H | 2-Cl-phenyl | —NH—Me | 0.5 H₂O<br>230–231<br>DCM/iso ether |
| 209 | 5-OMe | H | 2-Cl-phenyl | —NH₂ | 201<br>DCM/iso ether |
| 210 | —OEt | H | 2-Cl-phenyl | —NH—Et | 218–220<br>DCM/iso ether |
| 211 | 5-F | H | 2-Cl-phenyl | —NH—Me | 1 H₂O<br>195<br>DCM/iso ether |
| 212 | 5-Cl | 4-Me | 2-Cl-phenyl | —NH—Me | 236–239<br>DCM/iso ether |
| 213 | 5-Cl | 6-Me | 2-Cl-phenyl | —NH—Me | 264<br>DCM/iso ether |
| 214 | 5-Cl | 6-Me | 2-Cl-phenyl | —NH(CH₂)₂-(4-piperidyl)N—Boc | 0.5 THF<br>210–211<br>DCM/iso ether |
| 215 | 5-Cl | 6-Cl | 2-Cl-phenyl | —NH(CH₂)₂-(4-piperidyl)N—Boc | 0.25 DCM<br>203–205<br>DCM/iso ether |
| 216 | 5-Cl | 6-Cl | 2-Cl-phenyl | —NH(CH₂)₃—OMe | 202<br>DCM/iso ether |

TABLE IV-continued

| Example | R₁ | R₂ | R₃ | R₄ | Salt, solvate; M.p. °C. or NMR cristallization solvent |
|---|---|---|---|---|---|
| 217 | 5-Cl | 6-Cl | 2-chlorophenyl | —NH(CH₂)₂O(CH₂)₂N(Me)Me | 119 DCM/iso ether |
| 218 | 5-Cl | 6-Cl | 2-chlorophenyl | —NH(CH₂)₂N(Et)Et | 155 DCM/iso ether/ hexane |
| 219 | 5-Cl | 6-Cl | 2-chlorophenyl | —NH(CH₂)₅—NH—Boc | 174 DCM/iso ether |

EXAMPLE 220

5,6-Dichloro-3-(2-chlorophenyl)-1-[4-(N',N'-diethylureido)benzenesulfonyl]-1,3-dihydro-3-[[2-(piperid-4-yl)ethyl]amino]indol-2-one 1.1 trifluoroacetate A mixture of 1.4 g of the compound obtained in EXAMPLE 215, 15 ml of TFA and 5 ml of DCM is stirred for 2 hours 15 minutes at 0° C. and the reaction mixture is concentrated under vacuum. The residue is taken up with ether and the solvent is evaporated off under vacuum, this operation being effected three times. The product obtained is dissolved in AcOEt, iso ether is added, the solvent is evaporated off slowly and the precipitate formed is filtered off and washed with iso ether to give 0.95 g of the expected product. M.p.=158°–161° C.

EXAMPLE 221

3-[(5-Aminopentyl)amino]-5,6-dichloro-3-(2-chlorophenyl)-1-[4-(N',N'-diethylureido) benzenesulfonyl]-1,3-dihydroindol-2-one trifluoroacetate A solution of 0.8 g of the compound obtained in EXAMPLE 219 in 3 ml of DCM is cooled to 0° C., 8.8 ml of TFA are added and the reaction mixture is stirred for 2 hours. It is concentrated under vacuum and the residue is crystallized from a DCM/iso ether mixture to give 0.467 g of the expected product. M.p.=195° C.

EXAMPLE 222

3-[[2-(1-tert-Butoxycarbonylpiperid-4-yl)-ethyl]amino]-5-chloro-3-(2-chlorophenyl)-1-[[1-(diethyethylaminocarbonyl)indolin-5-yl]sulfonyl]-1,3-dihydroindol-2-one A solution of 1 g of 3-[[2-(1-tert-butoxycarbonylpiperid-4-yl)ethyl]amino]-5-chloro-3-(2-chlorophenyl)-1,3-dihydroindol-2-one in 5 ml of DMF is cooled to +4° C. under an argon atmosphere and 0.087 g of sodium hydride as a 60% dispersion in oil is added. After stirring for 30 minutes at +4° C., 0.627 g of 1-(diethylaminocarbonyl) indoline-5-sulfonyl chloride is added and the mixture is stirred for 3 hours at RT. 50 ml of water are added to the reaction mixture, extraction is carried out with AcOEt, the organic phase is washed with a saturated solution of NaCl and with water and dried over sodium sulfate and the solvent is evaporated off under vacuum. The residue is chromatographed on silica using DCM and then a DCM/AcOEt mixture (88/12; v/v) as the eluent to give 1.97 g of the expected product after crystallization from a DCM/iso ether mixture. M.p.=139° C.

EXAMPLE 223

5-Chloro-3-(2-chlorophenyl)-1-[[1-(diethylaminocarbonyl)indolin-5-yl]sulfonyl]-1,3-dihydro-3-[[2-(piperid-4-yl)ethyl]amino]indol-2-one trifluoroacetate monohydrate A solution of 1.17 g of the compound obtained in EXAMPLE 222 in 7.5 ml of DCM is cooled to +4° C., 15 ml of TFA are added and the reaction mixture is stirred for 3 hours 15 minutes at +4° C. It is concentrated under vacuum, the residue is taken up with DCM and the solvent is evaporated off under vacuum, this operation being repeated twice. The residue is taken up with AcOEt, the organic phase is washed with water and with a saturated solution of NaCl and dried over sodium sulfate and the solvent is evaporated off under vacuum to give 0.6 g of the expected product after trituration in iso ether and then crystallization from a DCM/iso ether mixture. M.p.=133° C.

EXAMPLE 224

1-[(1-Acetylindolin-5-yl)sulfonyl]-5-chloro-3-(2-chlorophenyl)-1,3-dihydro-3-[(3-methoxypropyl)amino]indol-2-one hemihydrate This compound is prepared according to the procedure described in EXAMPLE 222 from 1 g of 5-chloro-3-(2-chlorophenyl)-1,3-dihydro-3-[(3-methoxypropyl)amino]indol-2-one and 0.711 g of 1-acetylindoline-5-sulfonyl chloride. 0.921 g of the expected product is obtained after crystallization from a DCM/iso ether mixture. M.p=158°–162° C.

EXAMPLE 225

5-Chloro-3-(2-chlorophenyl)-1,3-dihydro-1-[[1-(methoxycarbonyl)indolin-5-yl]sulfonyl]-3-[(3-methoxypropyl)amino]indol-2-one This compound is prepared according to the procedure described in EXAMPLE 222 from 1.3 g of 5-chloro-3-(2-chlorophenyl)-1,3-dihydro-3-[(3-methoxypropyl)amino]indol-2-one and 0.980 g of 1-(methoxycarbonyl)-indoline-5-sulfonyl chloride. 1.5 g of the expected product are obtained after crystallization from a DCM/ iso ether/hexane mixture. M.p.=98° C.

EXAMPLE 226

3-[[(1S)-5-(Benzyloxycarbonylamino)-1-(hydroxymethyl)pentyl]amino]-5-chloro-3-(2-chlorophenyl)-1-[[1-(diethylaminocarbonyl)indolin-5-yl]sulfonyl]-1,3-dihydroindol-2-one A) 3-[[(1S)-5-(Benzyloxycarbonylamino)-1-[(trimethylsilyloxy)methyl]pentyl]amino]-5-chloro-3-(2-chlorophenyl)-1-[[1-(diethylaminocarbonyl)indolin-5-yl]-sulfonyl]-1,3-dihydroindol-2-one This compound is prepared according to the procedure described in EXAMPLE 222 from the compound obtained in Preparation 60, 1.1 g of 1-(diethylaminocarbonyl)indoline-5-sulfonyl chloride, 0.162 g of sodium hydride as a 60% dispersion in oil and 20 ml of DMF. After stirring for 4 hours at RT, the reaction mixture is poured into water and extracted with AcOEt, the organic phase is washed with water and with a saturated solution of NaCl and dried over sodium sulfate and the solvent is evaporated off under vacuum to give the expected product in the form of an oil, which is used as such.

B) 3-[[(1S)-5-(Benzyloxycarbonylamino)-1-(hydroxymethyl)pentyl]amino]-5-chloro-3-(2-chlorophenyl)-1-[[1-(diethylaminocarbonyl)indolin-5-yl]sulfonyl]-1,3-dihydroindol-2-one A mixture of the compound obtained in the previous step, 30 ml of AcOH, 10 ml of THF and 10 ml of water is stirred for 30 minutes at RT. The reaction mixture is poured into water and extracted with AcOEt, the organic phase is washed with water and with a 5% solution of sodium hydrogencarbonate and dried over sodium sulfate and the solvent is evaporated off under vacuum. The residue is chromatographed on silica using a DCM/AcOEt mixture (60/40; v/v) as the eluent to give 0.23 g of the expected product in the form of a foam. $\alpha_D^{25}$ =+119.4° (c=0.25; chloroform).

EXAMPLE 227

5-Chloro-3-(2-chlorophenyl)-1-[[1-(diethylaminocarbonyl)indolin-5-yl]sulfonyl]-3-[3-(diethylamino)propionamido]-1,3-dihydroindol-2-one, (+) isomer This compound is prepared according to the procedure described in EXAMPLE 222 from 0.313 g of the compound obtained in Preparation 64, (+) isomer, and 0.21 g of 1-(diethylaminocarbonyl)indoline-5-sulfonyl chloride. Chromatography on silica using a DCM/MeOH mixture (80/20; v/v) as the eluent gives 0.22 g of the expected product after crystallization from a DCM/ hexane/iso ether mixture. M.p.=130°–133° C. $\alpha_D^{25}$=+57.7° (c=0.21; chloroform).

The compounds according to the invention collected in TABLE V below are prepared from the 1,3-dihydroindol-2-ones described in the Preparations and 1-(diethylaminocarbonyl)indoline-5-sulfonyl chloride by following the procedure described in EXAMPLE 222.

TABLE V

[Structure: indolin-2-one with R1, R2 on benzene ring, R3, R4 at 3-position; N-SO2-phenyl-(CH2CH2)-N(C(=O)NEt2) indoline substituent]

| Example | R₁ | R₂ | R₃ | R₄ | Solvate; M.p. °C. or NMR; cristallization solvent |
|---------|------|----|------|--------------------------------|--------------------------------|
| 228 | 5-Cl | H | 2-Cl-phenyl | —NH(CH₂)₃OMe | 148–152 DCM/iso ether |
| 229 | 5-Cl | H | 2-Cl-phenyl | —NH(CH₂)₂N(Et)Et | NMR |
| 230 | 5-Cl | H | 2-Cl-phenyl | —NH(CH₂)₅NH—Boc | 0.25 iso ether 148 DCM/iso ether |
| 231 | 5-Cl | H | 2-Cl-phenyl | —NH(CH₂)₂—N(piperazine)N—Z | 130 DCM/iso ether |
| 232 | 5-Cl | H | 2-Cl-phenyl | —NHCOCH₂N(Me)(CH₂)₂N(Me)Me | 175 DCM/iso ether |
| 233 | 5-Cl | H | 2-Cl-phenyl | —NHCH₂—C(Me)(Me)—N(Et)Et | 145 DCM/iso ether |
| 234 | 5-Cl | H | 2-Cl-phenyl | —NHCOCH₂N(Me)CH₂COOtBu | NMR |
| 235 | 5-Cl | H | 2-Cl-phenyl | —NHCH₂—(4-piperidinyl)N—Boc | 187 DCM/iso ether |

TABLE V-continued

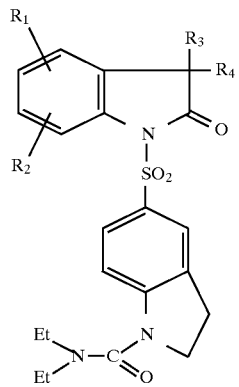

| Example | R₁ | R₂ | R₃ | R₄ | Solvate; M.p. °C. or NMR; cristallization solvent |
|---|---|---|---|---|---|
| 236 | 5-Cl | H | (2-chlorophenyl) | —NH(CH₂)₄COOBz | 122–123 DCM/iso ether |
| 237 | 5-Cl | H | (2-chlorophenyl) | —NH(CH₂)₅COOBz | 101–102 DCM/iso ether |

NMR spectrum at 200 MHz in DMSO-$d_6$ of the compound of EXAMPLE 229

0.95 ppm:t:6H
1.2 ppm:t:6H
2.1 to 2.6 ppm:m:8H
3.15 ppm:t:2H
3.3 ppm:qd:4H
3.9 ppm:t:2H
6.8 to 8.2 ppm:m:10H NMR spectrum at 200 MHz in DMSO-$d_6$ of the compound of EXAMPLE 234

1.05 ppm:t:6H
1.3 ppm:s:9H
2.2 ppm:s:3H
2.95 ppm:t:2H
3.05 to 3.3 ppm:m:8H
3.85 ppm:t:2H
6.8 to 7.8 ppm:m:10H

EXAMPLE 238

3-[(5-Aminopentyl)amino]-5-chloro-3-(2-chlorophenyl)-1-[[1-(diethylaminocarbonyl)indolin-5-yl]sulfonyl]-1,3-dihydroindol-2-one trifluoroacetate A solution of 0.83 g of the compound obtained in EXAMPLE 230 in 5 ml of DCM is cooled to 0° C. 10 ml of TFA are added and the reaction mixture is stirred for 5 hours at +4° C. It is concentrated in the cold under vacuum, the residue is taken up with DCM and the solvent is evaporated off under vacuum. The residue is taken up with a 5% solution of sodium carbonate and extracted with AcOEt, the organic phase is washed with a saturated solution of NaCl and with water and dried over sodium sulfate and the solvent is evaporated off under vacuum to give 0.150 g of the expected product after crystallization from iso ether. M.p.= 200° C.

EXAMPLE 239

3-[2-[N-(Carboxymethyl)-N-methylamino]acetamido]-5-chloro-3-(2-chlorophenyl)-1-[[1-(diethylamino-carbonyl)indolin-5-yl]sulfonyl]-1,3-dihydroindol-2-one trifluoroacetate hemihydrate 12 ml of TFA are added to a solution of 2.5 g of the compound obtained in EXAMPLE 234 in 12 ml of DCM and the mixture is stirred for 3 hours at RT. It is concentrated under vacuum at 35° C., the residue is taken up with ether and the precipitate formed is filtered off and washed with ether to give 2.2 g of the expected compound.

NMR spectrum at 200 MHz in DMSO-$d_6$ 1.2 ppm:t:6H
2.8 ppm:s:3H
3.15 ppm:t:2H P1 3.35 ppm:qd:4H
3.8 to 4.2 ppm:m:6H
7.0 to 8.0 ppm:m:10H
10.0 ppm:s:1H

EXAMPLE 240

5-Chloro-3-(2-chlorophenyl)-1-[[1-(diethylaminocarbonyl)indolin-5-yl]sulfonyl]-1,3-dihydro-3-[[(piperid-4-yl)methyl]amino]indol-2-one trifluoroacetate hemihydrate A solution of 1.5 g of the compound obtained in EXAMPLE 235 in 12 ml of DCM is cooled to 0° C. 12 ml of TFA are added and the mixture is stirred for 3 hours at 0° C. It is concentrated under vacuum at 30° C., the residue is taken up with iso ether and the precipitate formed is filtered off and washed with iso ether to give 1.36 g of the expected product.

NMR spectrum at 200 MHz in DMSO-$d_6$
0.8 to 2.4 ppm:m:13H
2.6 to 3.4 ppm:m:10H
3.9 ppm:t:2H
6.6 to 8.8 ppm:m:12H

EXAMPLE 241

1-[4-(N-tert-Butylcarbamoyl)benzyl]-5-chloro-3-(2-chlorophenyl)-3-(ethylamino)-1,3-dihydroindol-2-one A) tert-Butyl 4-[[5-chloro-3-(2-chlorophenyl)-3-(ethylamino)-2,3-dihydro-2-oxoindol-1-yl]methyl]benzoate This compound is prepared according to the procedure described in step A of EXAMPLE 96 from 1.19 g of 5-chloro-3-(2-chlorophenyl)-3-(ethylamino)-1,3-dihydroindol-2-one and 1.1 g of tert-butyl 4-bromomethylbenzoate. Chromatography on silica using a gradient of a hexane/AcOEt mixture (from 95/5; v/v to 90/10; v/v) as the eluent gives 0.9 g of the expected product, which is used as such.

B) 4-[[5-Chloro-3-(2-chlorophenyl)-3-(ethylamino)-2,3-dihydro-2-oxoindol-1-yl]methyl]benzoic acid This compound is prepared according to the procedure described in step B of EXAMPLE 96 from 0.4 g of the compound obtained in the previous step. This gives the expected product, which is used as such.

C) 1-[4-(N-tert-Butylcarbamoyl)benzyl]-5-chloro-3-(2-chlorophenyl)-3-(ethylamino)-1,3-dihydroindol-2-one A solution of the compound obtained in the previous step in 4 ml of DCM is cooled to 0° C. and 0.14 ml of DIPEA and then 0.25 ml of tert-butylamine and 0.345 g of BOP are added. The reaction mixture is stirred for 3 hours at RT and concentrated under vacuum. The residue is taken up with AcOEt, the organic phase is washed with a 5% solution of potassium carbonate, with water and with a saturated solution of NaCl and dried over sodium sulfate and the solvent is evaporated off under vacuum. The residue is chromatographed on silica using a gradient of a hexane/AcOEt mixture (from 90/10; v/v to 50/50; v/v) as the eluent to give 0.28 g of the expected product after crystallization from a DCM/iso ether mixture. M.p.=190°–195° C.

EXAMPLE 242

5-Chloro-3-(2-chlorophenyl)-3-(ethylamino)-1,3-dihydro-1-[4-[N-(2-hydroxy-1,1-dimethylethyl)carbamoyl]benzyl]indol-2-one 0.1 $H_2O$ A solution of 0.374 g of the compound obtained in step B of EXAMPLE 241 in 5 ml of DCM is cooled to 0° C. and 0.34 ml of triethylamine and then 0.16 ml of 2-amino-2-methylpropan-1-ol and 0.364 g of BOP are added. The reaction mixture is stirred for 1 hour at RT and concentrated under vacuum. The residue is taken up with AcOEt, the organic phase is washed with water, with a 5% solution of potassium carbonate and with a saturated solution of NaCl and dried over sodium sulfate and the solvent is evaporated off under vacuum. The residue is chromatographed on silica using DCM and then a DCM/AcOEt mixture (70/30; v/v) as the eluent to give 0.3 g of the expected product after crystallization from a DCM/iso ether mixture. M.p.= 170°–172° C.

NMR spectrum at 200 MHz in DMSO-$d_6$
1.1 ppm:t:3H
1.35 ppm:s:6H
2.4 ppm:mt:2H
3.25 ppm:t:1H
3.75 ppm:d:2H
4.95 ppm:t:1H
5.05 ppm:AB system:2H
6.7 to 8.4 ppm:m:11H

EXAMPLE 243

5-Chloro-3-(2-chlorophenyl)-3-(ethylamino)-1,3-dihydro-1-[4-[N-[1,1-di(hydroxymethyl)ethyl]carbamoyl]-benzyl]indol-2-one A solution of 0.172 g of 2-amino-2-methylpropane-1,3-diol in 2 ml of DMF is added at RT to a mixture of 0.374 g of the compound obtained in step B of EXAMPLE 241, 0.25 g of triethylamine, 0.364 g of BOP and 5 ml of DCM and the reaction mixture is stirred for 3 hours at RT. It is concentrated under vacuum, the residue is taken up with water and extracted with AcOEt, the organic phase is washed twice with a 5% solution of potassium carbonate, with water and with a saturated solution of NaCl and dried over sodium sulfate and the solvent is evaporated off under vacuum. The residue is chromatographed on silica using an AcOEt/DCM mixture (80/20; v/v) as the eluent to give 0.18 g of the expected product after crystallization from a DCM/iso ether mixture. M.p.=138°–141° C.

EXAMPLE 244

1-[4-(N-tert-Butylcarbamoyl)benzyl]-5-chloro-3-(2-chlorophenyl)-1,3-dihydro-3-(dimethylamino)indol-2-one, (+) isomer A) tert-Butyl 4-[[5-chloro-3-(2-chlorophenyl)-2,3-dihydro-3-(dimethylamino)-2-oxoindol-1-yl]methyl]-benzoate This compound is prepared according to the procedure described in EXAMPLE 93 from 0.62 g of the compound obtained in Preparation 76, (+) isomer, 0.085 g of sodium hydride as a 60% dispersion in oil and 0.555 g of tert-butyl 4-bromomethylbenzoate. Chromatography on silica using a DCM/AcOEt mixture (95/5; v/v) as the eluent gives 0.662 g of the expected product in the form of an oil, which is used as such.

B) 4-[[5-Chloro-3-(2-chlorophenyl)-2,3-dihydro-3-(dimethylamino)-2-oxoindol-1-yl]methyl]benzoic acid This compound is prepared according to the procedure described in step A of EXAMPLE 94 from 0.662 g of the compound obtained in the previous step. The expected product is obtained in the form of an oil, which is used as such.

C) 1-[4-(N-tert-Butylcarbamoyl)benzyl]-5-chloro-3-(2-chlorophenyl)-1,3-dihydro-3-(dimethylamino)indol-2-one, (+) isomer 0.4 g of triethylamine is added to a solution of the compound obtained in the previous step in 5 ml of DCM to bring the pH to 7 and 0.14 g of tert-butylamine and 0.564 g of BOP are then added. The mixture is stirred for 48 hours at RT, a pH of 7 being maintained by the addition of triethylamine. The mixture is concentrated under vacuum, the residue is taken up with a 5% solution of potassium carbonate and extracted with AcOEt, the organic phase is washed with water and with a saturated solution of NaCl and dried over sodium sulfate and the solvent is evaporated off under vacuum. The residue is chromatographed on silica using a DCM/ AcOEt mixture (92/8; v/v) as the eluent to give 0.225 g of the expected product after crystallization from a DCM/hexane mixture. M.p.=177°–178° C. $\alpha_D^{25}$=+148.6° (c=0.17; chloroform).

EXAMPLE 245

5-Chloro-3-(2-chlorophenyl)-1,3-dihydro-3-(dimethylamino)-1-(4-nitrobenzyl)indol-2-one This compound is prepared according to the procedure described in EXAMPLE 89 from 1 g of 5-chloro-3-(2-chlorophenyl)-1,3-dihydro-3-(dimethylamino)indol-2-one, 0.132 g of sodium hydride as a 60% dispersion in oil, 5 ml of DMF and 0.741 g of 4-nitrobenzyl bromide. Chromatography on silica using a DCM/hexane mixture (80/20; v/v) and then DCM as the eluent gives 1.32 g of the expected product after crystallization from a DCM/ iso ether mixture. M.p.=189°–193° C.

EXAMPLE 246

5-Chloro-3-(2-chlorophenyl)-1-[4-(N',N'-diethylureido)benzyl]-1,3-dihydro-3-(dimethylamino)indol-2-one A) 1-(4-Aminobenzyl)-5-chloro-3-(2-chlorophenyl)-1,3-dihydro-3-(dimethylamino)indol-2-one A mixture of 1.88 g of the compound obtained in EXAMPLE 245, 0.9 g of Raney® nickel, 40 ml of MeOH and 40 ml of THF is hydrogenated at atmospheric pressure for 2 hours at RT. The catalyst is filtered off on Célite® and the filtrate is evaporated under vacuum. The residue is chromatographed on silica using DCM and then a DCM/AcOEt mixture (95/5; v/v) as the eluent to give 1.58 g of the expected product, which is used as such.

B) 5-Chloro-3-(2-chlorophenyl)-1,3-dihydro-3-(dimethylamino)-1-[4-(phenoxycarboxamido)benzyl]indol-2-one A solution of 1 g of the compound obtained in the previous step in 5 ml of pyridine is cooled to 0° C., 0.31 ml of phenyl chloroformate is added and the mixture is stirred for 2 hours at RT. Water is added to the reaction mixture, extraction is carried out with AcoEt, the organic phase is washed with water and with a saturated solution of NaCl and dried over sodium sulfate and the solvent is evaporated off under vacuum. The residue is chromatographed on silica using DCM and then a DCM/AcOEt mixture (95/5; v/v) as the eluent to give 0.98 g of the expected product, which is used as such.

C) 5-Chloro-3-(2-chlorophenyl)-1-[4-(N',N'-diethylureido)benzyl]-1,3-dihydro-3-(dimethylamino)indol-2-one A mixture of 0.45 g of the compound obtained in the previous step, 0.17 ml of diethylamine and 5 ml of chloroform is heated at 60° C. for 4 hours. The reaction mixture is concentrated under vacuum and the residue is chromatographed on silica using DCM and then a DCM/ AcOEt mixture (95/5; v/v) as the eluent to give 0.37 g of the expected product after crystallization from a DCM/iso ether mixture. M.p.=193°–198° C.

EXAMPLE 247

3-[[5-(tert-Butoxycarbonylamino)pentyl]amino]-5-chloro-3-(2-chlorophenyl)-1,3-dihydro-1-[2-methoxy-4-(N,N-dimethylcarbamoyl)benzyl]indol-2-one hemihydrate A) Methyl 4-[[3-[[5-(tert-butoxycarbonylamino)pentyl]-amino]-5-chloro-3-(2-chlorophenyl)-2,3-dihydro-2-oxoindol-1-yl]methyl]-3-methoxybenzoate This compound is prepared according to the procedure described in EXAMPLE 89 from 2 g of 3-[[5-(tert-butoxycarbonylamino)pentyl]amino]-5 -chloro-3-(2-chlorophenyl)-1,3-dihydroindol-2-one and 1.19 g of methyl 4-bromomethyl-3-methoxybenzoate. 2.06 g of the expected product are obtained.

NMR spectrum at 200 MHz in DMSO-$d_6$ 1.10 to 1.65 ppm:m:15H 2.35 ppm:mt:2H 3.2 ppm:t:1H 3.9 ppm:s:3H 4.0 ppm:s:3H 5.0 ppm:AB system:2H 6.8 ppm:t:1H 6.85 to 8.3 ppm:m:10H B) 4-[[3-[[5-(tert-Butoxycarbonylamino)pentyl]amino]-5-chloro-3-(2-chlorophenyl)-2,3-dihydro-2-oxoindol-1-yl]methyl]-3-methoxybenzoic acid A solution of 0.375 g of lithium hydroxide monohydrate in 3 ml of water is added at RT to a solution of 1.95 g of the compound obtained in the previous step in 9.4 ml of 1,4-dioxane and the mixture is stirred for 4 days at RT. Water is added to the reaction mixture, which is neutralized to pH 7 by the addition of 1N HCl, the 1,4-dioxane is evaporated off under vacuum and the aqueous phase is acidified to pH 1 by the addition of 1N HCl. Extraction is carried out with AcOEt, the organic phase is washed with water and with a saturated solution of NaCl and dried over sodium sulfate and the solvent is evaporated off under vacuum to give 2 g of the expected product, which is used as such.

C) 3-[[5-(tert-Butoxycarbonylamino)pentyl]amino]-5-chloro-3-(2-chlorophenyl)-1,3-dihydro-1-[2-methoxy-4-(N,N-dimethylcarbamoyl)benzyl]indol-2-one hemihydrate A solution of 1 g of the compound obtained in the previous step in 10 ml of DCM is cooled to 0° C. and 0.3 ml of DIPEA and then 0.13 ml of dimethylamine and 0.69 g of BOP are added. The mixture is stirred for 12 hours at RT and concentrated under vacuum. The residue is extracted with AcOEt, the organic phase is washed with water and with a saturated solution of NaCl and dried over sodium sulfate and the solvent is evaporated off under vacuum. The residue is chromatographed on silica using DCM and then a DCM/ AcOEt mixture (80/20; v/v) as the eluent to give 0.54 g of the expected product after crystallization from a DCM/iso ether mixture. M.p.=75°–80° C.

EXAMPLE 248

3-[(5-Aminopentyl)amino]-5-chloro-3-(2-chlorophenyl)-1,3-dihydro-1-[2-methoxy-4-(N,N-dimethylcarbamoyl)benzyl]indol-2-one ditrifluoroacetate monohydrate A solution of 0.1 g of the compound obtained in EXAMPLE 247 in 1 ml of DCM is cooled to 0° C., 1.3 ml of TFA are added and the reaction mixture is stirred for 2 hours at 0° C. It is concentrated under vacuum, the residue is taken up with DCM and the solvent is evaporated off under vacuum to give 0.07 g of the expected product after crystallization and recrystallization from a DCM/iso ether mixture. M.p.=178°–180° C.

EXAMPLE 249

3-[(5-Aminopentyl)amino]-1-[4-(N-tert-butylcarbamoyl)-2-methoxybenzyl]-5-chloro-3-(2-chlorophenyl)-1,3-dihydroindol-2-one 1.5 trifluoroacetate 1.5 hydrate A) 3-[[5-(tert-Butoxycarbonylamino)pentyl]amino]-1-[4-(N-tert-butylcarbamoyl)-2-methoxybenzyl]-5-chloro-3-(2-chlorophenyl)-1,3-dihydroindol-2-one This compound is prepared according to the procedure described in step C of EXAMPLE 247 from 1.2 g of the compound obtained in step B of EXAMPLE 247, 0.33 ml of DIPEA, 0.6 ml of tert-butylamine and 0.827 g of BOP. Chromatography on silica using DCM and then a DCM/AcOEt mixture (90/10; v/v) as the eluent gives 0.685 g of the expected product, which is used as such.

B) 3-[(5-Aminopentyl)amino]-1-[4-(N-tert-butylcarbamoyl)-2-methoxybenzyl]-5-chloro-3-(2-chlorophenyl)-1,3-dihydroindol-2-one 1.5 trifluoroacetate 1.5 hydrate A solution of 0.52 g of the compound obtained in the previous step in 2 ml of DCM is cooled to 0° C., 6.3 ml of TFA are added and the mixture is stirred for 2 hours at 0° C. It is concentrated under vacuum, the residue is taken up with DCM and the solvent is evaporated off under vacuum to give 0.3 g of the expected product after crystallization and recrystallization from a DCM/iso ether mixture. M.p.=138°–140° C.

EXAMPLE 250

1-[4-(N-tert-Butylcarbamoyl)-2-methoxybenzyl]-5-chloro-3-(2-chlorophenyl)-1,3-dihydro-3-propionamidoindol-2-one A) Methyl 4-[[5-chloro-3-(2-chlorophenyl)-2,3-dihydro-2-oxo-3-propionamidoindol-1-yl]methyl]-3-methoxybenzoate 0.52 g of propionyl chloride is added at RT to a solution of 1.323 g of the compound obtained in EXAMPLE 89 in 5 ml of pyridine and the mixture is stirred for 24 hours. It is concentrated under vacuum, the residue is extracted with AcOEt, the organic phase is washed with water and with a saturated solution of NaCl and dried over sodium sulfate and the solvent is evaporated off under vacuum. The residue is chromatographed on silica using a DCM/AcOEt mixture (90/10; v/v) as the eluent to give 1.3 g of the expected product.

B) 4-[[5-Chloro-3-(2-chlorophenyl)-2,3-dihydro-2-oxo-3-propionamidoindol-1-yl]methyl]-3-methoxybenzoic acid 0.24 g of lithium hydroxide monohydrate is added at RT to a mixture of 1.3 g of the compound obtained in the previous step, 5 ml of 1,4-dioxane, 2 ml of MeOH and 2 ml of water and the reaction medium is stirred for 24 hours. It is acidified to pH 1 by the addition of concentrated HCl and the solvents are evaporated off under vacuum. The residue is taken up with water and extracted with AcOEt, the organic phase is washed with water and with a saturated solution of NaCl and dried over sodium sulfate and the solvent is evaporated off under vacuum to give 1.342 g of the expected product, which is used as such.

C) 1-[4-(N-tert-Butylcarbamoyl)-2-methoxybenzyl]-5-chloro-3-(2-chlorophenyl)-1,3-dihydro-3-propionamidoindol-2-one 0.22 g of DIPEA and then 0.382 g of BOP and 0.185 g of tert-butylamine are added at RT to a solution of 0.432 g of the compound obtained in the previous step in 7 ml of DCM and the mixture is stirred for 1 hour at RT. It is concentrated under vacuum, the residue is extracted with AcOEt, the organic phase is washed three times with a 5% solution of potassium carbonate, with water and with a saturated solution of NaCl and dried over sodium sulfate and the solvent is evaporated off under vacuum. The residue is chromatographed on silica using a DCM/AcOEt mixture (65/35; v/v) as the eluent to give 0.303 g of the expected product after crystallization from a DCM/iso ether mixture. M.p.=249° C.

The compounds according to the invention collected in TABLE VI below are prepared from the 1,3-dihydroindol-2-ones described in the Preparations by following the procedures described in the EXAMPLES above.

TABLE VI

[Structure: 5-chloro-indolin-2-one with N-CH2-phenyl(R5,R6) substituent and R3,R4 at 3-position]

| Example | R3 | R4 | R5 | R6 | Solvate; M.p. °C. or NMR; cristallization solvent |
|---|---|---|---|---|---|
| 251 (a) | 2-Cl-phenyl | —N(Me)Me | H | 4-NHCON(CH2)2N(Me)Me | 115–120 DCM/iso ether |
| 252 (b) | 2-Cl-phenyl | —NHCOEt | 2-OMe | 4-CONHC(Me)(Me)CH2N(Et)Et | 177–178 DCM/iso ether |
| 253 (c) | 2-Cl-phenyl | —NH2 | H | 4-NO2 | 172 DCM/iso ether |
| 254 (d) | 2-Cl-phenyl | —NHCOOMe | H | 4-NO2 | 203 DCM/iso ether |
| 255 (e) | 2-Cl-phenyl | —NHCOOMe | H | 4-NH2 | 225 DCM/iso ether |
| 256 (f) | 2-Cl-phenyl | —NHCOOMe | H | 4-NHCON(Et)Et | 217 DCM/iso ether |
| 257 (g) | 2-Cl-phenyl | —NH2 | H | 4-NHCON(Et)Et | 150 DCM/iso ether |
| 258 (h) | 2-OMe-phenyl | —NH2 | 2-OMe | 4-CO2Me | NMR |
| 259 (d) | 2-OMe-phenyl | —NHCOOMe | 2-OMe | 4-CO2Me | used as such |

TABLE VI-continued

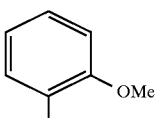

| Example | R₃ | R₄ | R₅ | R₆ | Solvate; M.p. °C. or NMR; cristallization solvent |
|---|---|---|---|---|---|
| 260 (i) | 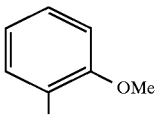 | —NHCOOMe | 2-OMe | 4-CONH-tBu | 203 DCM/iso ether |
| 261 (j) | (2-OMe-phenyl) | —NH₂ | 2-OMe | 4-CONH-tBu | 0.25 H₂O 210 DCM/iso ether |

(a) Compound prepared according to the procedure described in step C of EXAMPLE 246 by using the appropriate amines.

(b) Compound prepared according to the procedure described in step C of EXAMPLE 250 by using 2-amino-1-(diethylamino)-2-methylpropane dihydrochloride (synthesized according to J. Am. Chem. Soc., 1946, 68, 12–14).

(c) Compound prepared according to the procedure described in EXAMPLE 245.

(d) Compound prepared according to the procedure described in EXAMPLE 90.

(e) Compound prepared according to the procedure described in step A of EXAMPLE 246 from the compound obtained in EXAMPLE 254.

(f) Compound prepared according to the procedures described in step B and then step C of EXAMPLE 246.

(g) Compound prepared according to the procedure described in EXAMPLE 92 from the compound obtained in EXAMPLE 256.

(h) Compound prepared according to the procedure described in EXAMPLE 89.

(i) Compound prepared according to the procedures described in step B and then step C of EXAMPLE 250 from the compound obtained in EXAMPLE 259.

(j) Compound prepared according to the procedure described in EXAMPLE 92 from the compound obtained in EXAMPLE 260.

NMR spectrum at 200 MHz in DMSO-d₆ of the compound of EXAMPLE 258

2.65 ppm:s:2H
3.3 ppm:s:3H
3.8 ppm:s:3H
3.95 ppm:s:3H
4.95 ppm:AB system:2H
6.7 to 8.1 ppm:m:10H

EXAMPLE 262

3-Amino-1-[4-(N-tert-butylcarbamoyl)benzyl]-3-(2-chlorophenyl)-5-ethoxy-1,3-dihydroindol-2-one hemihydrate A) tert-Butyl 4-[[3-amino-3-(2-chlorophenyl)-5-ethoxy-2,3-dihydro-2-oxoindol-1-yl]methyl] benzoate This compound is prepared according to the procedure described in EXAMPLE 93 from 1 g of 3-amino-3-(2-chlorophenyl)-5-ethoxy-1,3-dihydroindol-2-one and 0.984 g of tert-butyl 4-bromomethylbenzoate. Chromatography on silica using DCM and then a DCM/AcOEt mixture (70/30; v/v) as the eluent gives 1.053 g of the expected product.

NMR spectrum at 200 MHz in DMSO-d₆
1.2 ppm:t:3H
1.55 ppm:s:9H
2.8 ppm:s:2H
3.85 ppm:qd:2H
5.0 ppm:AB system:2H
6.3 to 8.4 ppm:m:11H B) 4-[[3-Amino-3-(2-chlorophenyl)-5-ethoxy-2,3-dihydro-2-oxoindol-1-yl]methyl]benzoic acid This compound is prepared according to the procedure described in step A of EXAMPLE 94 from 1 g of the compound obtained in the previous step. This gives 0.9 g of the expected product, which is used as such.

C) 3-Amino-1-[4-(N-tert-butylcarbamoyl)benzyl]-3-(2-chlorophenyl)-5-ethoxy-1,3-dihydroindol-2-one hemihydrate This compound is prepared according to the procedure described in step C of EXAMPLE 241 from 0.4 g of the compound obtained in the previous step, 0.16 ml of DIPEA, 0.29 ml of tert-butylamine and 0.405 g of BOP. Chromatography on silica using DCM and then a DCM/AcOEt mixture (70/30; v/v) as the eluent gives 0.161 g of the expected product after crystallization from a DCM/iso ether mixture. M.p.=208°–210° C.

EXAMPLE 263

3-Amino-3-(2-chlorophenyl)-5-ethoxy-1-[4-[N-[2-(diethylamino)-1,1-dimethylethyl]carbamoyl]benzyl]-1,3-dihydroindol-2-one A solution of 0.896 g of the compound obtained in step B of EXAMPLE 262 in 10 ml of DCM is cooled to 0° C. and 0.36 ml of DIPEA is added, followed by 0.445 g of 2-amino-1-(diethylamino)-2-methylpropane dihydrochloride and then by 1.14 ml of triethylamine and 0.906 g of BOP. The mixture is stirred for 1 hour at RT and concentrated under vacuum. The residue is taken up with AcOEt, the organic phase is washed with a 5% solution of potassium carbonate, with water and with a saturated solution of NaCl and dried over sodium sulfate fate and the solvent is evaporated off under vacuum. The residue is chromatographed on silica using AcOEt and then an AcOEt/MeOH mixture (80/20; v/v) as the eluent to give 0.12 g of the expected product after crystallization from a DCM/hexane mixture. M.p.=59° C.

The compounds according to the invention collected in TABLE VII below are prepared from the 1,3-the procedures described in the EXAMPLES above.

TABLE VII

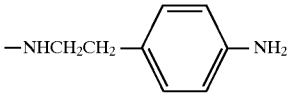

| Example | $R_2$ | $R_4$ | X | $R_5$ | $R_6$ | Salt, Solvate; M.p. °C. or NMR; cristallization solvent |
|---|---|---|---|---|---|---|
| 264 (a) | H | —NH—Me | $SO_2$ | OMe | —CONHCCH$_2$N(Me)(Me) with Me | NMR |
| 265 (b) | H | —NHCH$_2$CH$_2$—C$_6$H$_4$—NH$_2$ | $SO_2$ | H | —NHCON(Et)(Et) | 169–171 DCM/iso ether |
| 266 (c) | H | —NHCH$_2$CH$_2$—C$_6$H$_4$—N(Me)(Me) | $SO_2$ | H | —NHCON(Et)(Et) | 132–134 |
| 267 (d) | H | 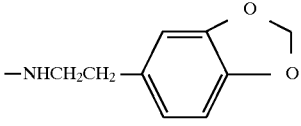 | $SO_2$ | H | —NHCON(Et)(Et) | 153–154 DCM/iso ether |
| 268 (e) | H | —NHCH$_2$—C(Me)(Me)—NH$_2$ | $SO_2$ | H | —NHCON(Et)(Et) | 1TFA, 2H$_2$O 163–164 MeOH/iso ether |

TABLE VII-continued

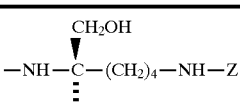

| Example | R₂ | R₄ | X | R₅ | R₆ | Salt, Solvate; M.p. °C. or NMR; cristallization solvent |
|---|---|---|---|---|---|---|
| 269 (f) | H | —NH—C(CH₂OH)(H)—(CH₂)₄—NH—Z | SO₂ | H | —NHCON(Et)(Et) | — |
| 270 (g) | H | —NH—C(CH₂OH)(H)—(CH₂)₄—NH₂ | SO₂ | H | —NHCON(Et)(Et) | — |
| 271 (d) | 4-Cl | —NHCH₂—(piperidine)N—Boc | SO₂ | H | —NHCON(Et)(Et) | 234 |
| 272 (h) | 4-Cl | —NHCH₂—(piperidine)NH | SO₂ | H | —NHCON(Et)(Et) | 1TFA 175 |
| 273 (d) | 6-Cl | —NHCH₂—(piperidine)N—Boc | SO₂ | H | —NHCON(Et)(Et) | 220 |
| 274 (i) | 6-Cl | —NHCH₂—(piperidine)NH | SO₂ | H | —NHCON(Et)(Et) | 1TFA 190 |
| 275 (d) | 6-Me | —NHCH₂—(piperidine)N—Boc | SO₂ | H | —NHCON(Et)(Et) | 264 DCM/iso ether |
| 276 (j) | 6-Me | —NHCH₂—(piperidine)NH | SO₂ | H | —NHCON(Et)(Et) | 1TFA 180 |
| 277 (k) | 6-Me | —NH(CH₂)₂—(piperidine)NH | SO₂ | H | —NHCON(Et)(Et) | NMR |
| 278 (l) | H | —NH₂ | CH₂ | H | —COOtBu | — |

TABLE VII-continued

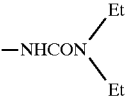

| Example | $R_2$ | $R_4$ | X | $R_5$ | $R_6$ | Salt, Solvate; M.p. °C. or NMR; cristallization solvent |
|---|---|---|---|---|---|---|
| 279 (m) | H | —$NH_2$ | $CH_2$ | H | —CONHtBu | 0,5 $H_2O$ |
| 280 (d) | H | —NH($CH_2$)$_2$S—Et | $SO_2$ | H | —NHCON(Et)(Et) | 197 DCM/iso ether |

(a) Compound prepared according to the procedure described in step C of EXAMPLE 112 from the compound obtained in step B of EXAMPLE 112 by using the appropriate amines.

(b) Compound prepared by hydrogenating the compound obtained in EXAMPLE 148 at atmospheric pressure and at RT, in the presence of Raney® nickel.

(c) Compound prepared by reacting the compound obtained in EXAMPLE 265 with paraformaldehyde, in the presence of sodium cyanoborohydride, according to the method described in EXAMPLE 34.

(d) Compound prepared according to the procedure described in EXAMPLE 30.

(e) Compound prepared according to the procedure described in EXAMPLE 198 from the compound obtained in EXAMPLE 175.

(f) Compound prepared according to the procedure described in EXAMPLE 30 from the compound obtained in Preparation 111.

(g) Compound prepared according to the procedures described in steps A, B and then C of EXAMPLE 121 from the compound obtained in EXAMPLE 269.

(h) Compound prepared according to the procedure described in EXAMPLE 193 from the compound obtained in EXAMPLE 271.

(i) Compound prepared according to the procedure described in EXAMPLE 193 from the compound obtained in EXAMPLE 273.

(j) Compound prepared according to the procedure described in EXAMPLE 193 from the compound obtained in EXAMPLE 275.

(k) Compound prepared according to the procedure described in EXAMPLE 220 from the compound obtained in EXAMPLE 214.

(l) (+) isomer; compound prepared according to the procedure described in step A of EXAMPLE 96 from the compound obtained in Preparation 28, (+) isomer. $\alpha_D^{25}=+148.8°$ (c=0.38; chloroform).

(m) (+) isomer; compound prepared according to the procedures described in step B and then step C of EXAMPLE 96 from the compound obtained in EXAMPLE 278. $\alpha_D^{25}=+91.7°$ (c=0.218; chloroform).

NMR spectrum at 200 MHz in DMSO-$d_6$ of the compound of EXAMPLE 264

1.3 ppm:s:6H 1.95 ppm:d:3H 2.1 to 2.8 ppm:m:6H 3.5 ppm:qd:1H 3.61 ppm:s:3H 6.6 to 8.2 ppm:m:11H NMR spectrum at 200 MHz in DMSO-$d_6$ of the compound of EXAMPLE 277

0.8 to 1.8 ppm:m:13H 2.2 to 2.5 ppm:m:5H 2.6 to 3.3 ppm :m:4H 3.4 ppm:qd:4H 6.8 to 8.1 ppm:m:10H The compounds according to the invention collected in TABLE VIII below are prepared by following the procedures described in the EXAMPLES above.

TABLE VIII

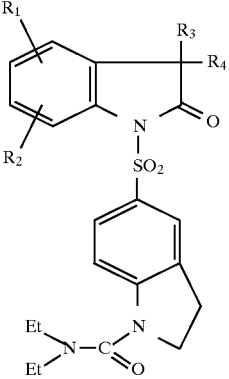

| Example | R₁ | R₂ | R₃ | R₄ | Salt, Solvate M.p. °C. or NMR; cristallization solvent |
|---|---|---|---|---|---|
| 281 (a) | 5-Cl | H | 2-Cl-phenyl | —NHCH₂—C(Me)(Me)—CH₂NH—Boc | 190 DCM/iso ether |
| 282 (b) | 5-Cl | H | 2-Cl-phenyl | —NHCH₂—C(Me)(Me)—CH₂NH₂ | 1TFA 232 ether |
| 283 (c) | 5-Cl | H | 2-Cl-phenyl | —NH(CH₂)₅COOH | 1H₂O, 0.25 iso ether 126–127 DCM/iso ether |
| 284 (d) | 5-Cl | H | 2-Cl-phenyl | —NH(CH₂)₅CONH₂ | — |
| 285 (a) | 5-Cl | 6-Cl | 2-Cl-phenyl | —NHCH₂—(piperidinyl)N—Boc | — |
| 286 (e) | 5-Cl | 6-Cl | 2-Cl-phenyl | —NHCH₂—(piperidinyl)NH | 1TFA — |

(a) Compound prepared according to the procedure described in EXAMPLE 222.
(b) Compound prepared according to the procedure described in EXAMPLE 198 from the compound obtained in EXAMPLE 281.
(c) Compound prepared by hydrogenating the compound of EXAMPLE 237 at atmospheric pressure and at RT, in the presence of 5% palladium-on-charcoal in AcOH.
(d) Compound prepared by reacting the compound obtained in EXAMPLE 283 with concentrated aqueous ammonia in the presence of BOP and DIPEA.
(e) Compound prepared according to the procedure described in EXAMPLE 193 from the compound obtained in EXAMPLE 285.

EXAMPLE 287
3-(2-Chlorophenyl)-1-[4-(N',N'-diethylureido) benzenesulfonyl]-1,3-dihydro-3-(methylamino)-5-(trifluoromethyl)indol-2-one This compound is prepared according to the procedure described in EXAMPLE 30 from the compound obtained in Preparation 112. M.p.=233°–236° C.

EXAMPLE 288
5-chloro-3-(2-chlorophenyl)-3-[3-(diethylamino) propionamido]-1-[4-(N',N'-diethylureido) benzenesulfonyl]-1,3-dihydro-4-methylindol-2-one This compound is prepared according to the procedure described in EXAMPLE 30 from the compound obtained in Preparation 114. M.p.=208°–210° C.

EXAMPLE 289

5-chloro-3-(2-chlorophenyl)-3-[3-(diethylamino)propionamido]-1-[4-(N',N'-diethylureido)benzenesulfonyl]-1,3-dihydro-6-methylindol-2-one.

This compound is prepared according to the procedure described in EXAMPLE 30 from the compound obtained in Preparation 115.

NMR spectrum at 200 MHz in DMSO $d_6$ 0.65 to 1.15 ppm:m:12H

2to 2.7 ppm:m:8H 3.1 to 3.5 ppm:m:4H 7 to 8 ppm:m:10H 8.65 ppm:s:1H 9.55 ppm:s:1H

What is claimed is:

1. A compound of formula (II')

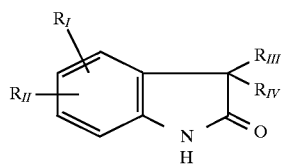

in which:

$R_I$ and $R_{II}$ are each independently a hydrogen, a halogen, a $(C_1-C_7)$alkyl, a $(C_1-C_7)$alkoxy, a trifluoromethyl, a nitro, an amino, a hydroxyl or a benzyloxy, with the proviso that $R_I$ and $R_{II}$ are not simultaneously hydrogen;

$R_{III}$ is a phenyl monosubstituted or polysubstituted by a halogen, a $(C_1-C_7)$alkyl, a hydroxyl, a $(C_1-C_7)$alkoxy, a benzyloxy or an acetoxy;

$R_{IV}$ is an azido, an amino, a 2,2-dimethylhydrazino group, a group $NR_7R_8$, a group $NR_9R_{10}$ or $NR_9R_{XI}$, a heterocyclic radical $R_{12}$ or a piperazin-1-yl radical substituted in the 4-position by a $(C_2-C_{10})$alkylene group substituted by an amino group which is free or carries a protective group;

$R_{XI}$ is a $(C_3-C_7)$cycloalkylmethyl, a group $OR_{13}$, a group $CH_2R_{36}$ or a group $\omega\text{-}R_{32}R_{33}N(C_1-C_4)$alkylcarbonyl; and $R_7$ is a $(C_1-C_7)$alkoxycarbonyl group;

$R_8$ is a $(C_1-C_7)$alkoxycarbonylamino group; or an N-methyl-N-$(C_1-C_7)$alkoxycarbonylamino group;

$R_9$ is a hydrogen atom; or a $(C_1-C_7)$alkyl group;

$R_{10}$ is a group $CR_{18}R_{19}R_{20}$; a group $(CH_2)_pR_{35}$; a $(C_2-C_{10})$alkylene group substituted by $R_{21}$; a group $CH_2CN$; a group $C(CH_3)(CH_2OH)_2$ or $C(CH_2OH)_3$; a non-aromatic $C_3-C_{18}$carbocyclic radical; a phenyl group which is unsubstituted or monosubstituted or polysubstituted by a halogen, a $(C_1-C_7)$alkyl group, a hydroxyl group, a $(C_1-C_7)$alkoxy group, a benzyloxy group, an acetoxy group, a nitro group or an amino group which is free or substituted by one or two $(C_1-C_7)$alkyl groups; a benzyl group in which the phenyl group is unsubstituted or monosubstituted or polysubstituted by a halogen atom, a $(C_1-C_7)$alkyl group, a hydroxyl group, a $(C_1-C_7)$alkoxy group, a benzyloxy group, an acetoxy group, a nitro group or an amino group which is free or substituted by one or two $(C_1-C_7)$alkyl groups; a phenethyl group in which the phenyl group is unsubstituted or monosubstituted or polysubstituted by a halogen atom, a $(C_1-C_7)$alkyl group, a hydroxyl group, a $(C_1-C_7)$alkoxy group, a benzyloxy group, an acetoxy group, a nitro group or an amino group which is free or substituted by one or two $(C_1-C_7)$alkyl groups; or a phenethyl group in which the phenyl group is substituted by a 3,4-methylenedioxy group or a 3,4-ethylenedioxy group;

$R_{12}$ is a morpholin-4-yl group; a thiomorpholin-4-yl group; an azetidin-1-yl group which is unsubstituted or substituted in the 2-position by a carboxyl group or substituted in the 3-position by an amino group which is free or carries a protective group; a perhydroazepin-1-yl group; a piperazin-1-yl group which is unsubstituted or substituted in the 4-position by $R_{25}$; a piperid-1-yl group which is unsubstituted or substituted by $R_{26}$; a pyrolidin-1-yl group which is unsubstituted or substituted by $R_{27}$; or a thiazolidin-3-yl group which is unsubstituted or substituted by $R_{27}$;

$R_{13}$ is a hydrogen atom; a $(C_1-C_7)$alkyl group; a benzyl group; an allyl group; or a tetrahydropyran-2-yl group;

$R_{18}$ is a $(C_1-C_7)$alkyl group; a phenyl group; a benzyl group; a cyclohexylmethyl group; a phenethyl group; an imidizol-4-ylmethyl group which is free or carries a protective group; an indol-3-ylmethyl group which is free or carries a protective group; a hydroxymethyl group which is free or carries a protective group; a 2-hydroxyethyl group which is free or carries a protective group; a 1-hydroxyethyl group which is free or carries a protective group; a 4-hydroxybenzyl group which is free or carries a protective group; a mercaptomethyl group which is free or carries a protective group; a 2-mercaptoethyl which is free or carries a protective group; a 2-methylthioethyl group; a 2-methylsulfinylethyl group; a 2-methylsulfonylethyl group; a 4-aminobutyl group which is free or carries a protective group; a 3-aminopropyl group which is free or carries a protective group; a carboxymethyl group which is free or carries a protective group; a 2-carboxyethyl group which is free or carries protective group; a carbamoylmethyl group; a 2-carbamoylethyl group; a 3guanidinopropyl group which is free or carries a protective group; or a non-aromatic $C_3-C_{15}$, carbocyclic radical;

$R_{19}$ is a hydrogen atom; $R_{19}$ can also be a $(C_1-C_7)$alkyl group if $R_{18}$ is a $(C_1-C_7)$alkyl group; or $R_{18}$ and $R_{19}$, together with the carbon atom to which they are bonded, form a non-aromatic $C_3-C_{15}$, carbocyclic radical;

$R_{20}$ is $R_{24}$; a group $CH_2OR_{13}$; or an aminomethyl group in which the amino group is free or substituted by one or two $(C_1-C_7)$alkyl groups or by a protective group;

$R_{21}$ is $R_{36}$; a group $OR_{37}$; a cyano group; a group $S(C_1-C_7)$ alkyl a group $SO(C_1-C_7)$alkyl; or a group $SO_2(C_1-C_7)$alkyl;

$R_{25}$ is a $(C_1-C_7)$alkyl group; a phenyl group; a benzyl group; a formyl group; a $(C_1-C_7)$alkylcarbonyl group; a $(C_1-C_7)$alkoxycarbonyl group; or a benzyloxycarbonyl group;

$R_{26}$ is $R_{24}$; an amino group which is free or substituted by one or two $(C_1-C_7)$alkyl groups or by a protective group; a group $OR_{13}$ or a group $CH_2OR_{13}$;

$R_{27}$ is $R_{24}$; a group $CH_2R_{24}$; a group $CH_2OR_{13}$; or an aminomethyl group in which the amino group is free or substituted by one or two $(C_1-C_7)$alkyl groups or by a protective group;

$R_{35}$ is a piperid-4-yl group which is unsubstituted or substituted in the 1-position by a $(C_1-C_7)$ alkoxycarbonyl group or by a $(C_1-C_7)$alkyl group; or a pyrid-2-yl group;

$R_{32}$ and $R_{33}$ each independently represent a hydrogen atom; or a $(C_1-C_7)$alkyl group; $R_{33}$ can also be an acetyl group; a phenyl group; a benzyl group; a $(C_1-C_7)$alkoxycarbonyl group; a benzyloxycarbonyl group; a $(C_1-C_6)$alkylene group substituted by $R_{24}$; a $(C_2-C_6)$alkylene group substituted by a hydroxyl or a $(C_1-C_7)$alkoxy group; or a $(C_2-C_6)$alkylene group substituted by an amino group which is free or substituted by one or two $(C_1-C_7)$alkyl groups or by a protective group; or $R_{32}$ and $R_{33}$, together with the nitrogen atom to which they are bonded, form a heterocyclic radical $R_{12}$;

$R_{24}$ is a carboxyl group: a $(C_1-C_7)$alkoxycarbonyl; a benzyloxycarbonyl group: or a carbamoyl group which is free or substituted by one or two $(C_1-C_7)$alkyl groups:

$R_{36}$ is a carboxyl group; a $(C_1-C_7)$alkoxycarbonyl group; a benzyloxycarbonyl group; or a carbamoyl group which is free or substituted by $R_{38}$ and $R_{39}$; where $R_{38}$ and $R_{39}$ each independently represent a hydrogen atom; or a $(C_1-C_7)$alkyl group; $R_{39}$ can also be a $(C_1-C_6)$ alkylene group substituted by $R_{24}$; a $(C_2-C_6)$alkylene group substituted by a hydroxyl group or a $(C_1-C_7)$ alkoxy group; or a $(C_2-C_6)$alkylene group substituted by an amino group which is free or substituted by one or two $(C_1-C_7)$alkyl groups or by a protective group; and $R_{37}$ is $R_{13}$; a $(C_3-C_7)$cycloalkyl; a $(C_1-C_6)$alkylene substituted by $R_{24}$; a $(C_2-C_6)$alkylene substituted by a hydroxyl or a $(C_1-C_7)$alkoxy; or a $(C_2-C_6)$alkylene substituted by an amino which is free or substituted by one or two $(C_1-C_7)$alkyls or by a protective group, and p is an integer which can vary from 0 to 3.

2. A compound of formula II' of claim 1, in which $R_I$ is an ethoxy group or a chlorine atom;

$R_{II}$ is hydrogen, a chlorine atom or a methyl group;

$R_{III}$ is a chlorophenyl group or a methoxyphenyl group;

$R_{IV}$ is an amino group, a group $NR_9R_{10}$ or $NR_9R_{XI}$, or a piperazin-1-yl radical substituted in the 4-position by a $(C_2-C_{10})$alkylene group substituted by an amino group which is free or carries a protective group;

$R_{10}$ is $(CH_2)_pR_{35}$ or a $(C_2-C_{10})$alkylene group substituted by $R_{21}$;

$R_{XI}$ is a group $\omega$-$R_{32}R_{33}N(C_1-C_4)$-alkylcarbonyl; and $R_9, R_{21}, R_{24}, R_{32}R_{33}, R_{35}, R_{37}$, and p are as defined in claim 1.

3. A compound of formula (II') of claim 1, in which:

$R_I$ and $R_{II}$, are each independently a hydrogen, a halogen, a $(C_1-C_7)$ alkyl, a $(C_1-C_7)$ alkoxy, a trifluoromethyl, a nitro, an amino, a hydroxyl or a benzyloxy;

$R_{III}$ is a phenyl monosubstituted or polysubstituted by a halogen, a $(C_1-C_7)$ alkyl, a hydroxyl, a $(C_1-C_7)$ alkoxy, a benzyloxy or an acetoxy;

$R_{IV}$ is an azido, an amino, a 2,2-dimethylhydrazino, a group $NR_7R_8$, a heterocyclic radical $R_{12}$ or a piperazin-1-yl radical substituted in the 4-position by a $(C_2-C_{10})$ alkylene group substituted by an amino group which is free or carries a protective group;

$R_7, R_8$ and $R_{12}$ are as defined in claim 1, provided that $R_I$ and $R_{II}$ are not simultaneously hydrogen.

\* \* \* \* \*